(12) United States Patent
Zeng et al.

(10) Patent No.: US 10,355,222 B2
(45) Date of Patent: Jul. 16, 2019

(54) ORGANIC ELECTROLUMINESCENT MATERIALS AND DEVICES

(71) Applicant: Universal Display Corporation, Ewing, NJ (US)

(72) Inventors: Lichang Zeng, Ewing, NJ (US); Gregg Kottas, Ewing, NJ (US); Chuanjun Xia, Ewing, NJ (US)

(73) Assignee: Universal Display Corporation, Ewing, NJ (US)

( * ) Notice: Subject to any disclaimer, the term of this patent is extended or adjusted under 35 U.S.C. 154(b) by 573 days.

(21) Appl. No.: 15/014,443

(22) Filed: Feb. 3, 2016

(65) Prior Publication Data

US 2016/0233436 A1 Aug. 11, 2016

Related U.S. Application Data

(60) Provisional application No. 62/113,002, filed on Feb. 6, 2015.

(51) Int. Cl.
*H01L 51/00* (2006.01)
*C09K 11/02* (2006.01)
(Continued)

(52) U.S. Cl.
CPC ........ *H01L 51/0072* (2013.01); *C07D 403/04* (2013.01); *C07D 409/04* (2013.01);
(Continued)

(58) Field of Classification Search
CPC ............... H01L 51/0072; H01L 51/006; H01L 51/0061; H01L 51/0059; H01L 51/0053; H01L 51/0073; H01L 51/0074; H01L 51/5072; H01L 51/5016; H01L 51/0085; C09K 11/06; C09K 11/025; C09K 2211/1007; C09K 2211/1029; C09K 2211/185; C07D 409/04; C07D 409/10; C07D 403/04; B32B 17/10669; B32B 2307/422; B32B 2457/206
See application file for complete search history.

(56) References Cited

U.S. PATENT DOCUMENTS 4,769,292 A 9/1988 Tang et al.
5,061,569 A 10/1991 VanSlyke et al.
(Continued)

FOREIGN PATENT DOCUMENTS

EP 650955 5/1995
EP 1238981 9/2002
(Continued)

OTHER PUBLICATIONS

Baldo et al., "Highly Efficient Phosphorescent Emission from Organic Electroluminescent Devices," Nature, vol. 395, 151-154, (1998).
(Continued)

*Primary Examiner* — Eli D. Strah
(74) *Attorney, Agent, or Firm* — Riverside Law LLP

(57) ABSTRACT

Novel compounds containing quinazoline are disclosed in this application. In these compounds, the quianzoline moiety is combined with additional aromatic groups such as dibenzothiophene, triphenylene and carbazole to provide superior properties for OLED.

14 Claims, 2 Drawing Sheets

(51) Int. Cl.
*C09K 11/06* (2006.01)
*C07D 403/04* (2006.01)
*C07D 409/10* (2006.01)
*C07D 409/04* (2006.01)
*H01L 51/50* (2006.01)
*B32B 17/10* (2006.01)

(52) U.S. Cl.
CPC .......... *C07D 409/10* (2013.01); *C09K 11/025* (2013.01); *C09K 11/06* (2013.01); *H01L 51/006* (2013.01); *H01L 51/0053* (2013.01); *H01L 51/0059* (2013.01); *H01L 51/0061* (2013.01); *H01L 51/0073* (2013.01); *H01L 51/0074* (2013.01); *B32B 17/10669* (2013.01); *B32B 2307/422* (2013.01); *B32B 2457/206* (2013.01); *C09K 2211/1007* (2013.01); *C09K 2211/1029* (2013.01); *C09K 2211/185* (2013.01); *H01L 51/0085* (2013.01); *H01L 51/5016* (2013.01); *H01L 51/5072* (2013.01)

(56) References Cited

U.S. PATENT DOCUMENTS

| | | |
|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 7,968,146 B2 | 6/2011 | Wagner et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2013/0026452 A1 | 1/2013 | Kottas et al. |
| 2013/0119354 A1 | 5/2013 | Ma et al. |
| 2014/0336392 A1 | 11/2014 | Kim et al. |
| 2014/0367654 A1 | 12/2014 | Kim et al. |

FOREIGN PATENT DOCUMENTS

| | | | |
|---|---|---|---|
| EP | 1725079 | 11/2006 | |
| EP | 2034538 | 3/2009 | |
| JP | 200511610 | 1/2005 | |
| JP | 2007123392 | 5/2007 | |
| JP | 2007254297 | 10/2007 | |
| JP | 2008074939 | 10/2009 | |
| JP | 2010/135467 | 6/2010 | |
| JP | 2014183315 | 9/2014 | |
| KR | 20120033017 | 4/2012 | |
| KR | 20120033017 A * | 4/2012 | ............ C09K 11/06 |
| KR | 20120116272 | 10/2012 | |
| KR | 20140121991 | 10/2014 | |
| KR | 20140145451 | 12/2014 | |
| WO | 2001039234 | 5/2001 | |
| WO | 2002002714 | 1/2002 | |
| WO | 2006009024 | 1/2002 | |
| WO | 215645 | 2/2002 | |
| WO | 2003040257 | 5/2003 | |
| WO | 2003060956 | 7/2003 | |
| WO | 2004093207 | 10/2004 | |
| WO | 2004/111066 | 12/2004 | |
| WO | 2004107822 | 12/2004 | |
| WO | 2005014551 | 2/2005 | |
| WO | 5019373 | 3/2005 | |
| WO | 2005030900 | 4/2005 | |
| WO | 2005089025 | 9/2005 | |
| WO | 2005123873 | 12/2005 | |
| WO | 6056418 | 6/2006 | |
| WO | 2006/072002 | 7/2006 | |
| WO | 2006082742 | 8/2006 | |
| WO | 2006098120 | 9/2006 | |
| WO | 2006103874 | 10/2006 | |
| WO | 2006114966 | 11/2006 | |
| WO | 2006132173 | 12/2006 | |
| WO | 2007/002683 | 1/2007 | |
| WO | 2007004380 | 1/2007 | |
| WO | 2007063754 | 6/2007 | |
| WO | 2007063796 | 6/2007 | |
| WO | 2008/044723 | 4/2008 | |
| WO | 2008057394 | 5/2008 | |
| WO | 8101842 | 8/2008 | |
| WO | 6100298 | 9/2008 | |
| WO | 8132085 | 11/2008 | |
| WO | 9000673 | 12/2008 | |
| WO | 2009/003898 | 1/2009 | |
| WO | 2009/008311 | 1/2009 | |
| WO | 2009/018009 | 2/2009 | |
| WO | 9050290 | 4/2009 | |

(56) References Cited

FOREIGN PATENT DOCUMENTS

| WO | 2008/056746 | 5/2009 |
|----|-------------|--------|
| WO | 2009/021126 | 5/2009 |
| WO | 2009/062578 | 5/2009 |
| WO | 2009/063833 | 5/2009 |
| WO | 2009/066778 | 5/2009 |
| WO | 2009/066779 | 5/2009 |
| WO | 2009/086028 | 7/2009 |
| WO | 9100991 | 8/2009 |
| WO | 2010011390 | 1/2010 |
| WO | 2010/111175 | 9/2010 |
| WO | 2012036482 | 3/2012 |
| WO | 2014178532 | 11/2014 |
| WO | 2014185751 | 11/2014 |

OTHER PUBLICATIONS

Baldo et al., "Very high-efficiency green organic light-emitting devices based on electrophosphorescence," Appl. Phys. Lett., vol. 75, No. 1, 4-6 (1999).

U.S. Appl. No. 13/193,221, filed Jul. 28, 2011.

U.S. Appl. No. 13/296,806, filed Nov. 15, 2011.

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Tung, Yung-Liang et al., "Organic Light-Emitting Diodes Based on Charge-Neutral $Ru^{II}$ PHosphorescent Emitters," Adv. Mater., 17(8):1059-1064 (2005).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Wong, Wai-Yeung, "Multifunctional Iridium Complexes Based on Carbazole Modules as Highly Efficient Electrophosphors," Angew. Chem. Int. Ed., 45:7800-7803 (2006).

Tang, C.W. and VanSlyke, S.A., "Organic Electroluminescent Diodes," Appl. Phys. Lett., 51(12):913-915 (1987).

Adachi, Chihaya et al., "Organic Electroluminescent Device Having a Hole Conductor as an Emitting Layer," Appl. Phys. Lett., 55(15):1489-1491 (1989).

Ma, Yuguang et al., "Triplet Luminescent Dinuclear-Gold(/) Complex-Based Light-Emitting Diodes with Low Turn-On voltage," Appl. Phys. Lett., 74(10):1361-1363 (1999).

Gao, Zhiqiang et al., "Bright-Blue Electroluminescence From a Silyl-Substituted ter-(phenylene-vinylene) derivative," Appl. Phys. Lett., 74(6):865-867 (1999).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Hung, L.S. et al., "Anode Modification in Organic Light-Emitting Diodes by Low-Frequency Plasma Polymerization of $CHF_3$," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Wang, Y. et al., "Highly Efficient Electroluminescent Materials Based on Fluorinated Organometallic Iridium Compounds," Appl. Phys. Lett., 79(4):449-451 (2001).

Kwong, Raymond C. et al., "High Operational Stability of Electrophosphorescent Devices," Appl. Phys. Lett., 81(1):162-164 (2002).

Holmes, R.J. et al., "Blue Organic Electrophosphorescence Using Exothermic Host-Guest Energy Transfer," Appl. Phys. Lett., 82(15):2422-2424 (2003).

Sotoyama, Wataru et al., "Efficient Organic Light-Emitting Diodes with Phosphorescent Platinum Complexes Containing N^C^N-Coordinating Tridentate Ligand," Appl. Phys. Lett., 86:153505-1-153505-3 (2005).

Okumoto, Kenji et al., "Green Fluorescent Organic Light-Emitting Device with External Quantum Efficiency of Nearly 10%," Appl. Phys. Lett., 89:063504-1-063504-3 (2006).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Aonuma, Masaki et al., "Material Design of Hole Transport Materials Capable of Thick-Film Formation in Organic Light Emitting Diodes," Appl. Phys. Lett., 90:183503-1-183503-3 (2007).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

Adachi, Chihaya et al., "High-Efficiency Red Electrophosphorescence Devices," Appl. Phys. Lett., 78(11):1622-1624 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Hamada, Yuji et al., "High Luminance in Organic Electroluminescent Devices with Bis(10-hydroxybenzo[h]quinolinato)beryllium as an Emitter," Chem. Lett., 905-906 (1993).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4):592-593 (2005).

Mi, Bao-Xiu et al., "Thermally Stable Hole-Transporting Material for Organic Light-Emitting Diode: an Isoindole Derivative," Chem. Mater., 15(16):3148-3151 (2003).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Niu, Yu-Hua et al., "Highly Efficient Electrophosphorescent Devices with Saturated Red Emission from a Neutral Osmium Complex," Chem. Mater., 17(13):3532-3536 (2005).

Lo, Shih-Chun et al., "Blue Phosphorescence from Iridium(III) Complexes at Room Temperature," Chem. Mater., 18(21):5119-5129 (2006).

Takizawa, Shin-ya et al., "Phosphorescent Iridium Complexes Based on 2-Phenylimidazo[1,2-α]pyridine Ligands: Tuning of Emission Color toward the Blue Region and Application to Polymer Light-Emitting Devices," Inorg. Chem., 46(10):4308-4319 (2007).

Lamansky, Sergey et al., "Synthesis and Characterization of Phosphorescent Cyclometalated Iridium Complexes," Inorg. Chem., 40(7):1704-1711 (2001).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Noda, Tetsuya and Shirota, Yasuhiko, "5,5'-Bis(dimesitylboryl)-2,2'-bithiophene and 5,5"-Bis(dimesitylboryl)-2,2':5',2"-terthiophene as a Novel Family of Electron-Transporting Amorphous Molecular Materials," J. Am. Chem. Soc., 120 (37):9714-9715 (1998).

Sakamoto, Youichi et al., "Synthesis, Characterization, and Electron-Transport Property of Perfluorinated Phenylene Dendrimers," J. Am. Chem. Soc., 122(8):1832-1833 (2000).

Adachi, Chihaya et al., "Nearly 100% Internal Phosphorescence Efficiency in an Organic Light Emitting Device," J. Appl. Phys., 90(10):5048-5051 (2001).

Shirota, Yasuhiko et al., "Starburst Molecules Based on p-Electron Systems as Materials for Organic Electroluminescent Devices," Journal of Luminescence, 72-74:985-991 (1997).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kido, Junji et al., 1,2,4-Triazole Derivative as an Electron Transport Layer in Organic Electroluminescent Devices, Jpn. J. Appl. Phys., 32:L917-L920 (1993).

Van Slyke, S. A. et al., "Organic Electroluminescent Devices with Improved Stability," Appl. Phys. Lett., 69(15):2160-2162 (1996).

(56) References Cited

OTHER PUBLICATIONS

Guo, Tzung-Fang et al., "Highly Efficient Electrophosphorescent Polymer Light-Emitting Devices," *Organic Electronics*, 1:15-20 (2000).

Palilis, Leonidas C., "High Efficiency Molecular Organic Light-Emitting Diodes Based on Silole Derivatives and Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergård et al., "Langmuir-Blodgett Light-Emitting Diodes of Poly(3-Hexylthiophene): Electro-Optical Characteristics Related to Structure," *Synthetic Metals*, 87:171-177 (1997).

Hu, Nan-Xing et al., "Novel High $T_g$ Hole-Transport Molecules Based on Indolo[3,2-b]carbazoles for Organic Light-Emitting Devices," *Synthetic Metals*, 111-112:421-424 (2000).

Salbeck, J. et al., "Low Molecular Organic Glasses for Blue Electroluminescence," *Synthetic Metals*, 91:209-215 (1997).

\* cited by examiner

ORGANIC ELECTROLUMINESCENT MATERIALS AND DEVICES

CROSS-REFERENCE TO RELATED APPLICATIONS

This application claims priority from U.S. Provisional Patent Application Ser. No. 62/113,002, filed Feb. 6, 2015, the entire contents of which is incorporated herein by reference.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to compounds for use as host materials or electron transporting materials, and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

One example of a green emissive molecule is tris(2-phenylpyridine)iridium, denoted Ir(ppy)$_3$, which has the following structure:

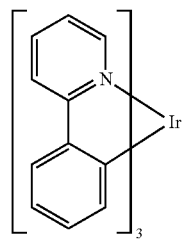

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

There is a need in the art for quinazoline compounds of the prior art with improved energetic and electrical properties, but also increased morphological stability. The present invention addresses this need in the art.

SUMMARY

According to an embodiment, a compound is provided that has the structure of Formula I shown below:

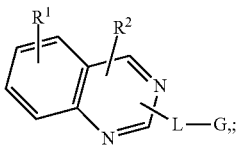

Formula I wherein L is selected from the group consisting of a direct bond, phenyl, biphenyl, terphenyl, fluorene, pyridine, pyrimidine, pyrazine, pyridazine, triazine, naphthalene, anthracene, and combinations thereof;

G is selected from the group consisting of:

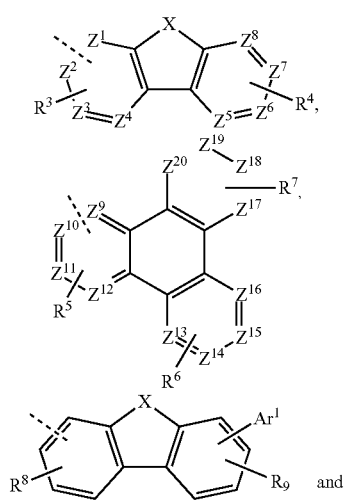

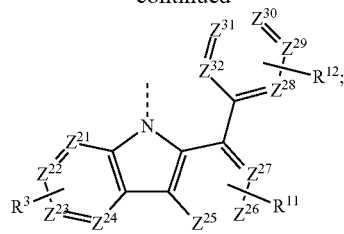

wherein $R^1$ to $R^9$ are independently selected from the group consisting of hydrogen, deuterium, alkyl, cycloalkyl, alkoxyl, halogen, nitro, silyl, benzene, biphenyl, terphenyl, naphthalene, phenanthrene, benzofuran, benzothiophene, benzoselenophene, dibenzofuran, dibenzothiophene, dibenzoselenophene, fluorene, triphenylene, pyridine, pyrimidine, pyrazine, pyridazine, triazine, quinoline, phenanthroline, aza-dibenzofuran, aza-dibenzothiophene, aza-dibenzoselenophene, aza-fluorene and aza-triphenylene, and combinations thereof;

wherein $R^{10}$ to $R^{11}$ are independently selected from the group consisting of hydrogen, deuterium, alkyl, heteroalkyl, cycloalkyl, alkoxyl, halogen, nitro, carbonyl, amino and silyl, and combinations thereof;

wherein $R^{12}$ is selected from the group consisting of hydrogen, deuterium, alkyl, heteroalkyl, cycloalkyl, alkoxyl, halogen, nitro, carbonyl, amino, silyl, aryl, heteroaryl, and combinations thereof;

wherein $Z^1$ to $Z^{32}$ are each independently selected from the group consisting of carbon and nitrogen;

wherein at least one of $Z^1$, $Z^2$, $Z^3$, $Z^4$, $Z^5$, $Z^6$, $Z^7$ and $Z^8$ is nitrogen; at least one of $Z^9$, $Z^{10}$, $Z^{11}$, $Z^{12}$, $Z^{13}$, $Z^{14}$, $Z^{15}$, $Z^{16}$, $Z^{17}$, $Z^{18}$, $Z^{19}$ and $Z^{20}$ is nitrogen; at least one of $Z^1$, $Z^2$, $Z^3$ and $Z^4$ is carbon; and at least one of $Z^9$, $Z^{10}$, $Z^{11}$ and $Z^{12}$ is carbon;

wherein when any of $Z^1$ to $Z^{32}$ is nitrogen, there is no substitution on that nitrogen;

wherein $R^1$, $R^4$, $R^6$, $R^7$ and $R^{10}$ each independently represent mono, di, tri or tetra substitution, or no substitution;

wherein $R^3$, $R^5$, $R^8$, $R^9$ and $R^{11}$ each independently represent mono, di or tri substitution, or no substitution;

wherein $R^2$ represents mono substitution, or no substitution;

wherein $R^{12}$ represents mono, di, tri, tetra or penta substitution, or no substitution;

wherein $Ar^1$ is selected from the group consisting of benzene, biphenyl, terphenyl, triphenylene, fluorene, pyridine, pyramidine, triazine, and combinations thereof;

wherein X is selected from the group consisting of O, S, and Se; and wherein L and $Ar^1$ are each optionally further substituted with one or more substituents selected from the group consisting of deuterium, alkyl, alkoxyl, halogen, silyl, nitro, benzene, biphenyl, terphenyl, naphthalene, phenanthrene, dibenzofuran, dibenzothiophene, dibenzoselenophene, fluorene, triphenylene, pyridine, pyrimidine, pyrazine, pyridazine, triazine, quinoline, phenanthroline, aza-dibenzofuran, aza-dibenzothiophene, aza-dibenzoselenophene, aza-fluorene and aza-triphenylene, and combinations thereof.

According to another embodiment, an organic light emitting diode/device (OLED) is also provided. The OLED can include an anode, a cathode, and an organic layer, disposed between the anode and the cathode. The organic layer can include a compound of Formula I. According to yet another embodiment, the organic light emitting device is incorporated into a device selected from a consumer product, an electronic component module, and/or a lighting panel.

According to another embodiment, the invention provides a formulation comprising a compound of Formula I.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
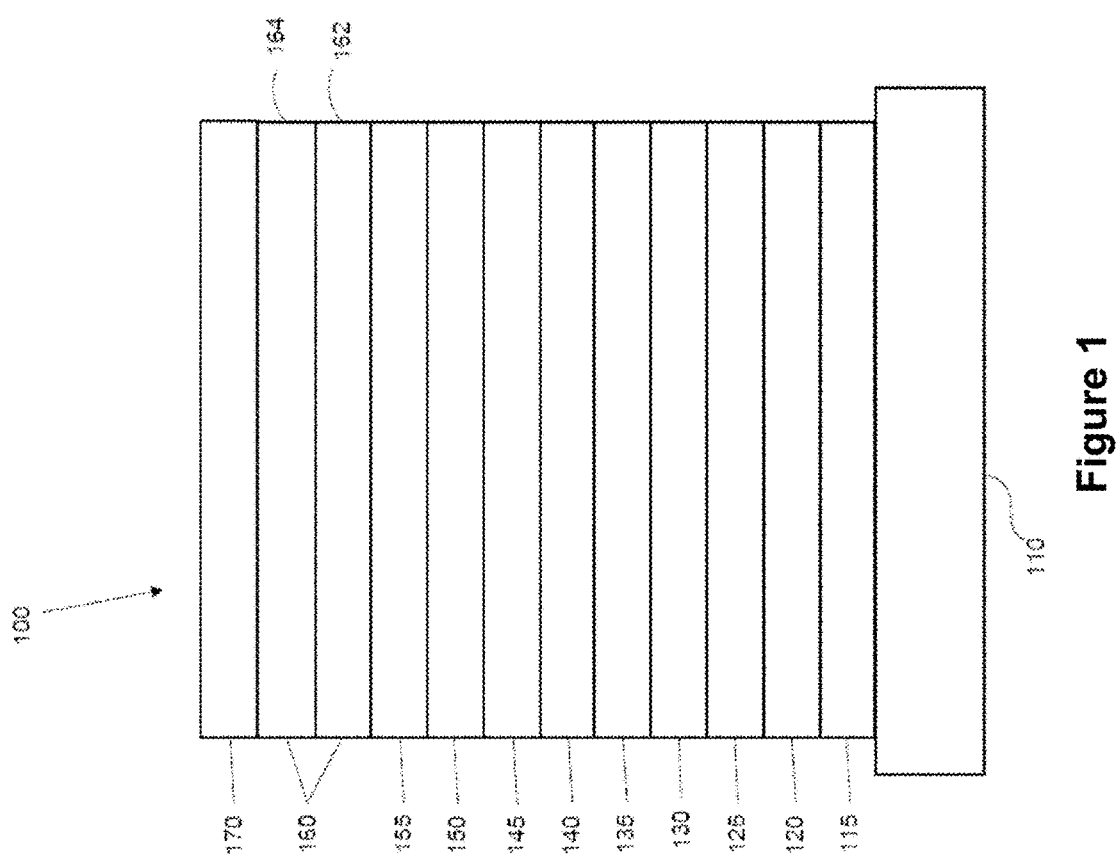
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
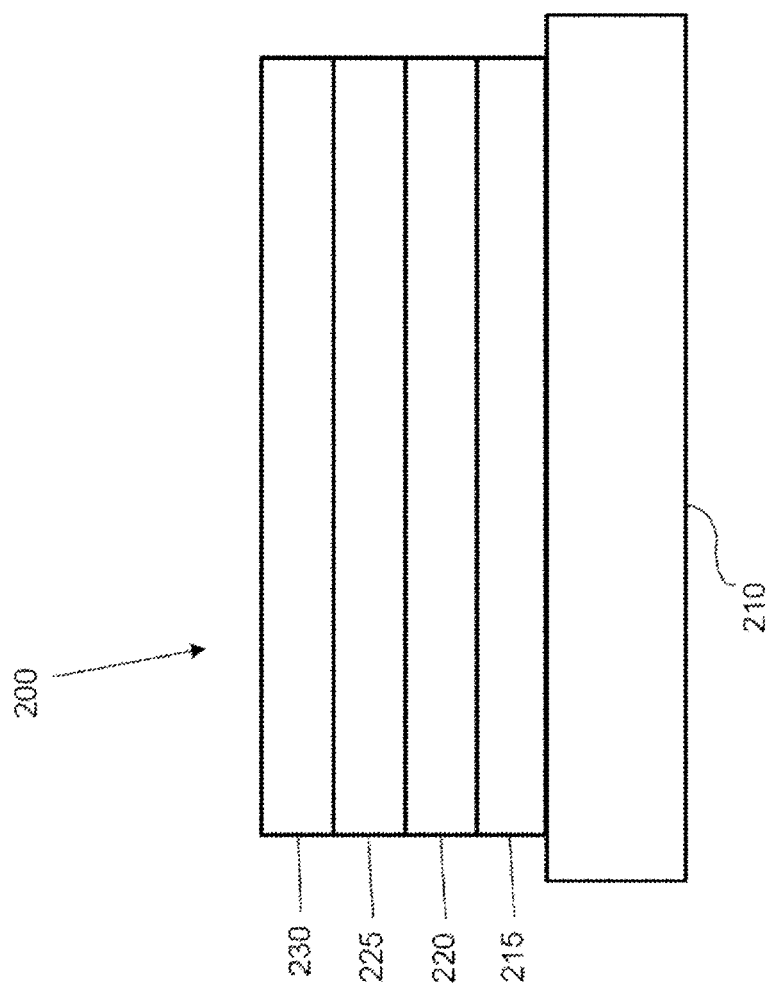
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), wearable device, laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" as used herein contemplates cyclic alkyl radicals. Preferred cycloalkyl groups are those containing 3 to 10 ring carbon atoms and includes cyclopropyl, cyclopentyl, cyclohexyl, adamantyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 or 7 ring atoms which includes at least one hetero atom, and includes cyclic amines such as morpholino, piperidino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" as used herein contemplates single-ring hetero-aromatic groups that may include from one to five heteroatoms. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, and aza-analogs thereof. Additionally, the heteroaryl group may be optionally substituted.

The alkyl, cycloalkyl, alkenyl, alkynyl, aralkyl, heterocyclic group, aryl, and heteroaryl may be unsubstituted or may be substituted with one or more substituents selected from the group consisting of deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In one aspect, the present invention includes a class of novel compounds containing dibenzo-X (for example, dibenzofuran, dibenzothiophene, or dibenzoselenophene; herein referred to as DBX), triphenylene, or carbazole connected to a quinazoline. Quinazoline, DBX, triphenylene and carbazole have appropriate energy levels and excellent charge-transport capability, and are valuable for constructing OLED materials. Combining quinazoline and DBX, triphenylene or carbazole not only strengthens their energetic and electrical properties but also increases their morphological stability. Further derivatization on these building blocks fine-tunes energy levels and molecular assembly characteristics, which is conducive to improving OLED device performance.

In one aspect, the present invention includes a compound having Formula I:

Formula I

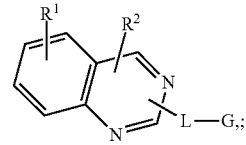

wherein L is selected from the group consisting of a direct bond, phenyl, biphenyl, terphenyl, fluorene, pyridine, pyrimidine, pyrazine, pyridazine, triazine, naphthalene, anthracene, and combinations thereof;

G is selected from the group consisting of:

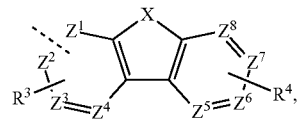

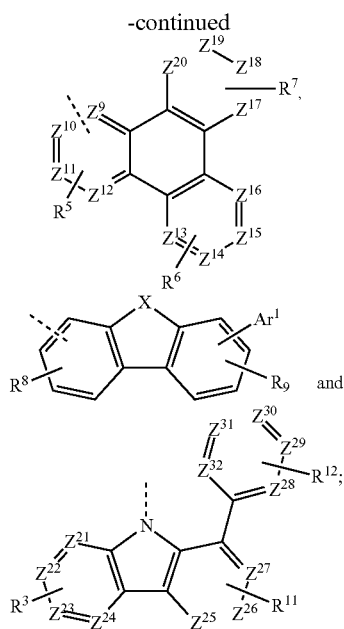

wherein $R^1$ to $R^9$ are independently selected from the group consisting of hydrogen, deuterium, alkyl, cycloalkyl, alkoxyl, halogen, nitro, silyl, benzene, biphenyl, terphenyl, naphthalene, phenanthrene, benzofuran, benzothiophene, benzoselenophene, dibenzofuran, dibenzothiophene, dibenzoselenophene, fluorene, triphenylene, pyridine, pyrimidine, pyrazine, pyridazine, triazine, quinoline, phenanthroline, aza-dibenzofuran, aza-dibenzothiophene, aza-dibenzoselenophene, aza-fluorene and aza-triphenylene, and combinations thereof;

wherein $R^{10}$ to $R^{11}$ are independently selected from the group consisting of hydrogen, deuterium, alkyl, heteroalkyl, cycloalkyl, alkoxyl, halogen, nitro, carbonyl, amino and silyl, and combinations thereof;

wherein $R^{12}$ is selected from the group consisting of hydrogen, deuterium, alkyl, heteroalkyl, cycloalkyl, alkoxyl, halogen, nitro, carbonyl, amino, silyl, aryl, heteroaryl, and combinations thereof;

wherein $Z^1$ to $Z^{32}$ are each independently selected from the group consisting of carbon and nitrogen;

wherein at least one of $Z^1$, $Z^2$, $Z^3$, $Z^4$, $Z^5$, $Z^6$, $Z^7$ and $Z^8$ is nitrogen; at least one of $Z^9$, $Z^{10}$, $Z^{11}$, $Z^{12}$, $Z^{13}$, $Z^{14}$, $Z^{15}$, $Z^{16}$, $Z^{17}$, $Z^{18}$, $Z^{19}$ and $Z^{20}$ is nitrogen; at least one of $Z^1$, $Z^2$, $Z^3$ and $Z^4$ is carbon; and at least one of $Z^9$, $Z^{10}$, $Z^{11}$ and $Z^{12}$ is carbon;

wherein when any of $Z^1$ to $Z^{32}$ is nitrogen, there is no substitution on that nitrogen;

wherein $R^1$, $R^4$, $R^6$, $R^7$ and $R^{10}$ each independently represent mono, di, tri or tetra substitution, or no substitution;

wherein $R^3$, $R^5$, $R^8$, $R^9$ and $R^{11}$ each independently represent mono, di or tri substitution, or no substitution;

wherein $R^2$ represents mono substitution, or no substitution;

wherein $R^{12}$ represents mono, di, tri, tetra or penta substitution, or no substitution;

wherein $Ar^1$ is selected from the group consisting of benzene, biphenyl, terphenyl, triphenylene, fluorene, pyridine, pyrimidine, triazine, and combinations thereof;

wherein X is selected from the group consisting of O, S, and Se; and wherein L and $Ar^1$ are each optionally further substituted with one or more substituents selected from the group consisting of deuterium, alkyl, alkoxyl, halogen, silyl, nitro, benzene, biphenyl, terphenyl, naphthalene, phenanthrene, dibenzofuran, dibenzothiophene, dibenzoselenophene, fluorene, triphenylene, pyridine, pyrimidine, pyrazine, pyridazine, triazine, quinoline, phenanthroline, aza-dibenzofuran, aza-dibenzothiophene, aza-dibenzoselenophene, aza-fluorene and aza-triphenylene, and combinations thereof.

In one embodiment, the compound is selected from the group consisting of:

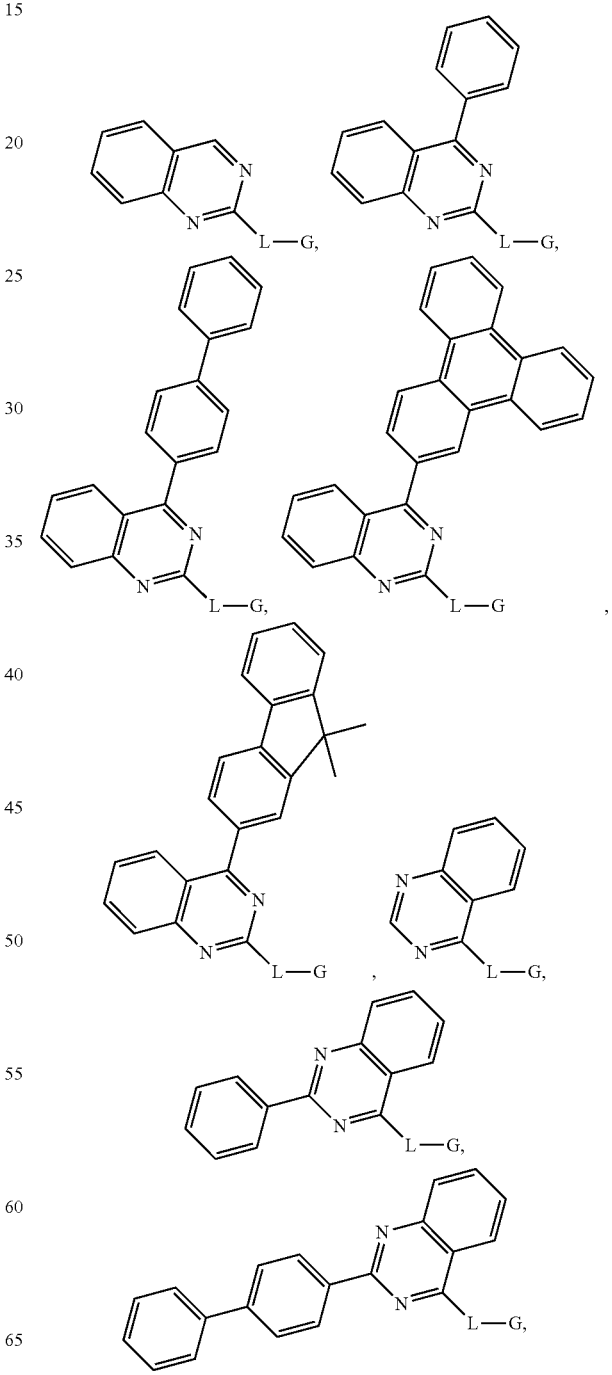

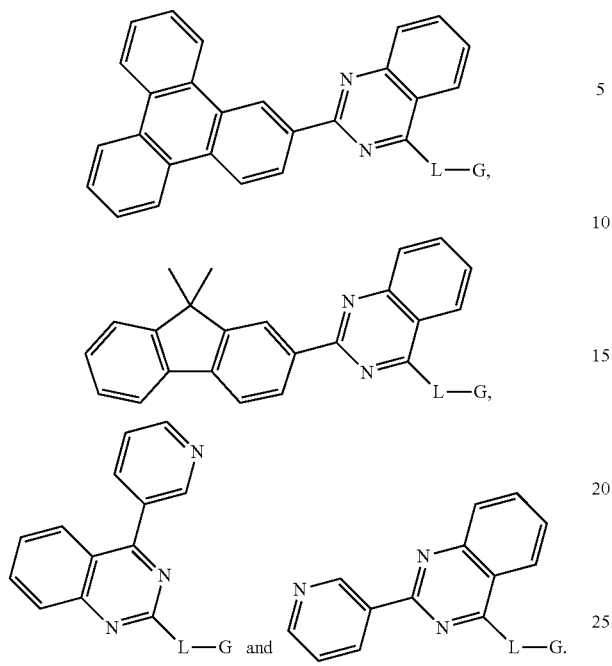
In one embodiment, the compound is selected from the group consisting of:
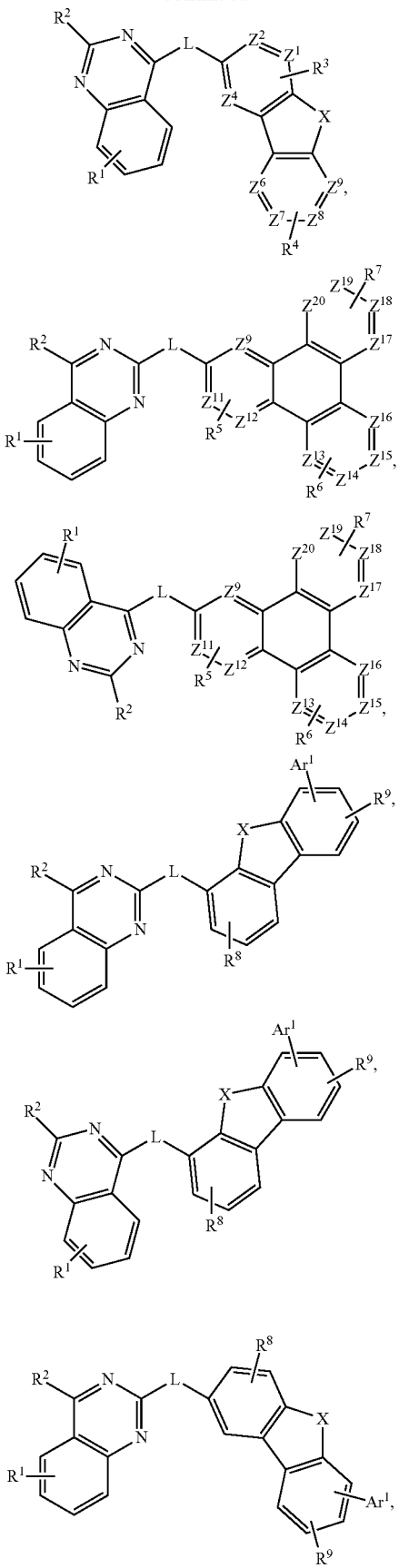

-continued
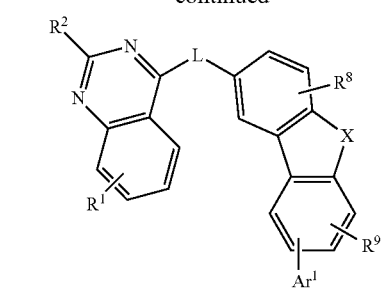
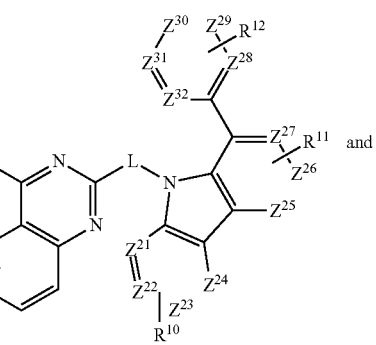
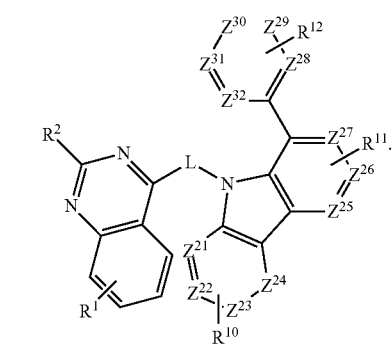
In one embodiment, G is selected from the group consisting of:
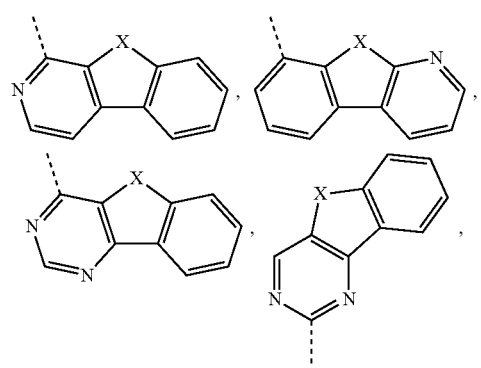
-continued
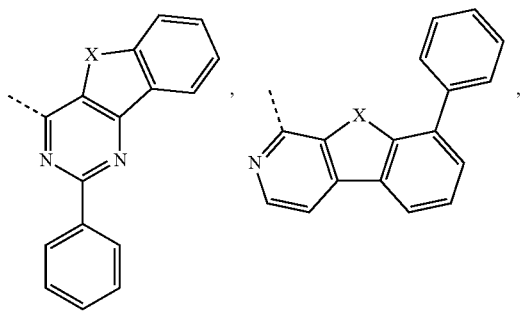
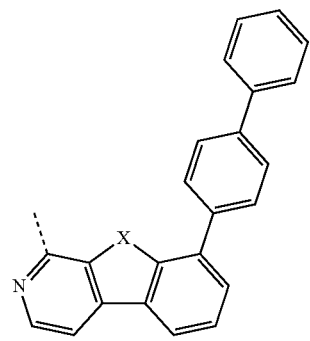
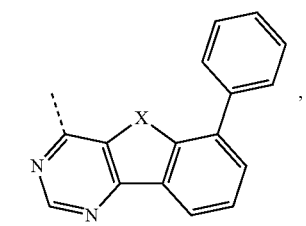
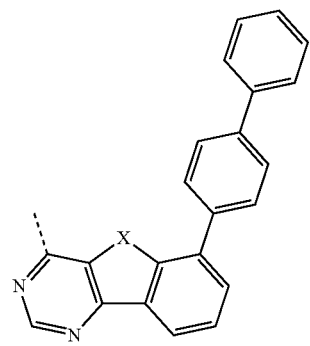
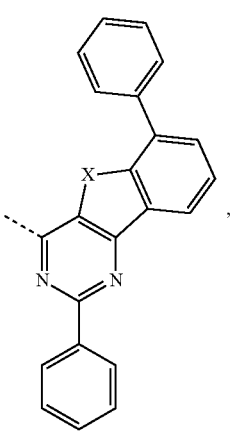

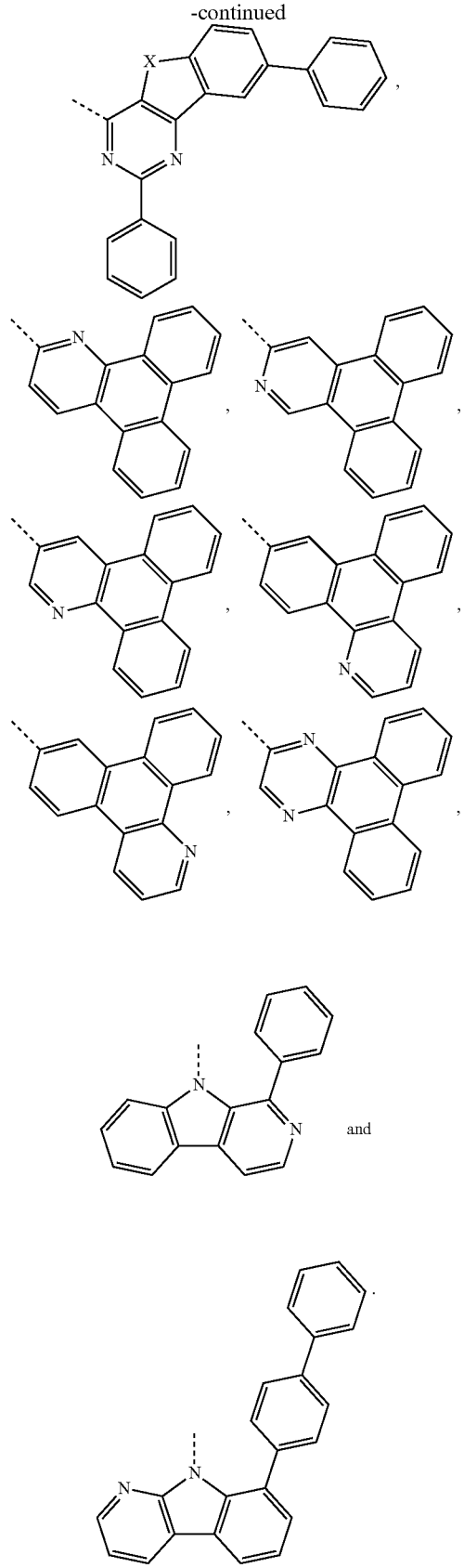
In one embodiment, L is selected from the group consisting of:
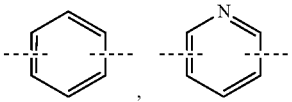
direct bond,
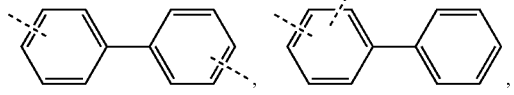
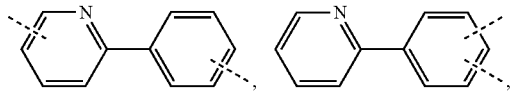
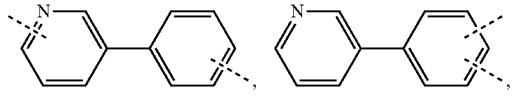
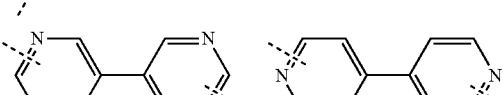
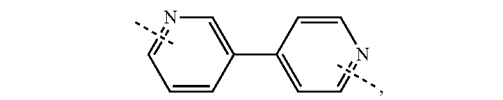
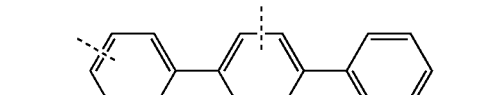
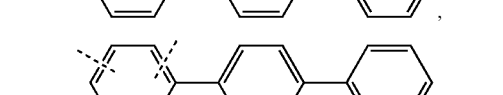
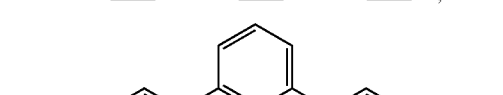
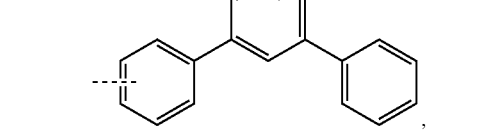

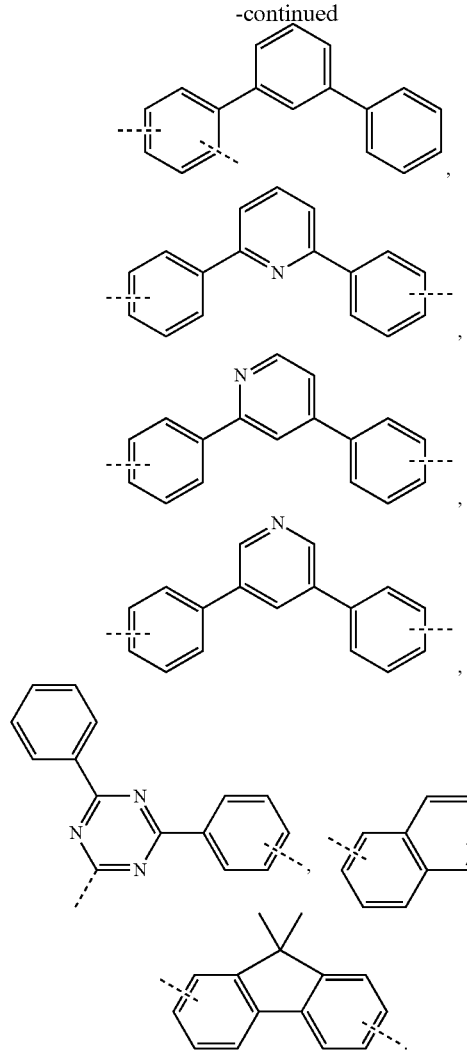
In one embodiment, the compound is selected from the group consisting of:
Compound A1
Compound A2
Compound A3
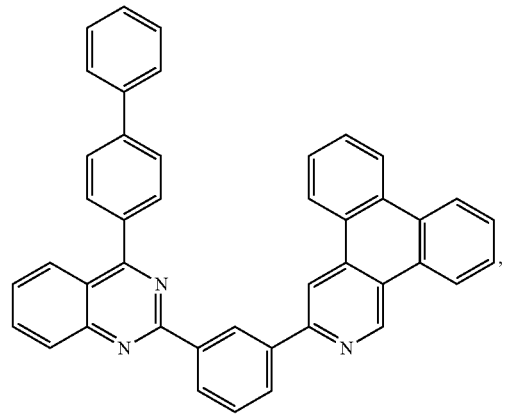
Compound B1
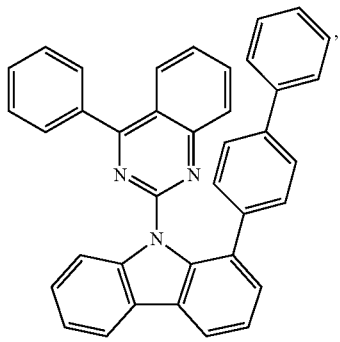
Compound B2
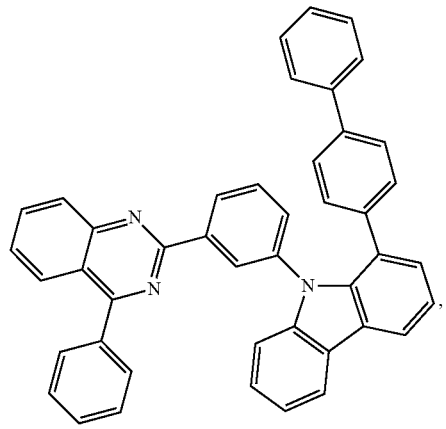
Compound B3
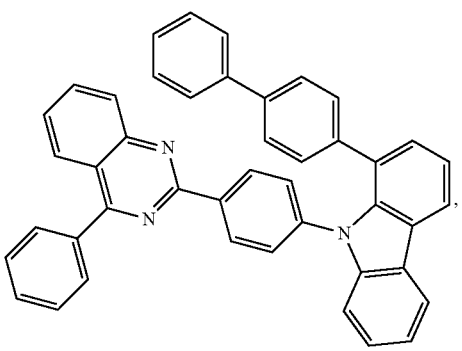

-continued
Compound B4
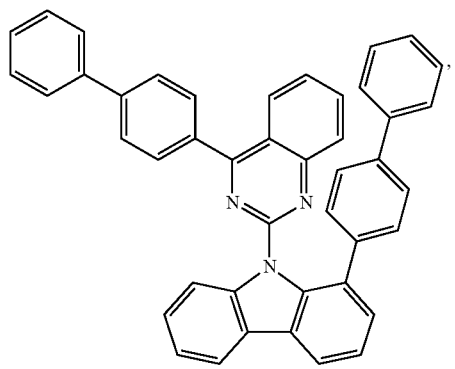
Compound B5
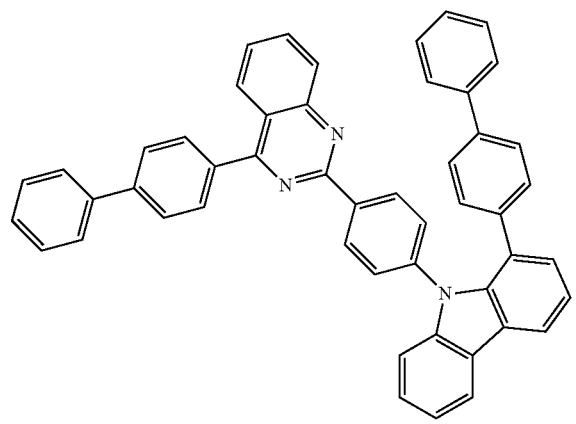
Compound B6
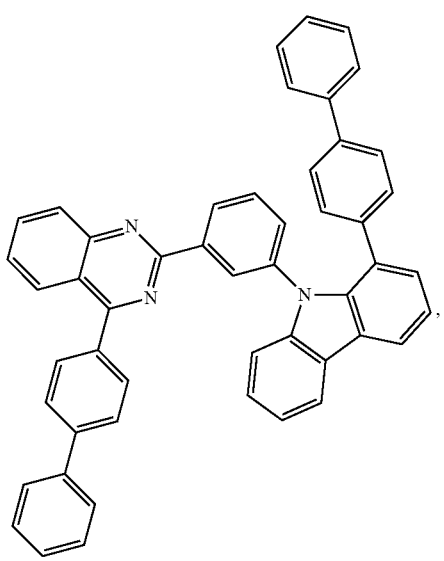
Compound B7
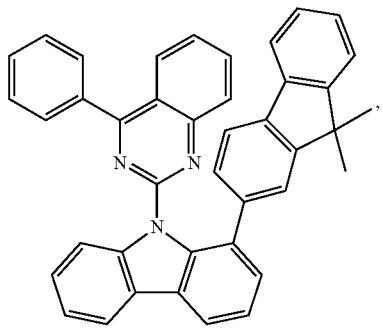
Compound B8
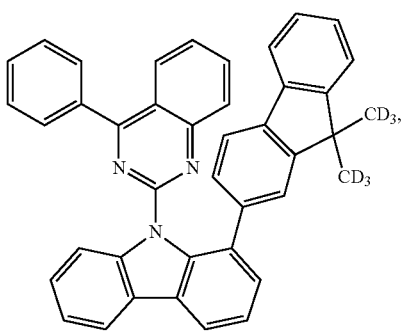
Compound B9
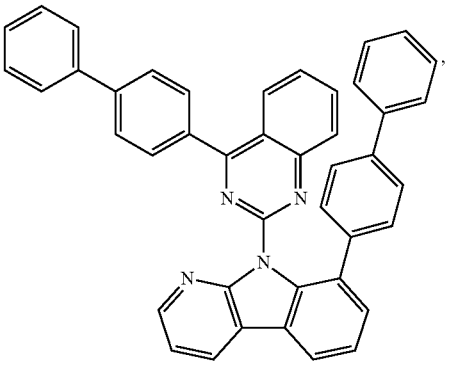
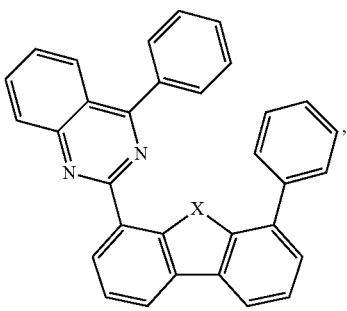
Compound C1, X is O;
Compound C2, X is S;
Compound C3, X is Se.

-continued

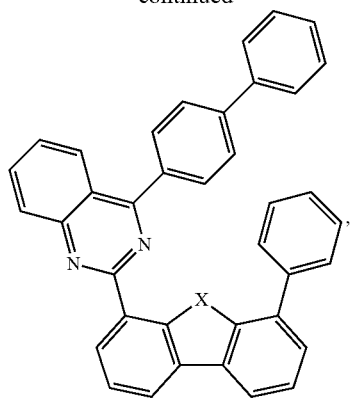

Compound C4, X is O;
Compound C5, X is S;
Compound C6, X is Se.

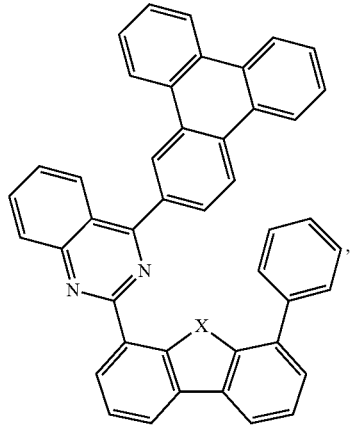

Compound C7, X is O;
Compound C8, X is S;
Compound C9, X is Se.

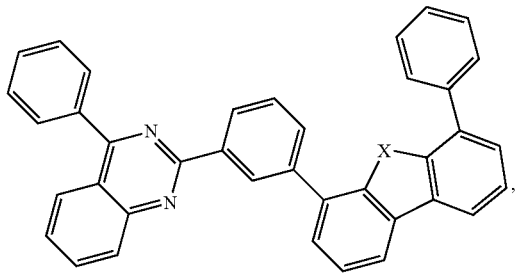

Compound C10, X is O;
Compound C11, X is S;
Compound C12, X is Se.

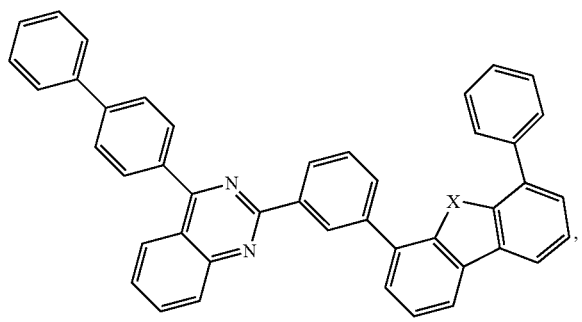

Compound C13, X is O;
Compound C14, X is S;
Compound C15, X is Se.

-continued

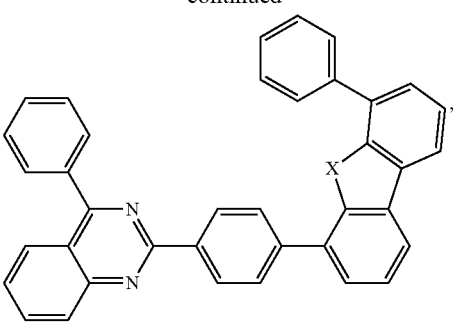

Compound C16, X is O;
Compound C17, X is S;
Compound C18, X is Se.

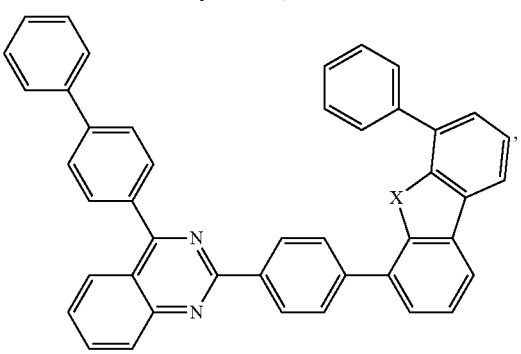

Compound C19, X is O;
Compound C20, X is S;
Compound C21, X is Se.

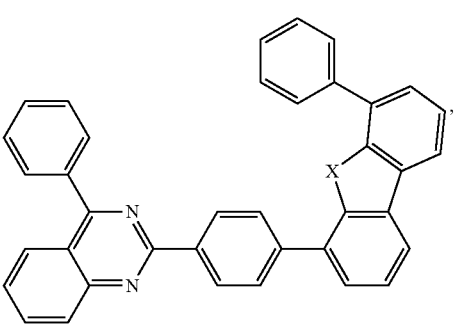

Compound C22, X is O;
Compound C23, X is S;
Compound C24, X is Se.

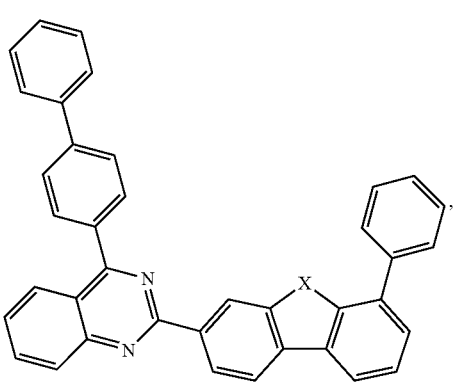

Compound C25, X is O;
Compound C26, X is S;
Compound C27, X is Se.

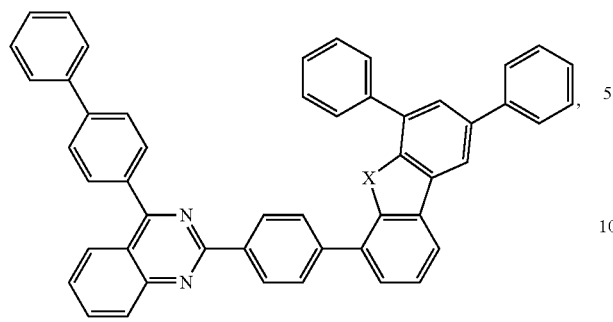
Compound C28, X is O;
Compound C29, X is S;
Compound C30, X is Se.
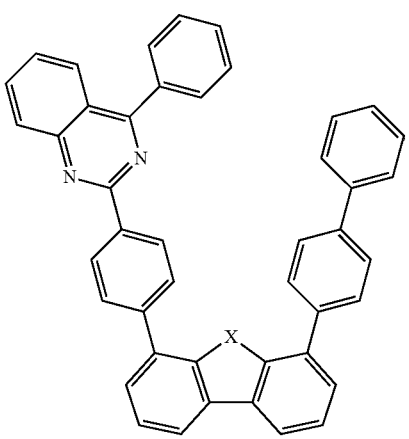
Compound C37, X is O;
Compound C38, X is S;
Compound C39, X is Se.
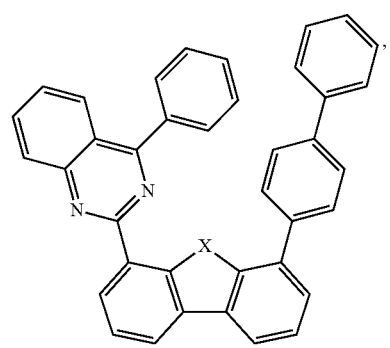
Compound C31, X is O;
Compound C32, X is S;
Compound C33, X is Se.
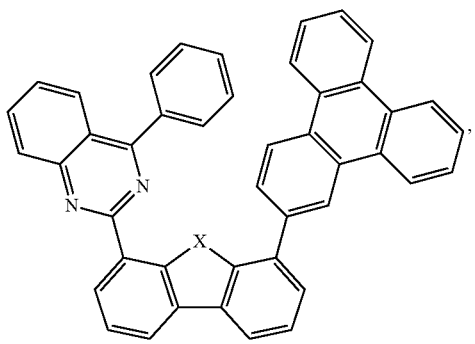
Compound C40, X is O;
Compound C41, X is S;
Compound C42, X is Se.
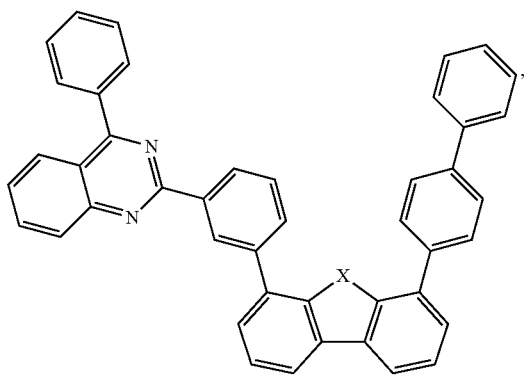
Compound C34, X is O;
Compound C35, X is S;
Compound C36, X is Se.
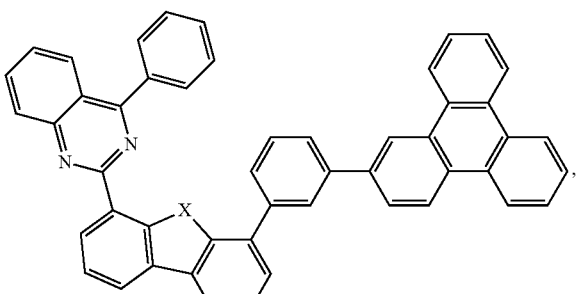
Compound C43, X is O;
Compound C44, X is S;
Compound C45, X is Se.

-continued
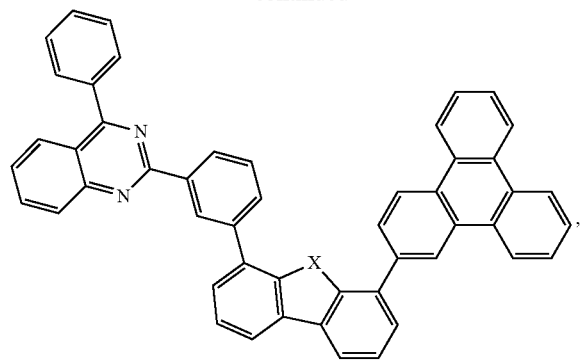
Compound C46, X is O;
Compound C47, X is S;
Compound C48, X is Se.
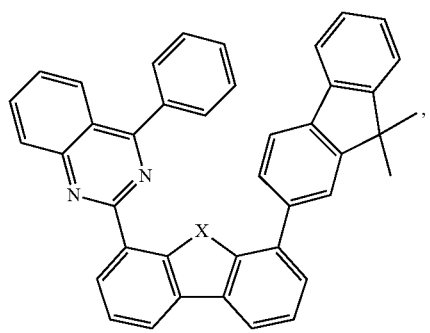
Compound C49, X is O;
Compound C50, X is S;
Compound C51, X is Se.
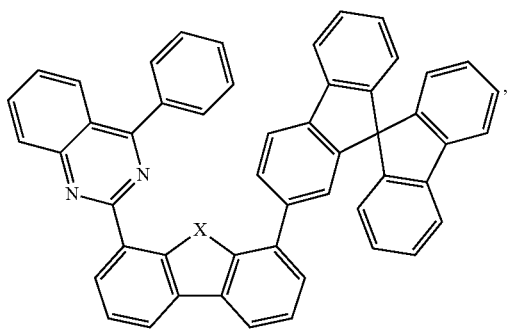
Compound C52, X is O;
Compound C53, X is S;
Compound C54, X is Se.
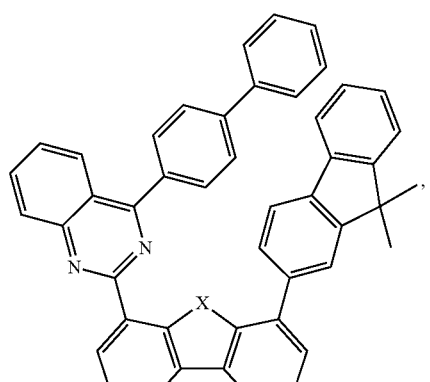
Compound C55, X is O;
Compound C56, X is S;
Compound C57, X is Se.
-continued
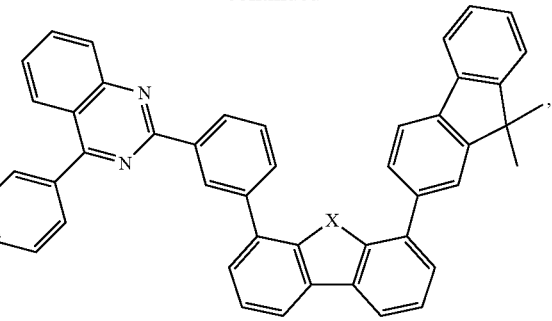
Compound C58, X is O;
Compound C59, X is S;
Compound C60, X is Se.
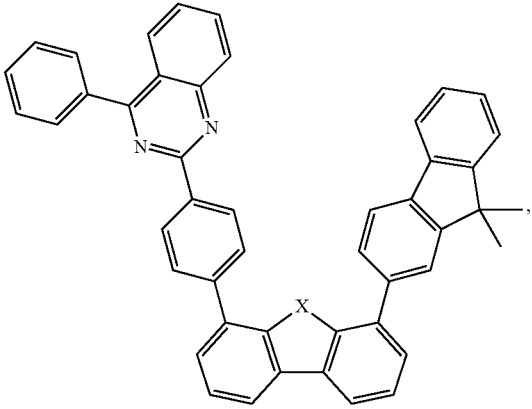
Compound C61, X is O;
Compound C62, X is S;
Compound C63, X is Se.
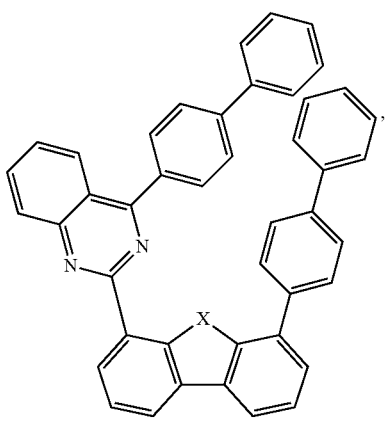
Compound C64, X is O;
Compound C65, X is S;
Compound C66, X is Se.

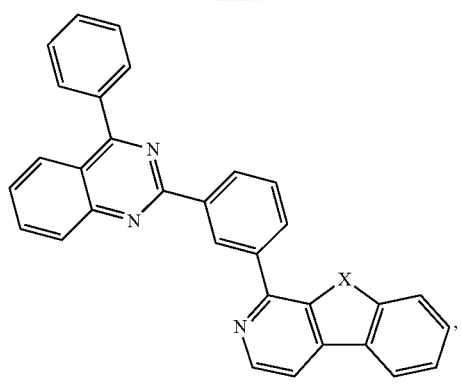

Compound D1, X is O;
Compound D2, X is S;
Compound D3, X is Se.

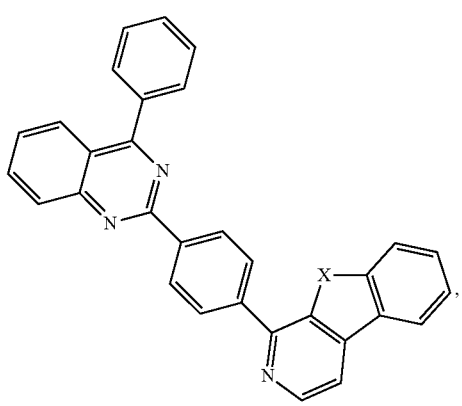

Compound D4, X is O;
Compound D5, X is S;
Compound D6, X is Se.

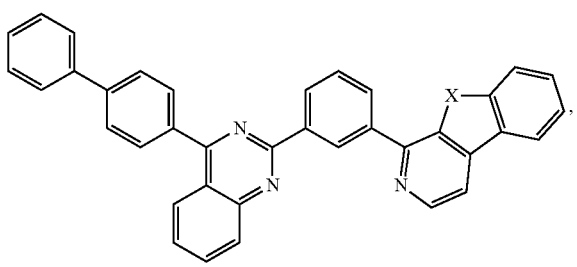

Compound D7, X is O;
Compound D8, X is S;
Compound D9, X is Se.

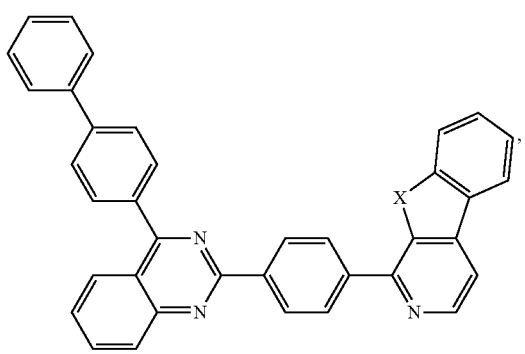

Compound D10, X is O;
Compound D11, X is S;
Compound D12, X is Se.

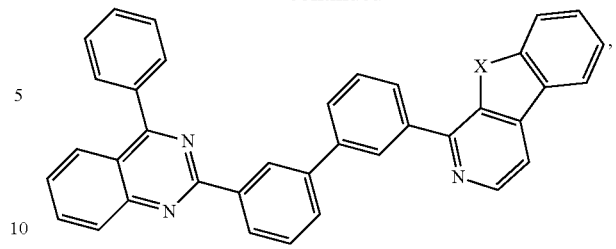

Compound D13, X is O;
Compound D14, X is S;
Compound D15, X is Se.

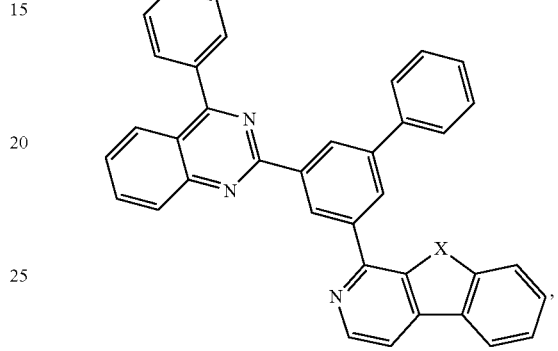

Compound D16, X is O;
Compound D17, X is S;
Compound D18, X is Se.

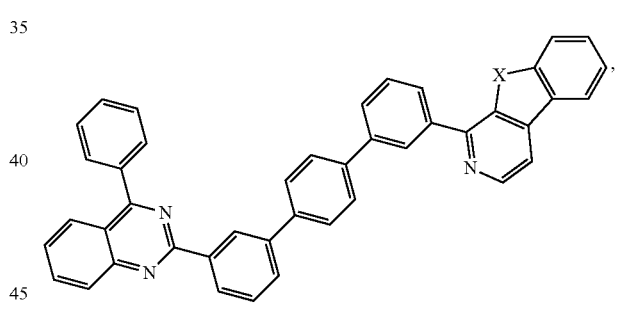

Compound D19, X is O;
Compound D20, X is S;
Compound D21, X is Se.

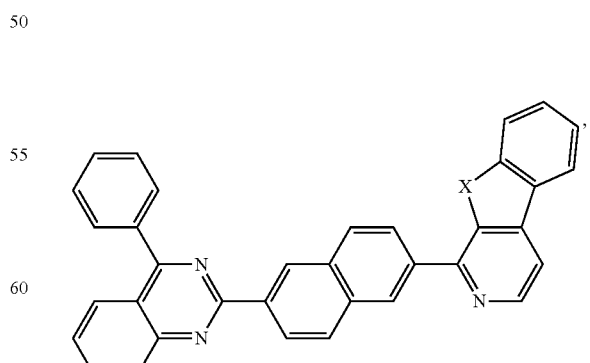

Compound D22, X is O;
Compound D23, X is S;
Compound D23, X is Se.

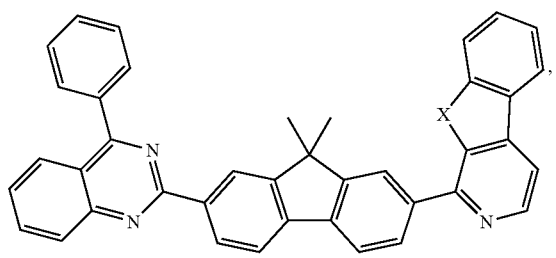

Compound D25, X is O;
Compound D26, X is S;
Compound D27, X is Se.

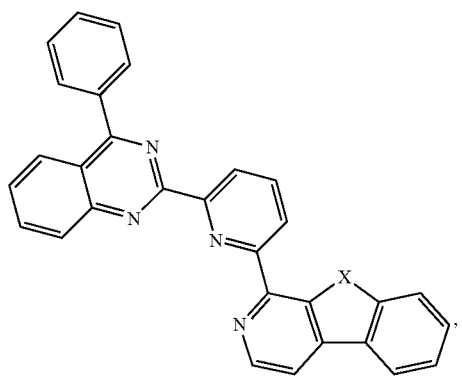

Compound D28, X is O;
Compound D29, X is S;
Compound D30, X is Se.

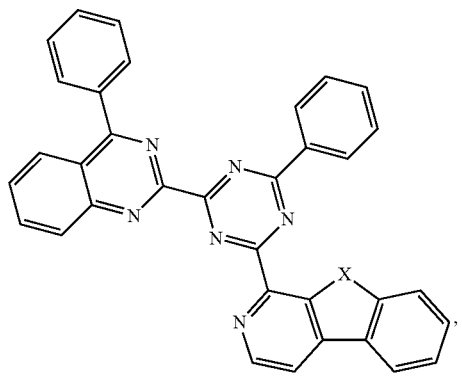

Compound D31, X is O;
Compound D32, X is S;
Compound D33, X is Se.

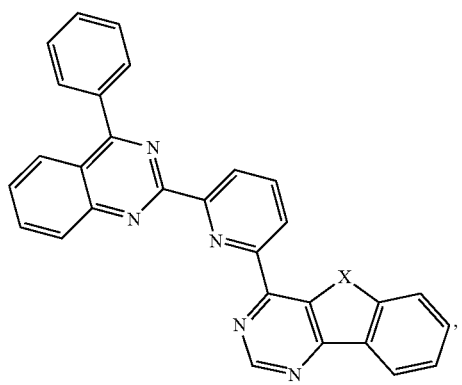

Compound D34, X is O;
Compound D35, X is S;
Compound D36, X is Se.

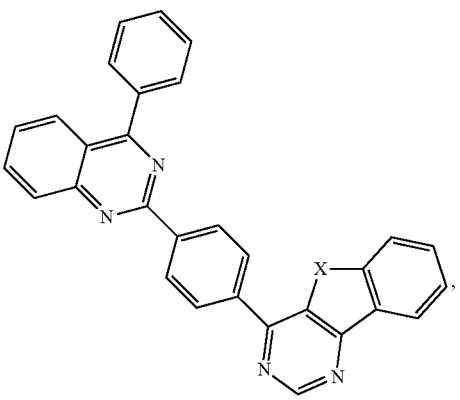

Compound D37, X is O;
Compound D38, X is S;
Compound D39, X is Se.

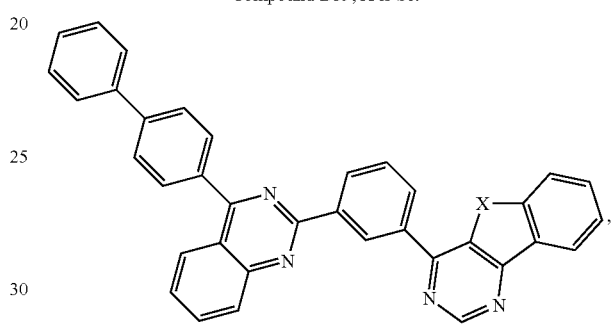

Compound D40, X is O;
Compound D41, X is S;
Compound D42, X is Se.

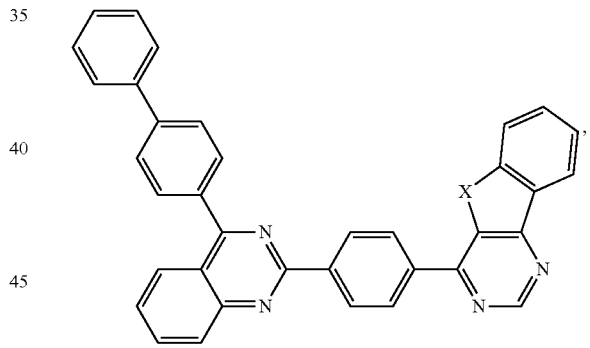

Compound D43, X is O;
Compound D44, X is S;
Compound D45, X is Se.

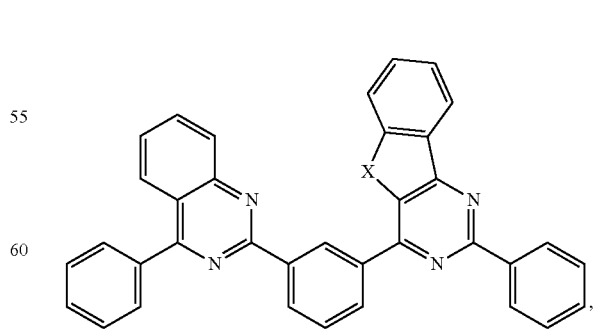

Compound D46, X is O;
Compound D47, X is S;
Compound D48, X is Se.

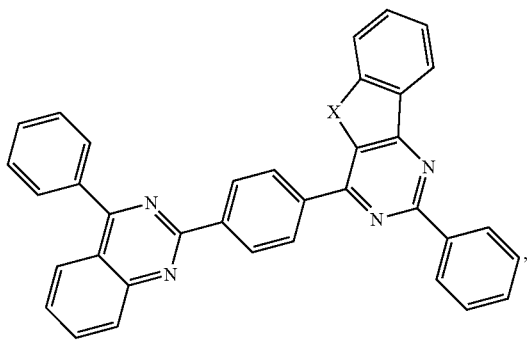

Compound D49, X is O;
Compound D50, X is S;
Compound D51, X is Se.

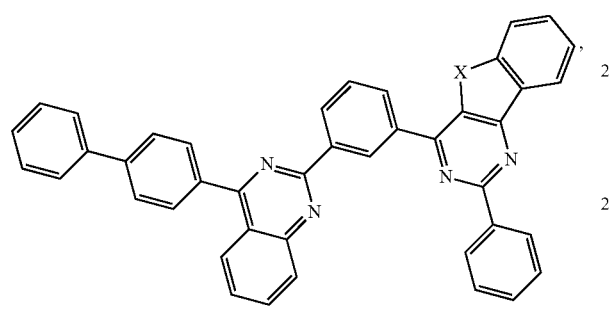

Compound D52, X is O;
Compound D53, X is S;
Compound D54, X is Se.

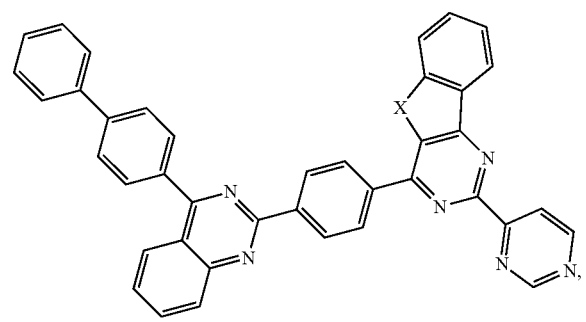

Compound D55, X is O;
Compound D56, X is S;
Compound D57, X is Se.

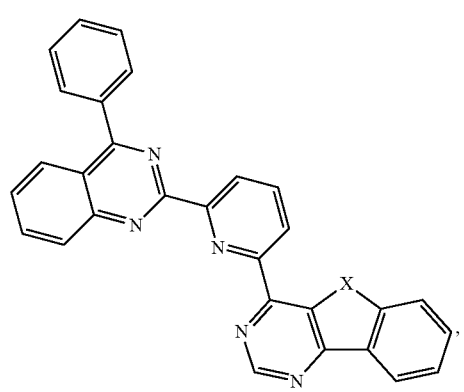

Compound D58, X is O;
Compound D59, X is S;
Compound D60, X is Se.

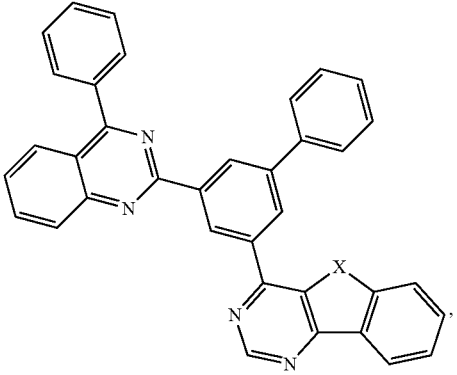

Compound D61, X is O;
Compound D62, X is S;
Compound D63, X is Se.

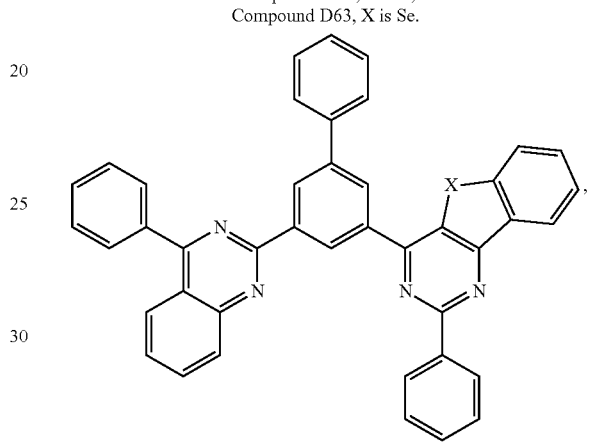

Compound D64, X is O;
Compound D65, X is S;
Compound D66, X is Se.

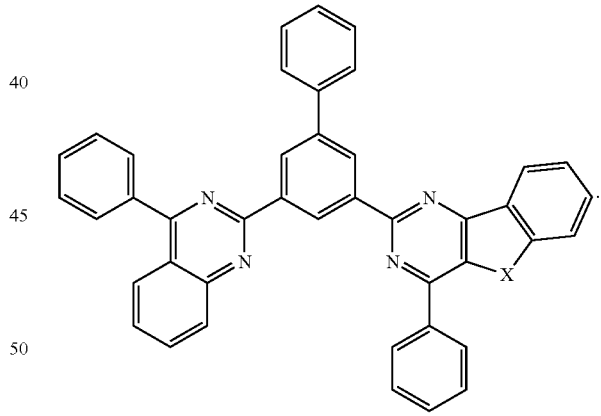

Compound D67, X is O;
Compound D68, X is S;
Compound D69, X is Se.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence), triplet-triplet annihilation, or combinations of these processes.

According to another aspect of the present disclosure, an OLED is also provided. The OLED includes an anode, a cathode, and an organic layer disposed between the anode and the cathode. The organic layer may include a host and a phosphorescent dopant. The organic layer can include a compound according to Formula I, and its variations as described herein.

The OLED can be incorporated into one or more of a consumer product, an electronic component module and a lighting panel. The organic layer can be an emissive layer and the compound can be a host in some embodiments.

The organic layer can also include an emissive dopant. In some embodiments, two or more emissive dopants are preferred. In one embodiment, the organic layer further comprises a phosphorescent emissive dopant. In some embodiments the emissive dopant is a transition metal complex having at least one ligand or part of the ligand if the ligand is more than bidentate selected from the group consisting of:

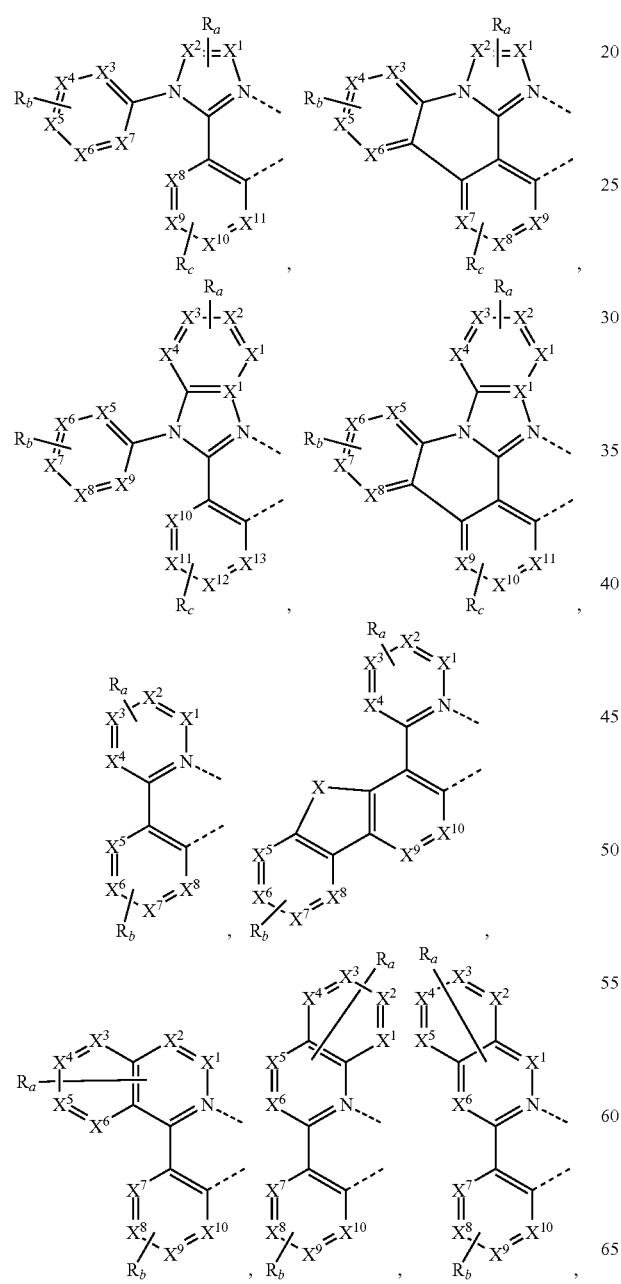

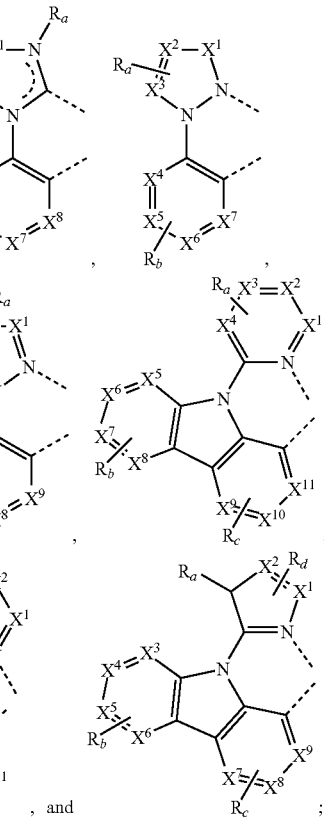

wherein each $X^1$ to $X^{13}$ are independently selected from the group consisting of carbon and nitrogen;

wherein X is selected from the group consisting of BR', NR', PR', O, S, Se, C=O, S=O, $SO_2$, CR'R", SiR'R", and GeR'R";

wherein R' and R" are optionally fused or joined to form a ring;

wherein each $R_a$, $R_b$, $R_c$ and $R_d$ may represent from mono substitution to the possible maximum number of substitution, or no substitution;

wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents of $R_a$, $R_b$, $R_c$ and $R_d$ are optionally fused or joined to form a ring or form a multidentate ligand.

Additional information on possible emissive dopants is provided below.

In some embodiments the organic layer is a blocking layer and the compound of Formula I is a blocking material in the organic layer. In other embodiments the organic layer is a transporting layer and the compound of Formula I is a transporting material in the organic layer.

In yet another aspect of the present disclosure, a formulation that comprises a compound according to Formula I is described. The formulation can include one or more components selected from the group consisting of a solvent, a host, a hole injection material, hole transport material, and an electron transport layer material, disclosed herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer. Non-limiting examples of the conductivity dopants that may be used in an OLED in combination with materials disclosed herein are exemplified below together with references that disclose those materials:

EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804 and US2012146012.

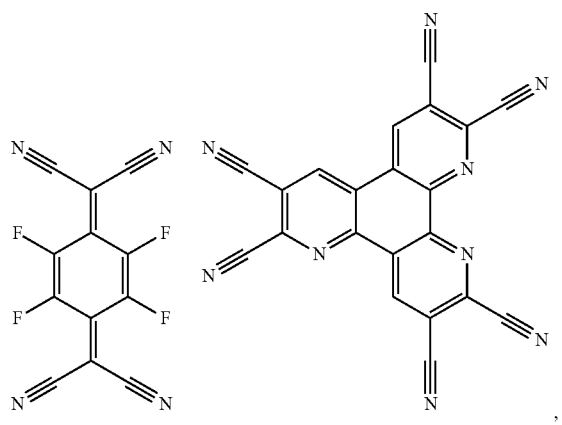

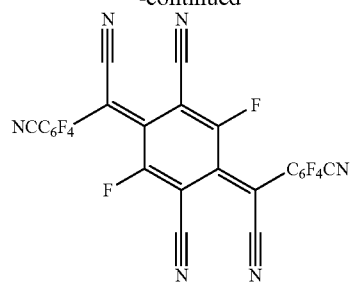

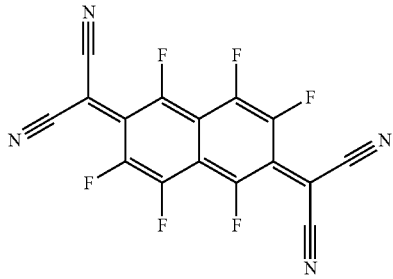

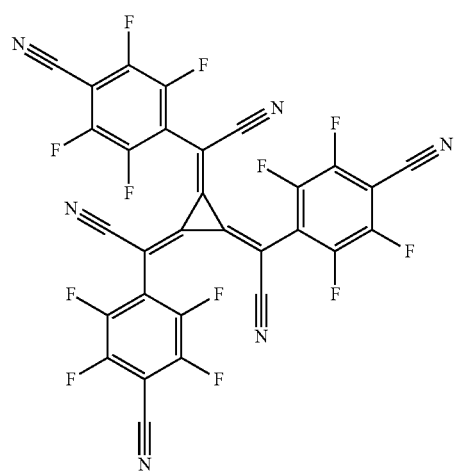

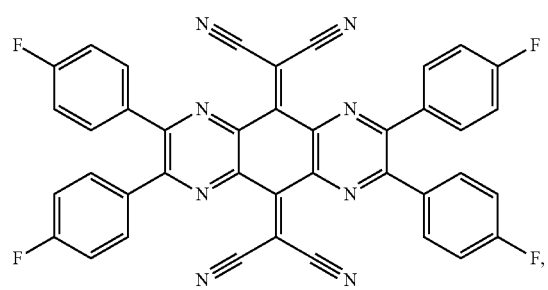

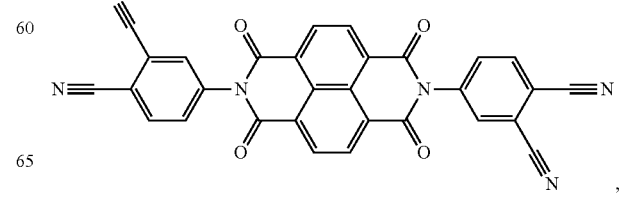

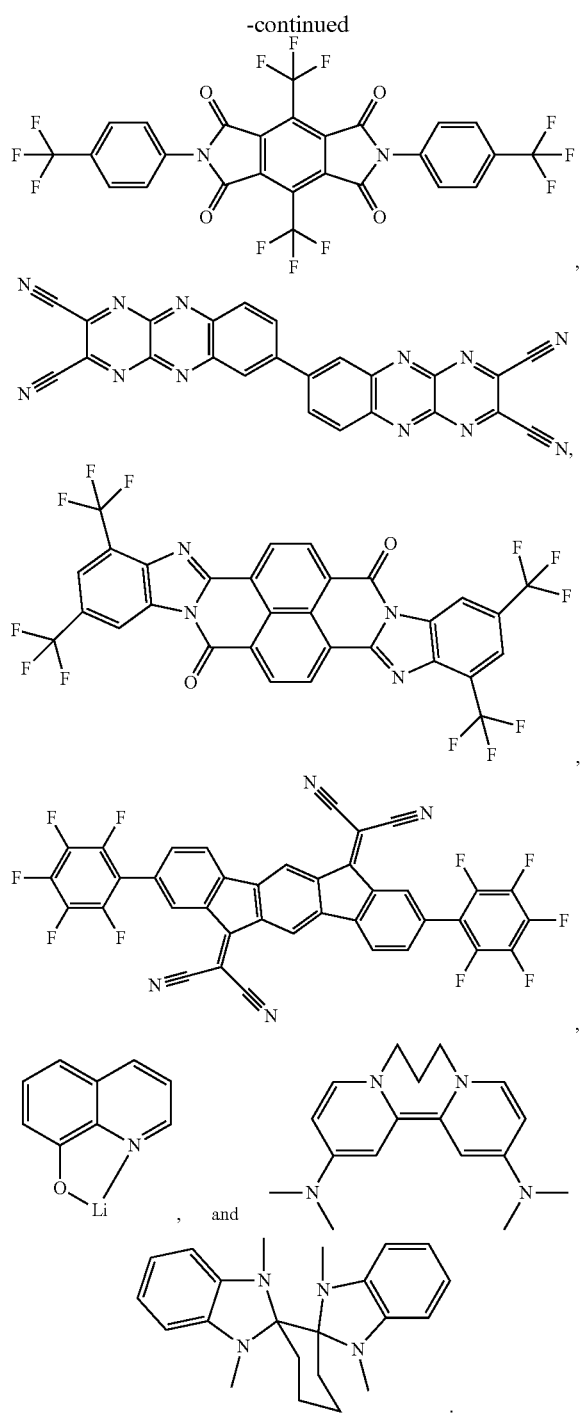

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphoric acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

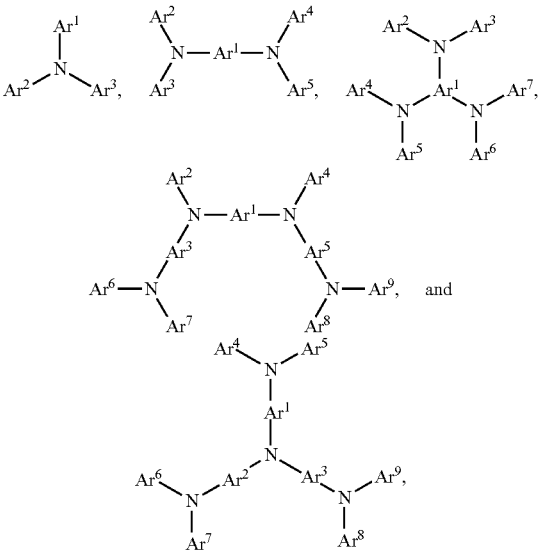

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

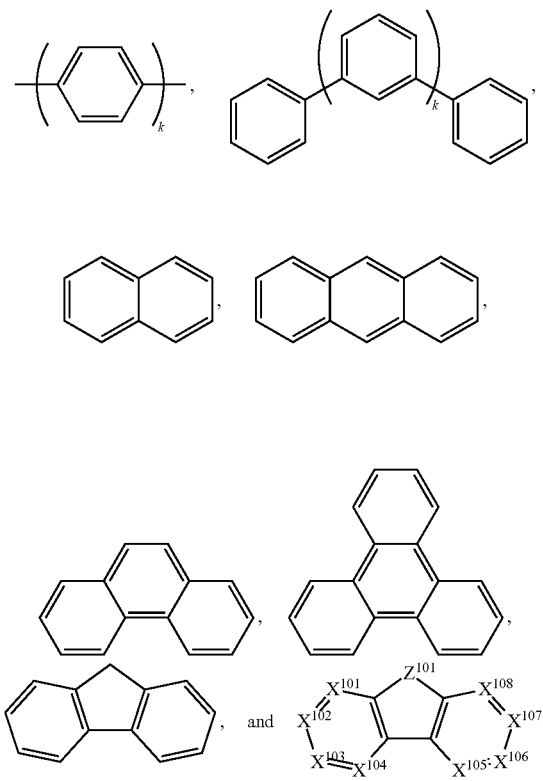

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

$$\left[ \left( \begin{array}{c} Y^{101} \\ Y^{102} \end{array} \right) Met - (L^{101})_{k''} \right]_{k'}$$

wherein Met is a metal, which can have an atomic weight greater than 40; $(Y^{101}\text{-}Y^2)$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative. In another aspect, $(Y^{101}\text{-}Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

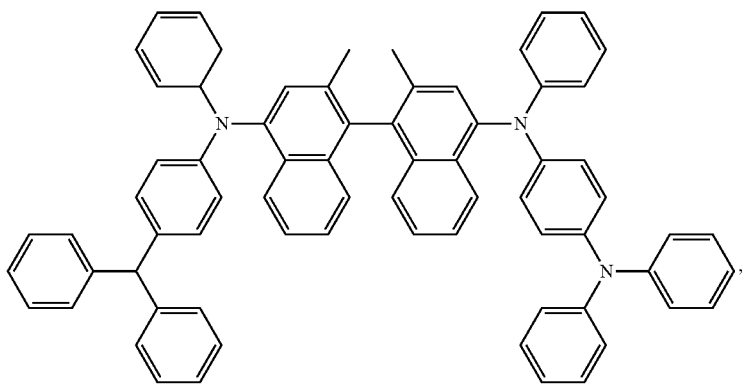

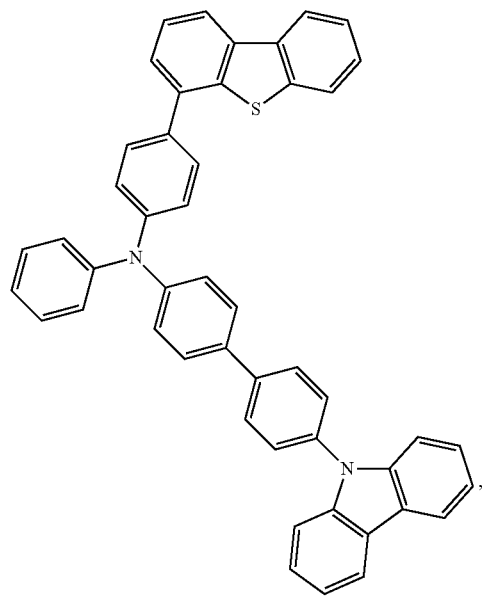
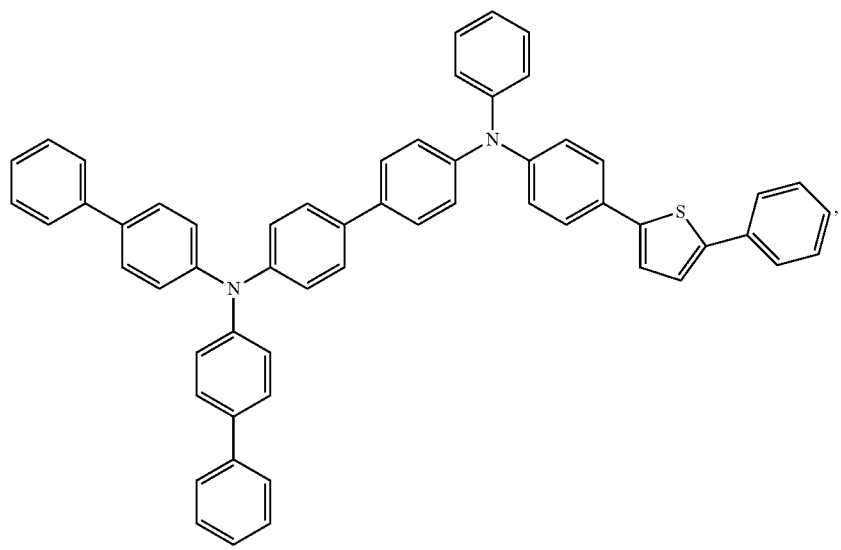
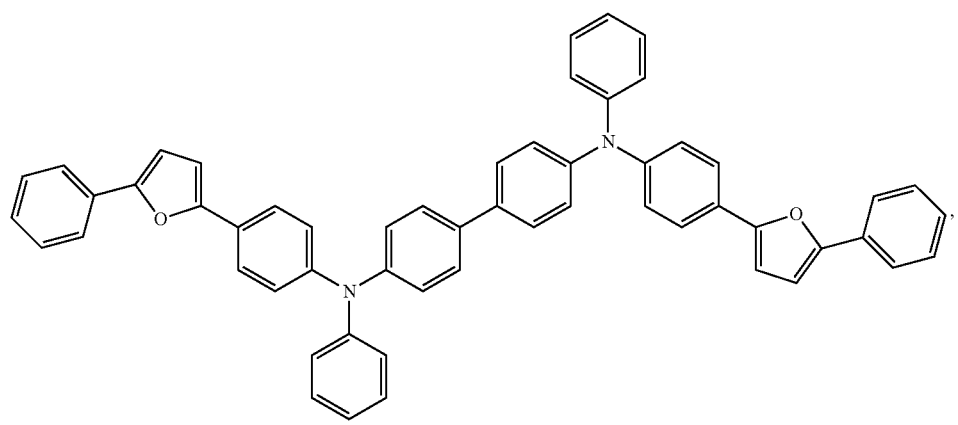

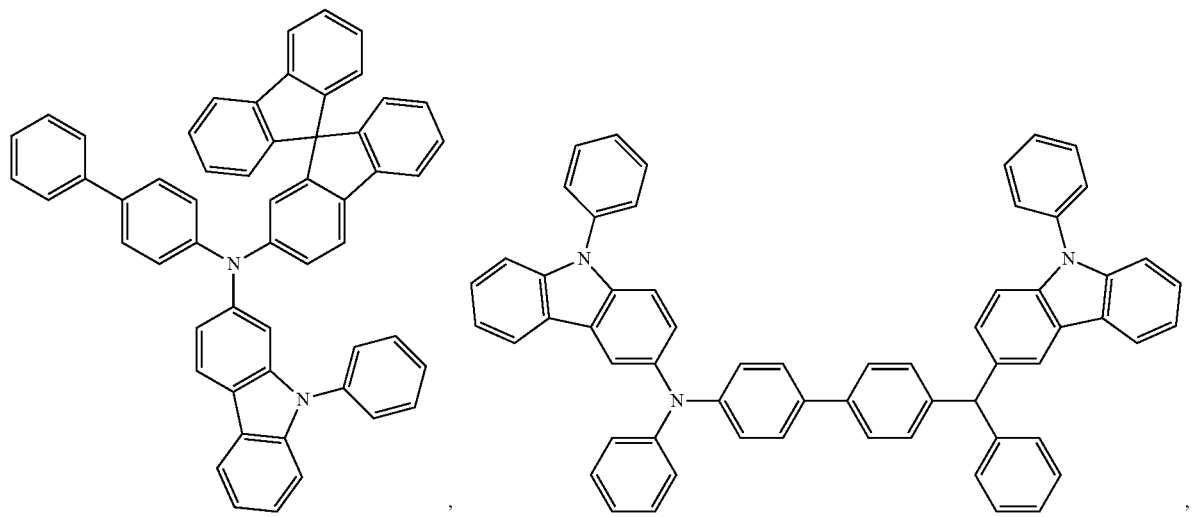
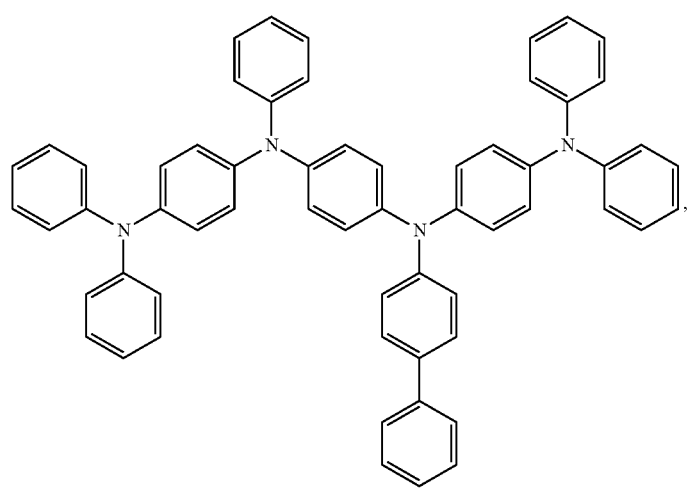
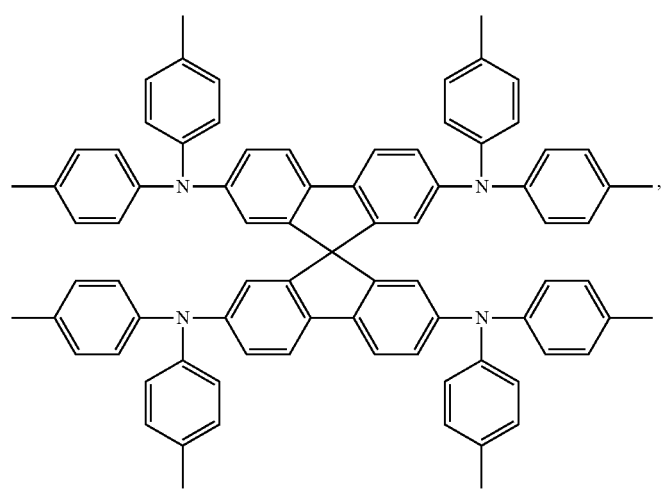

-continued
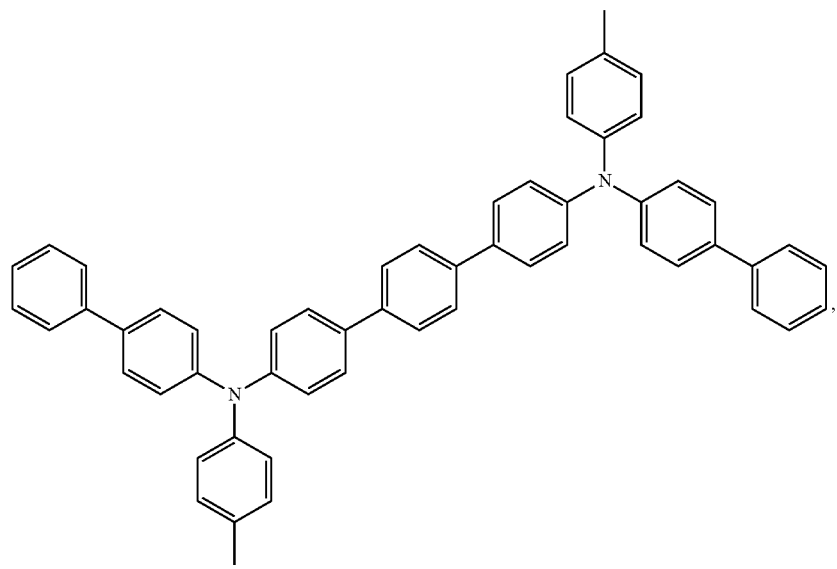
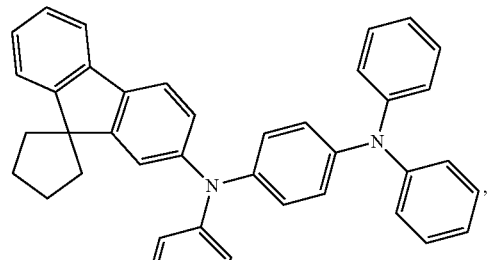
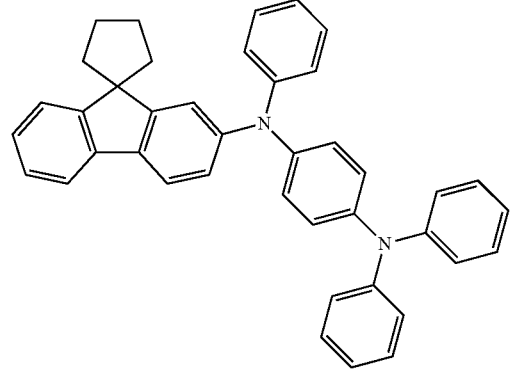
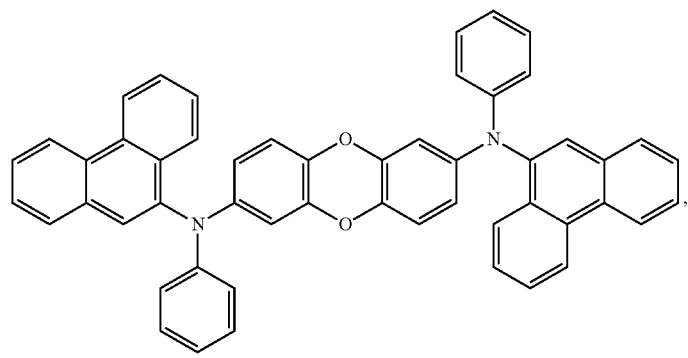

-continued
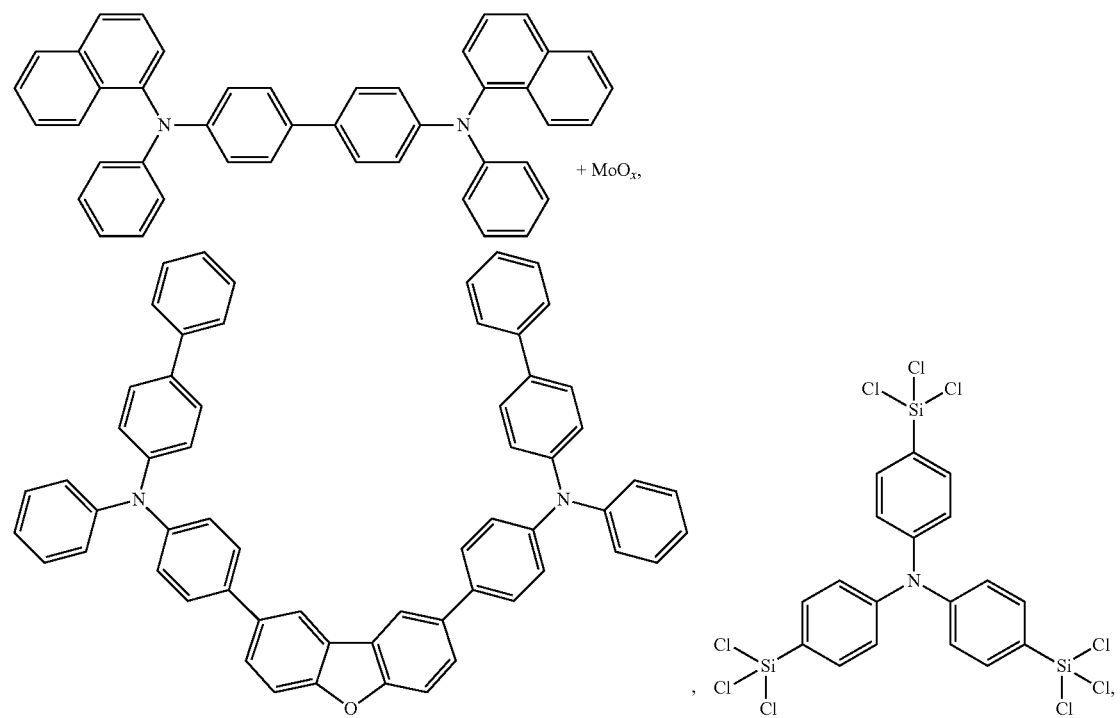
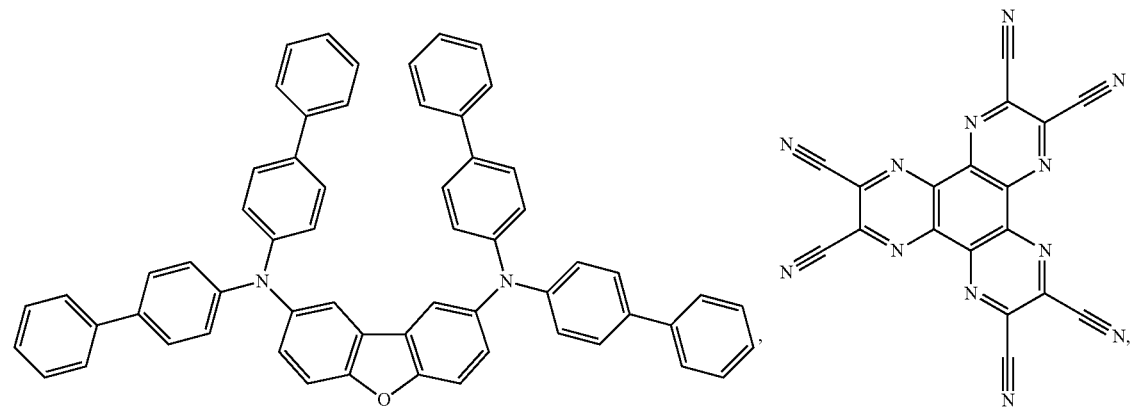
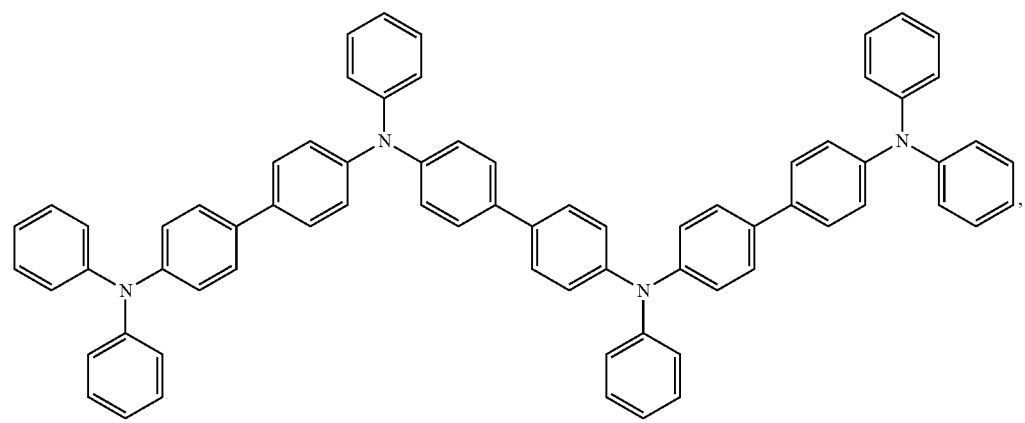

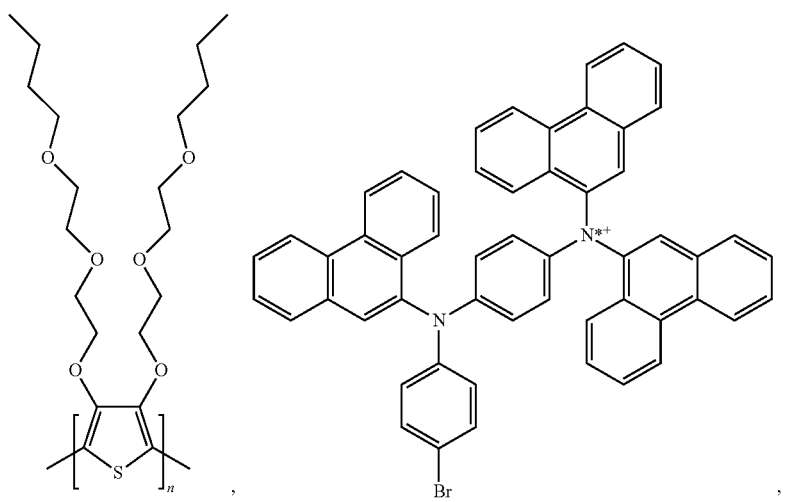
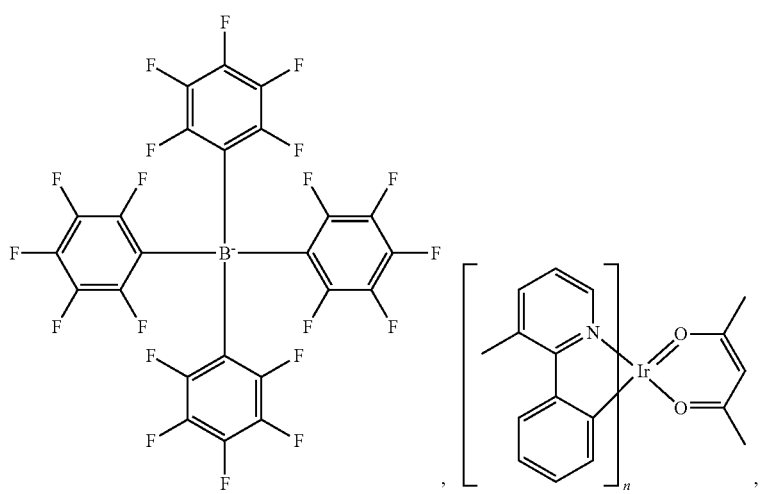
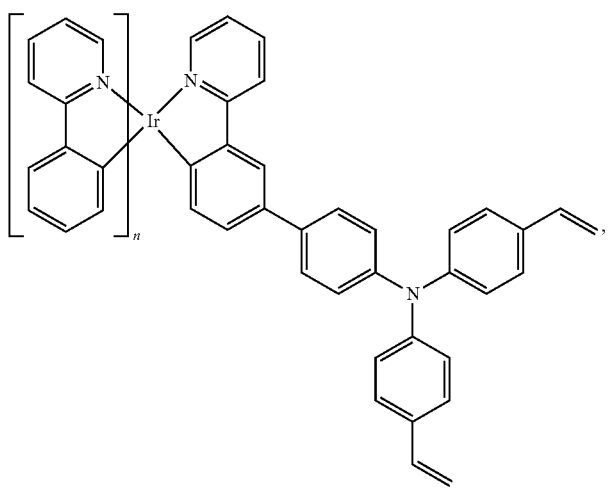

-continued
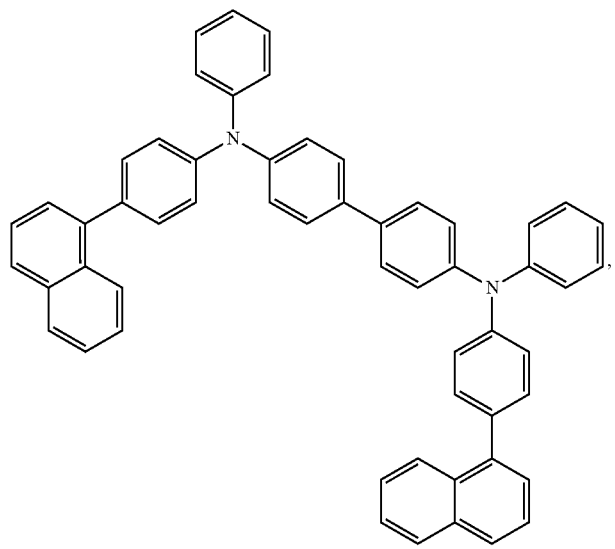
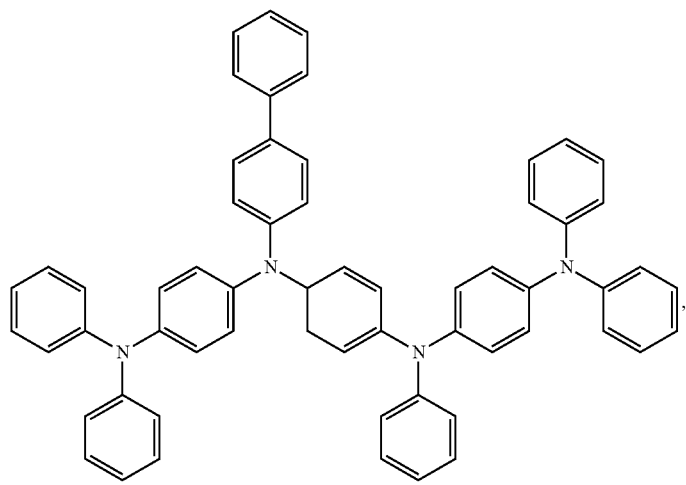
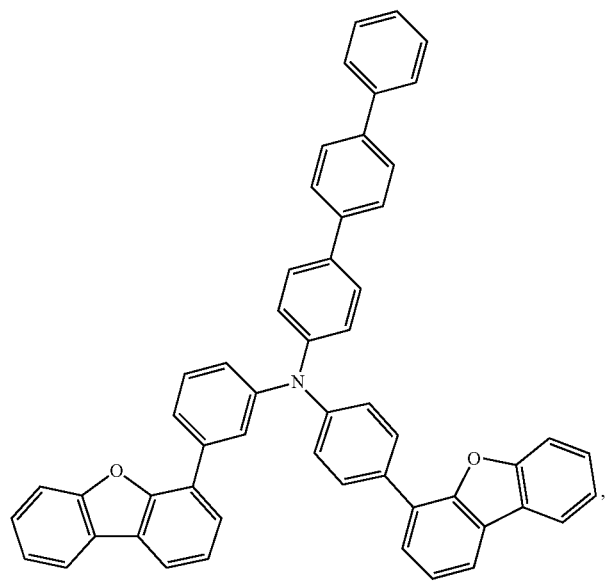

-continued
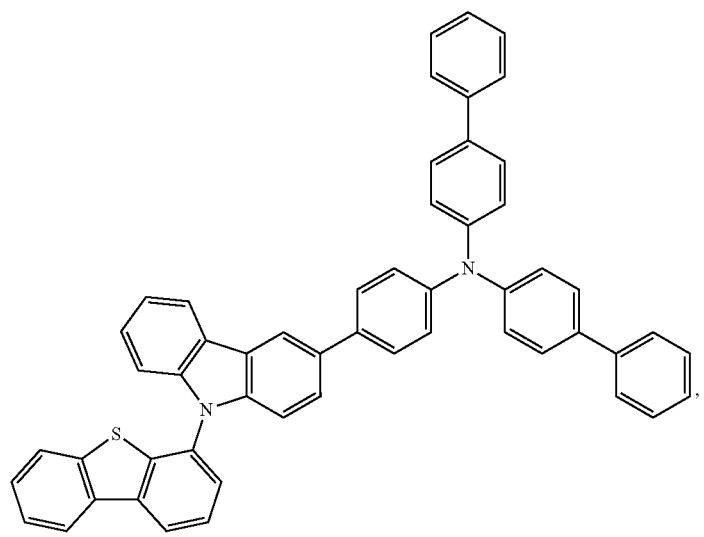
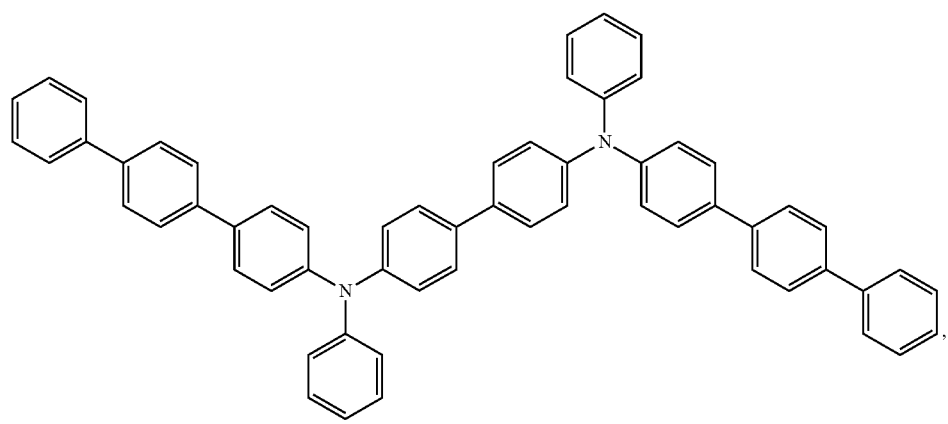
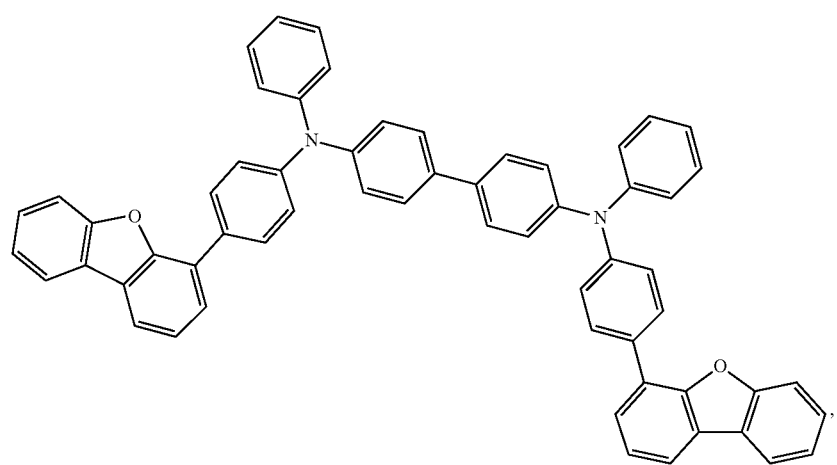

-continued
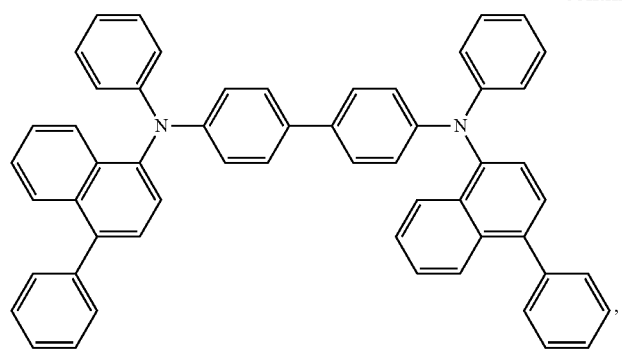
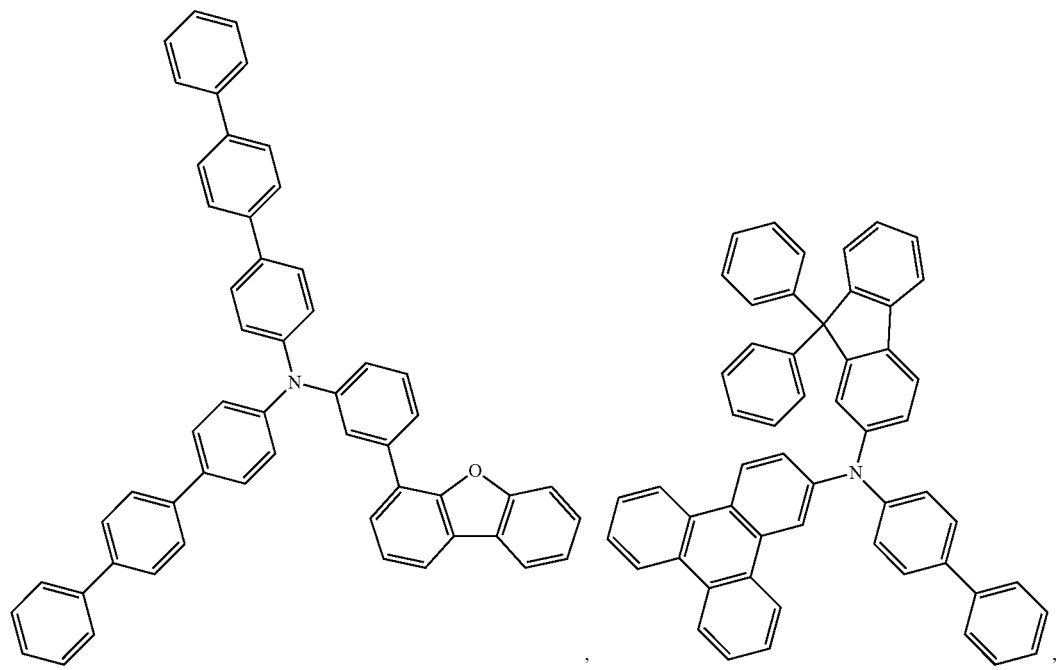
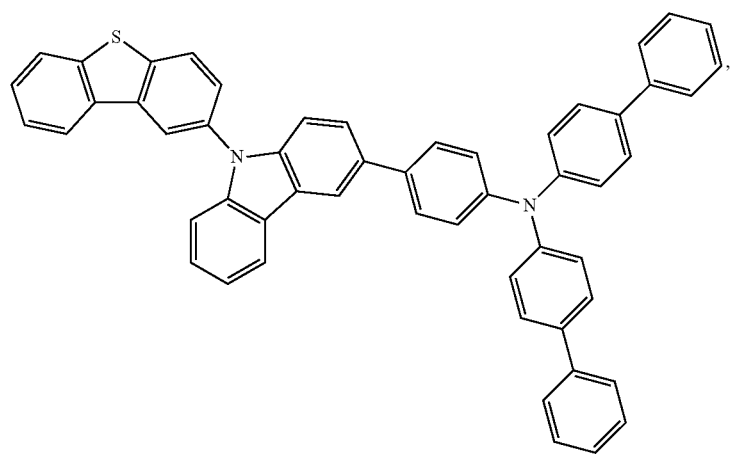

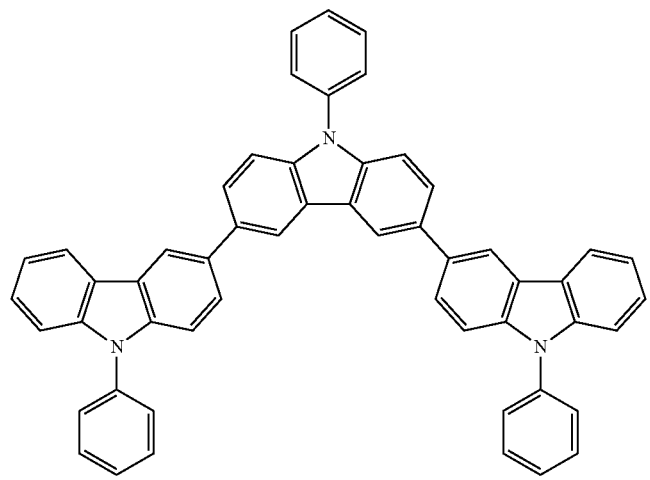
,
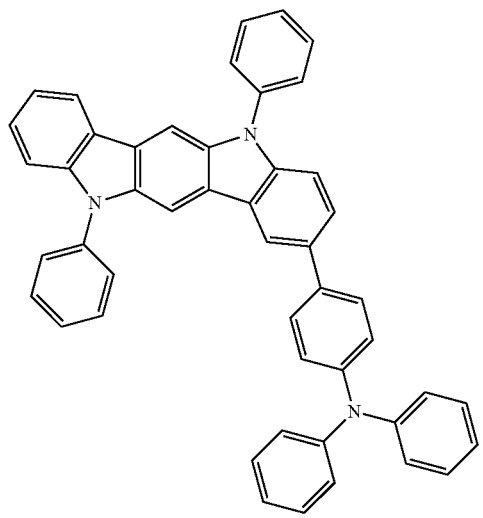
,
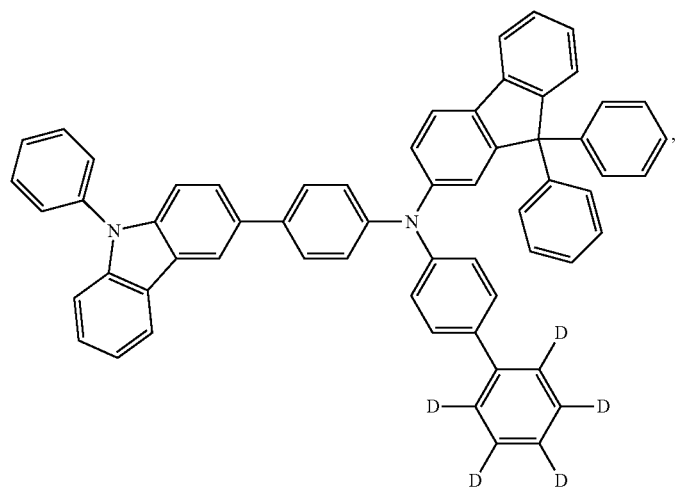
,
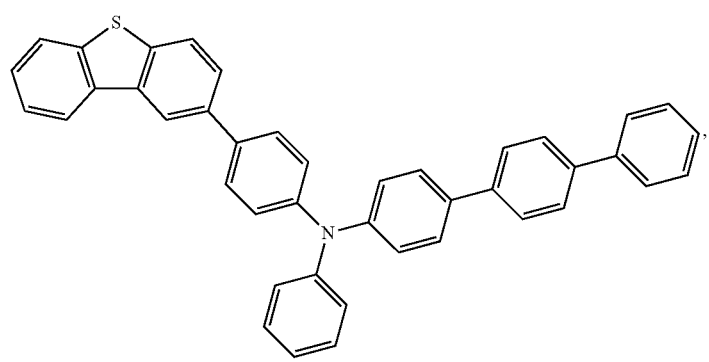
,

-continued
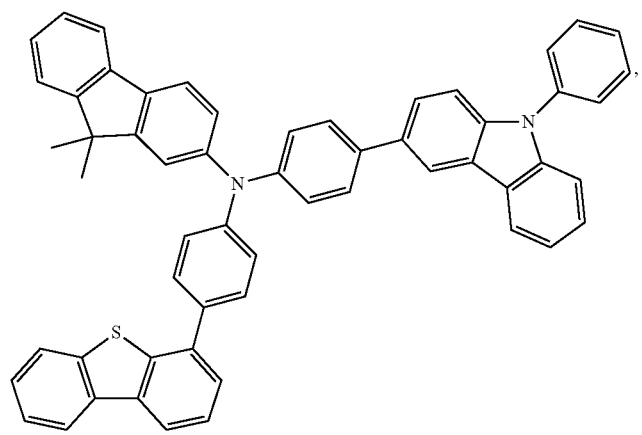
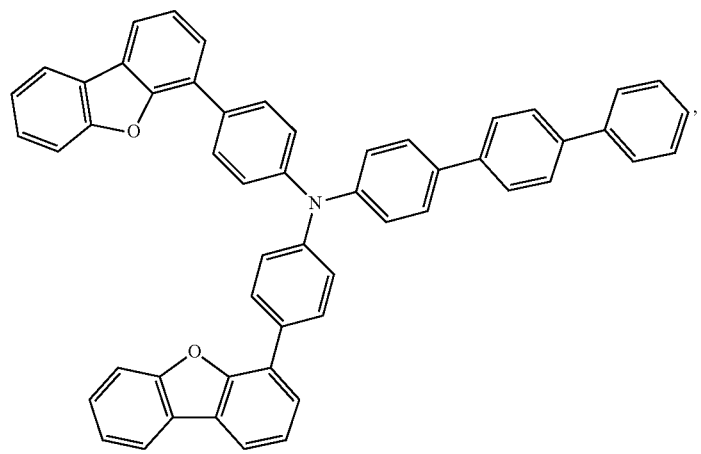
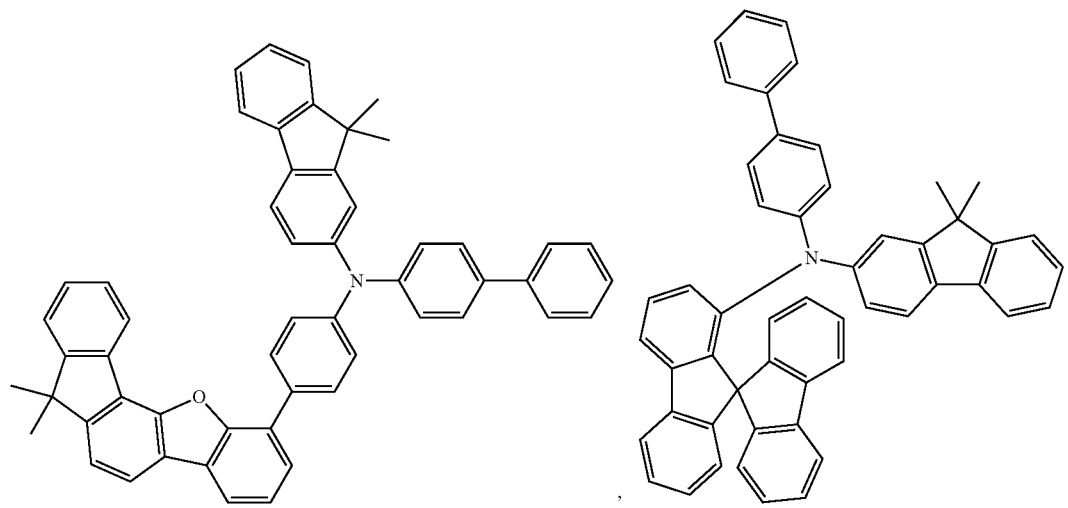

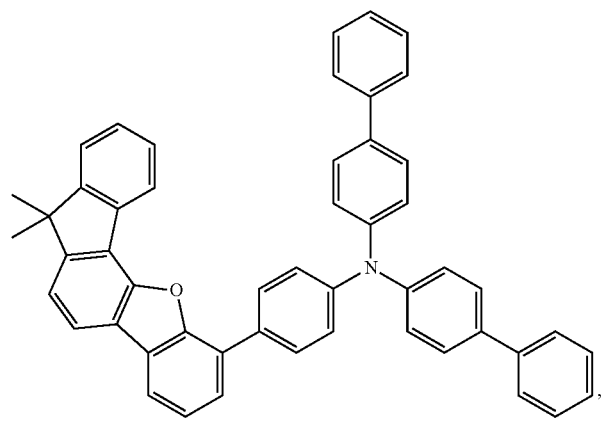
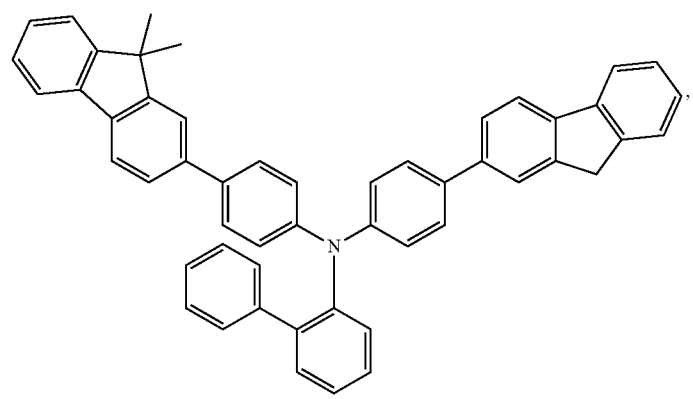
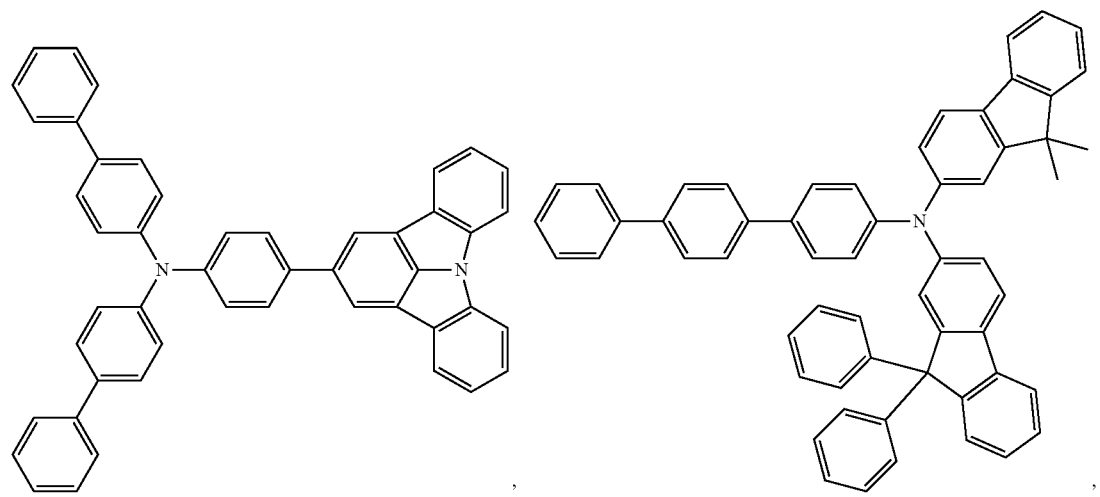

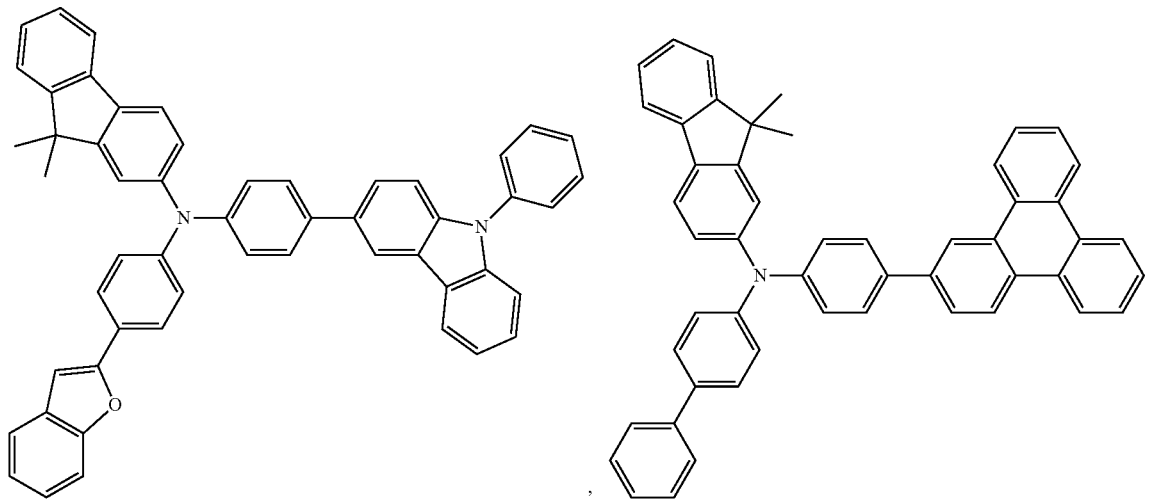
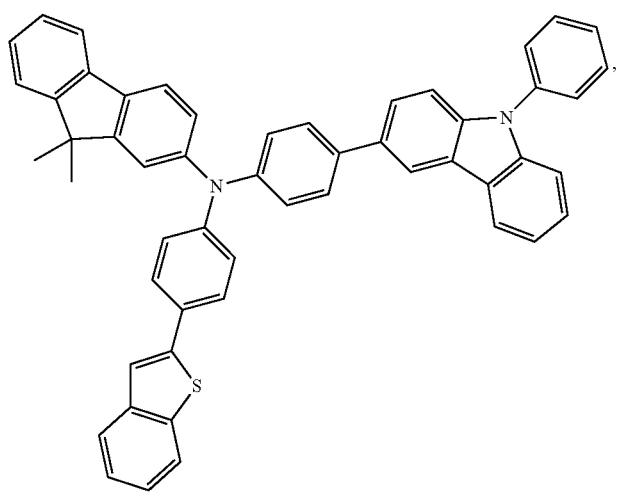
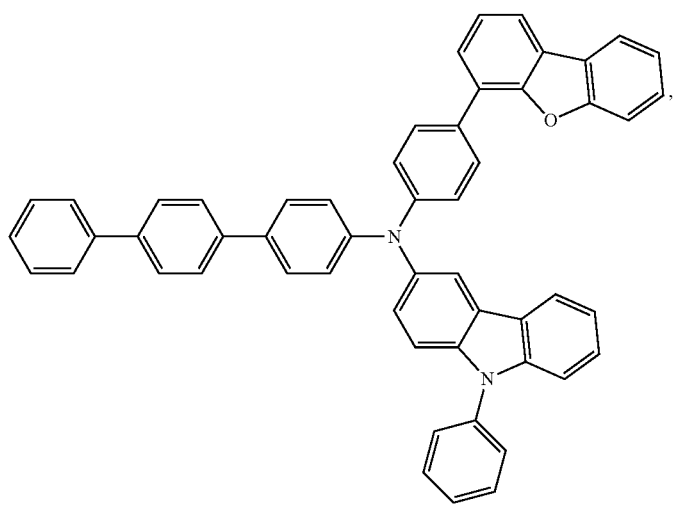

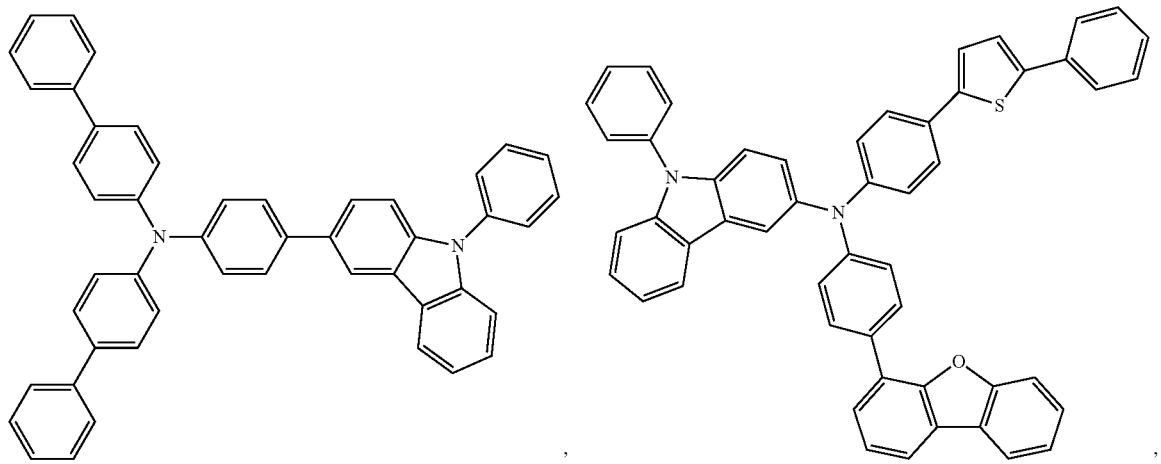
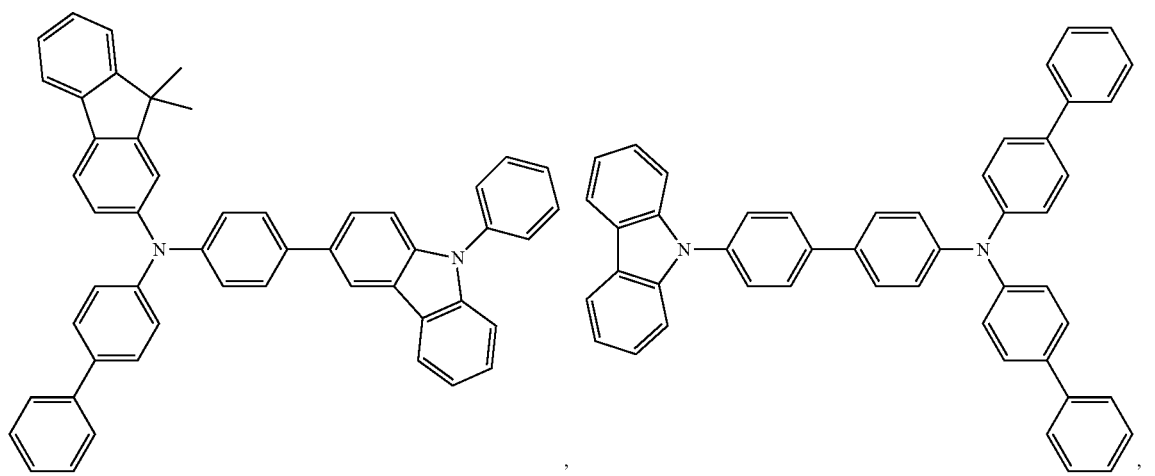
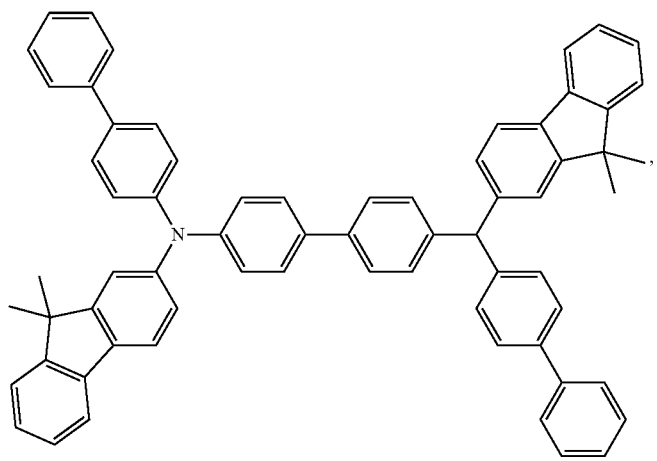

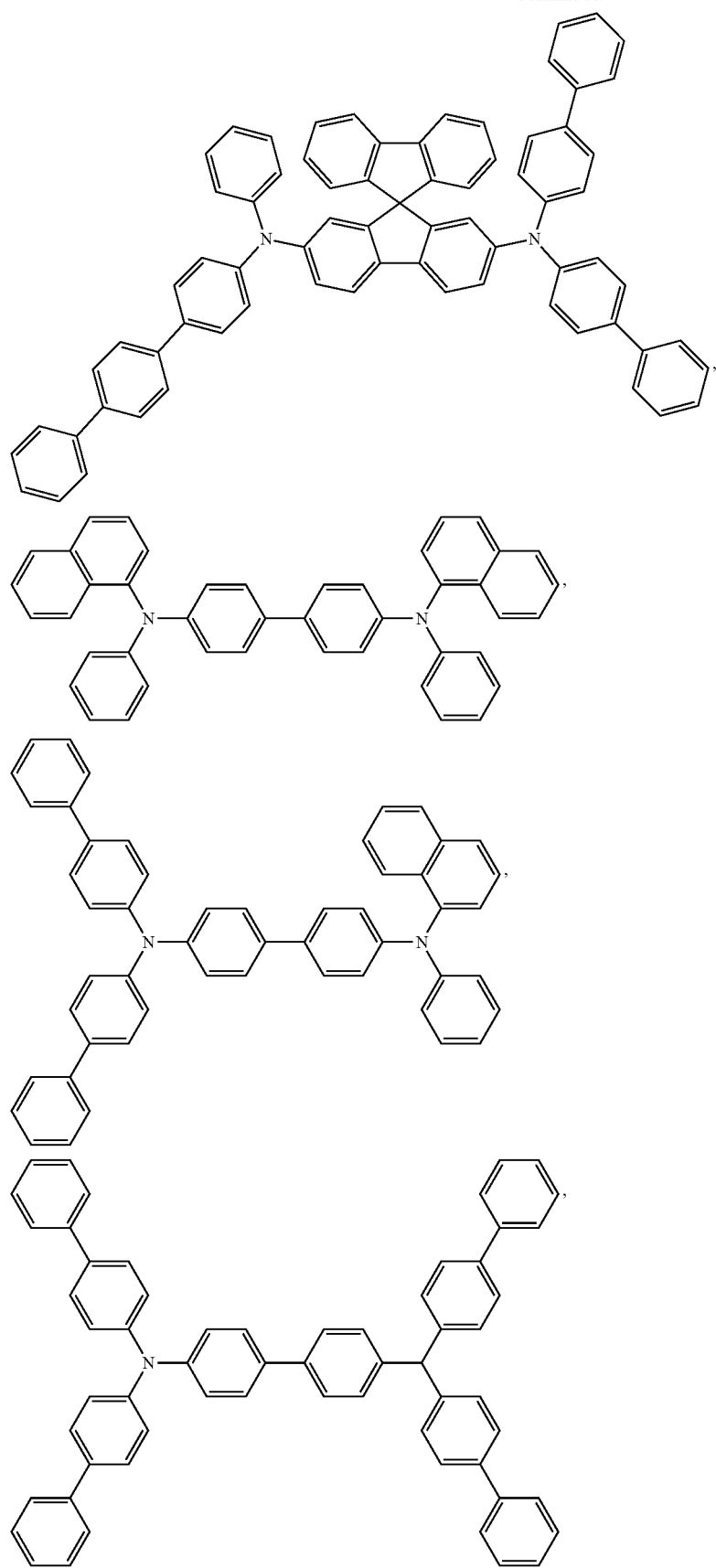

-continued
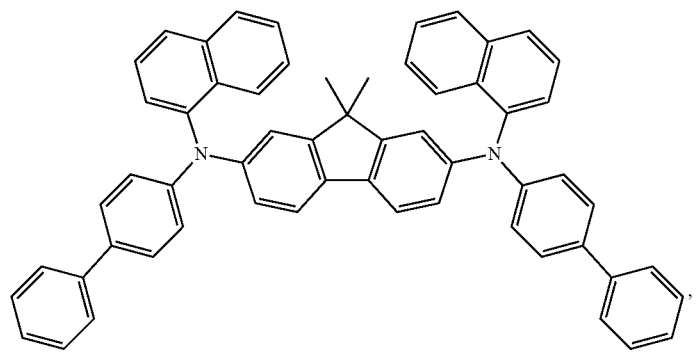
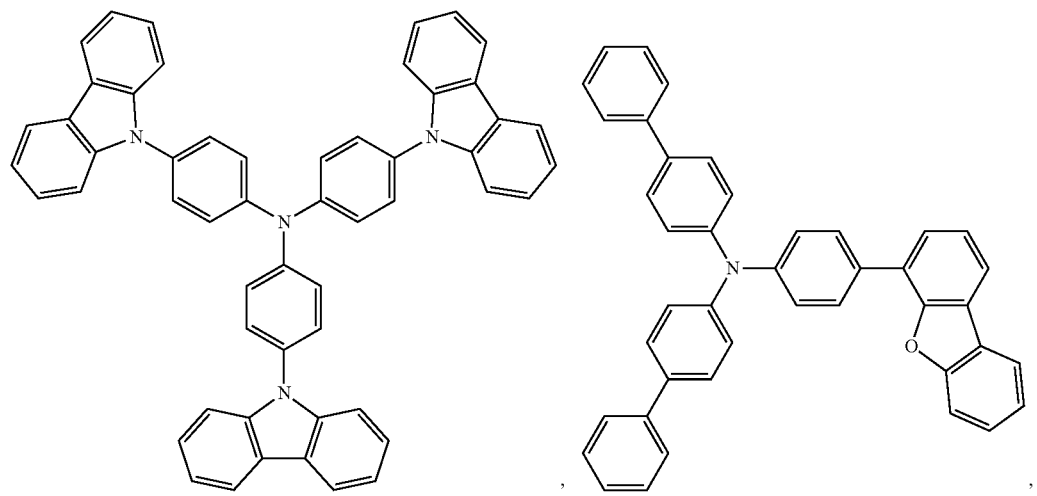
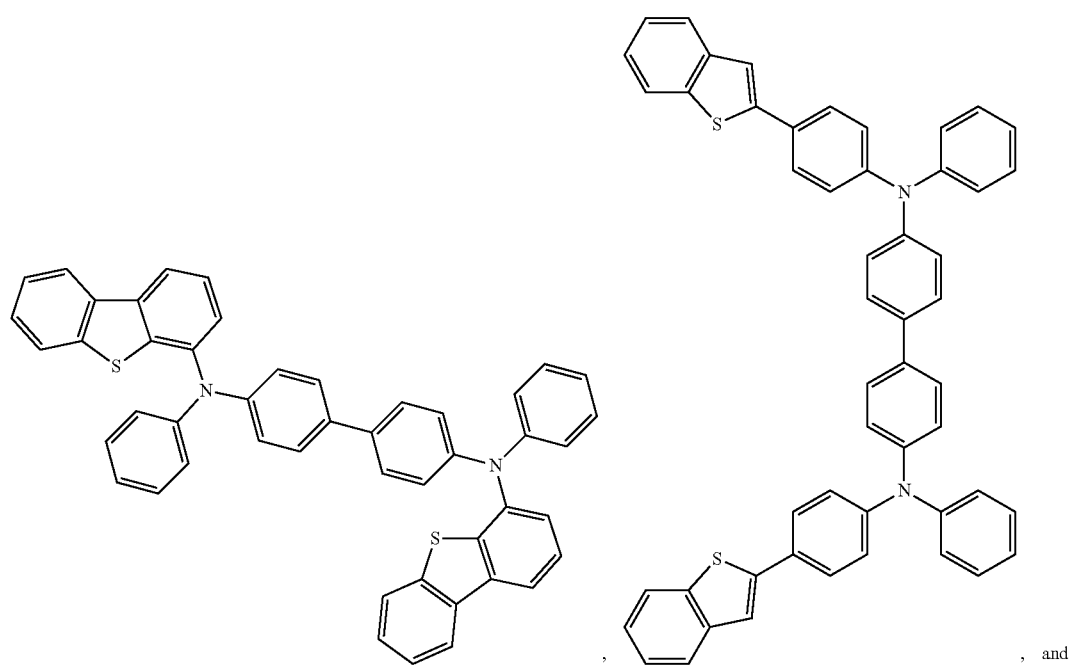
, and

-continued

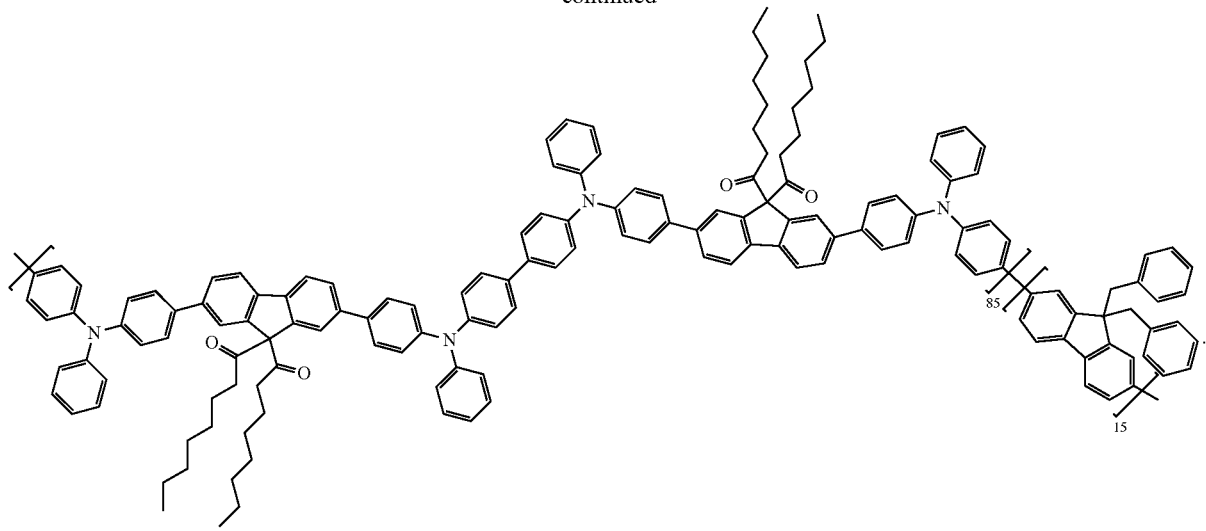

EBL:

An electron blocking layer (EBL) may be used to reduce the number of electrons and/or excitons that leave the emissive layer. The presence of such a blocking layer in a device may result in substantially higher efficiencies, and or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and or higher triplet energy than one or more of the hosts closest to the EBL interface. In one aspect, the compound used in EBL contains the same molecule or the same functional groups used as one of the hosts described below.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

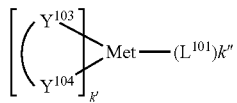

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

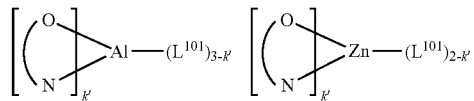

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

Examples of organic compounds used as host are selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the host compound contains at least one of the following groups in the molecule:

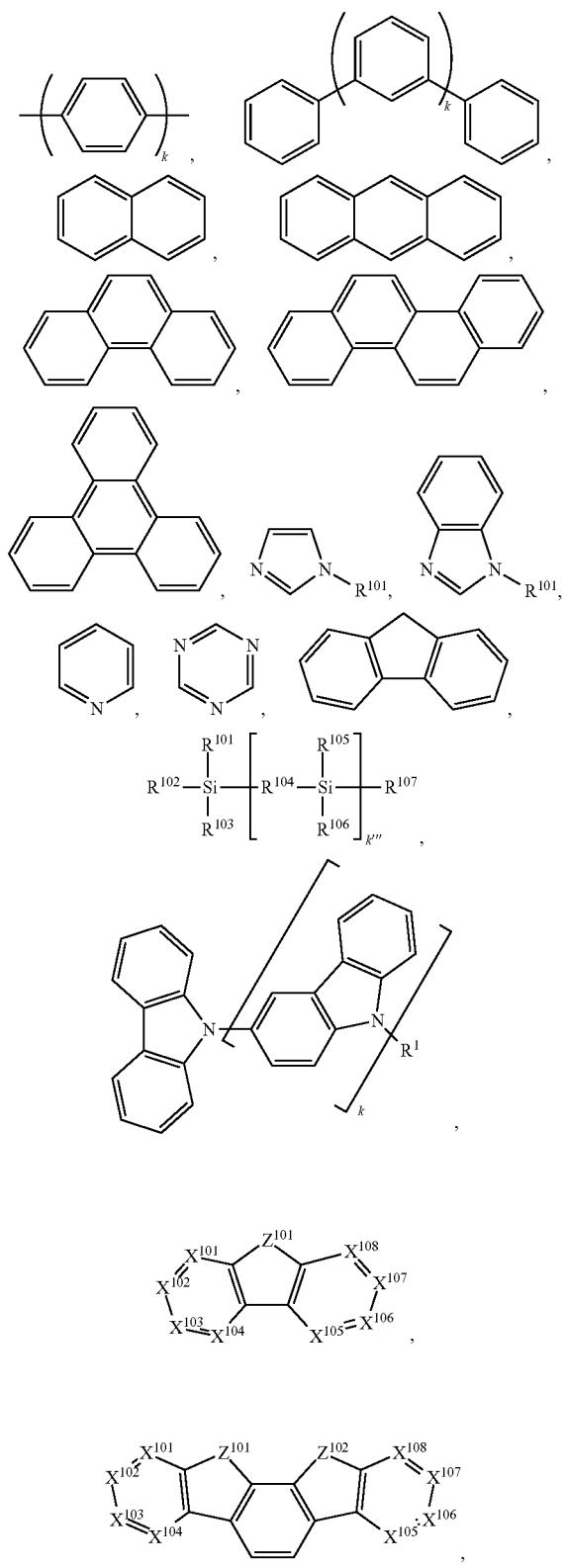

wherein each of $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

Non-limiting examples of the Host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472.

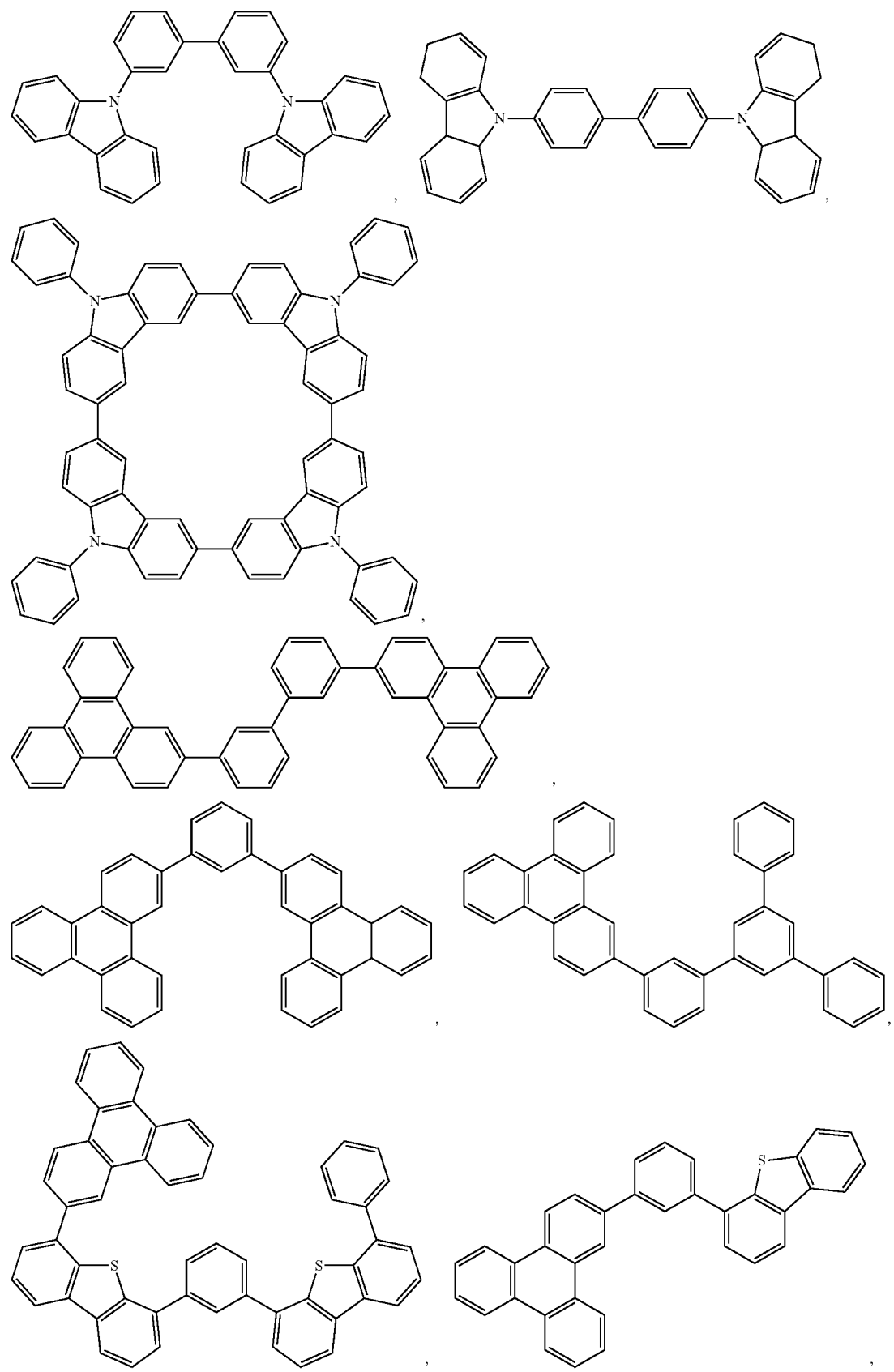

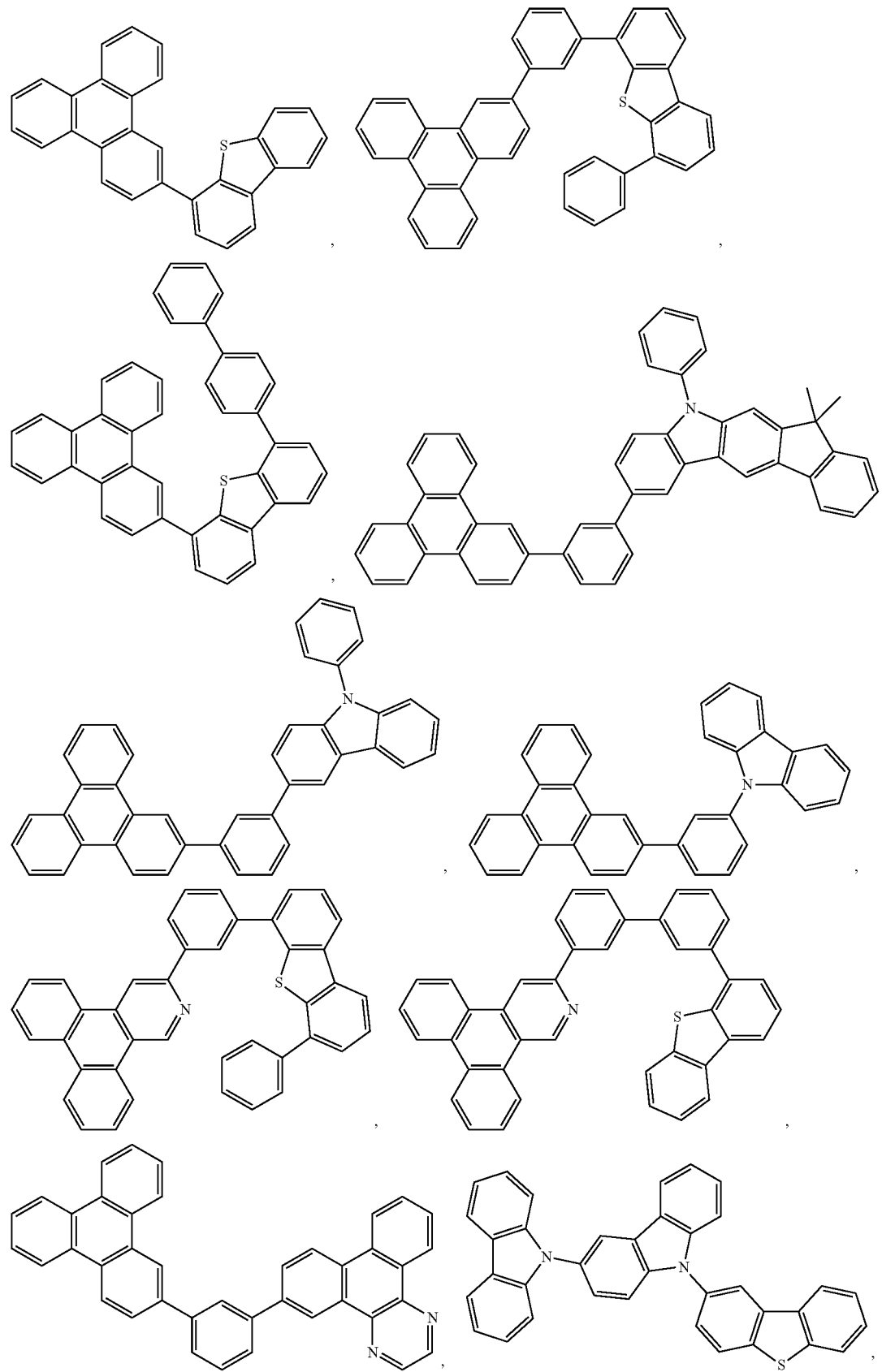

-continued
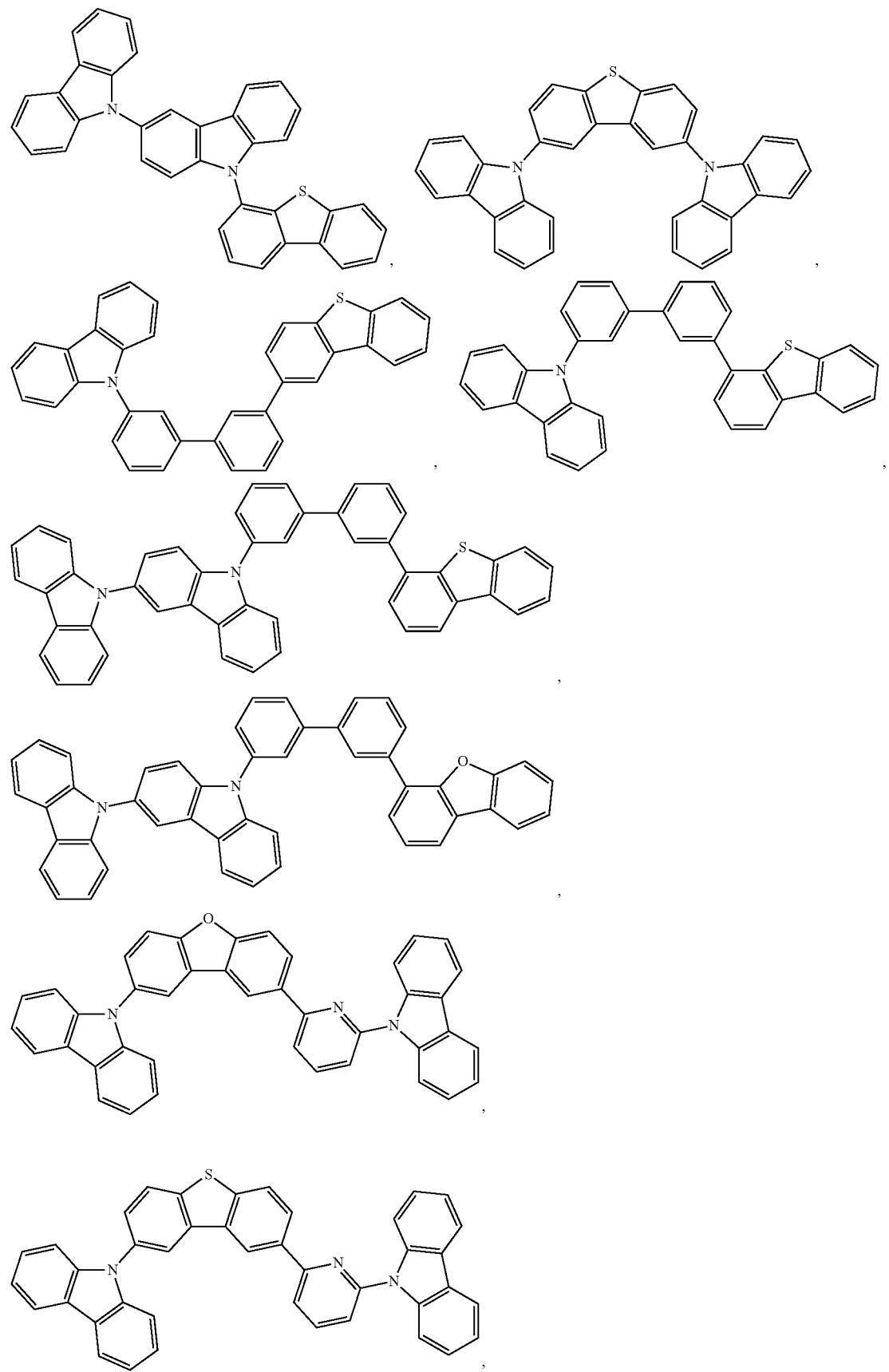

-continued
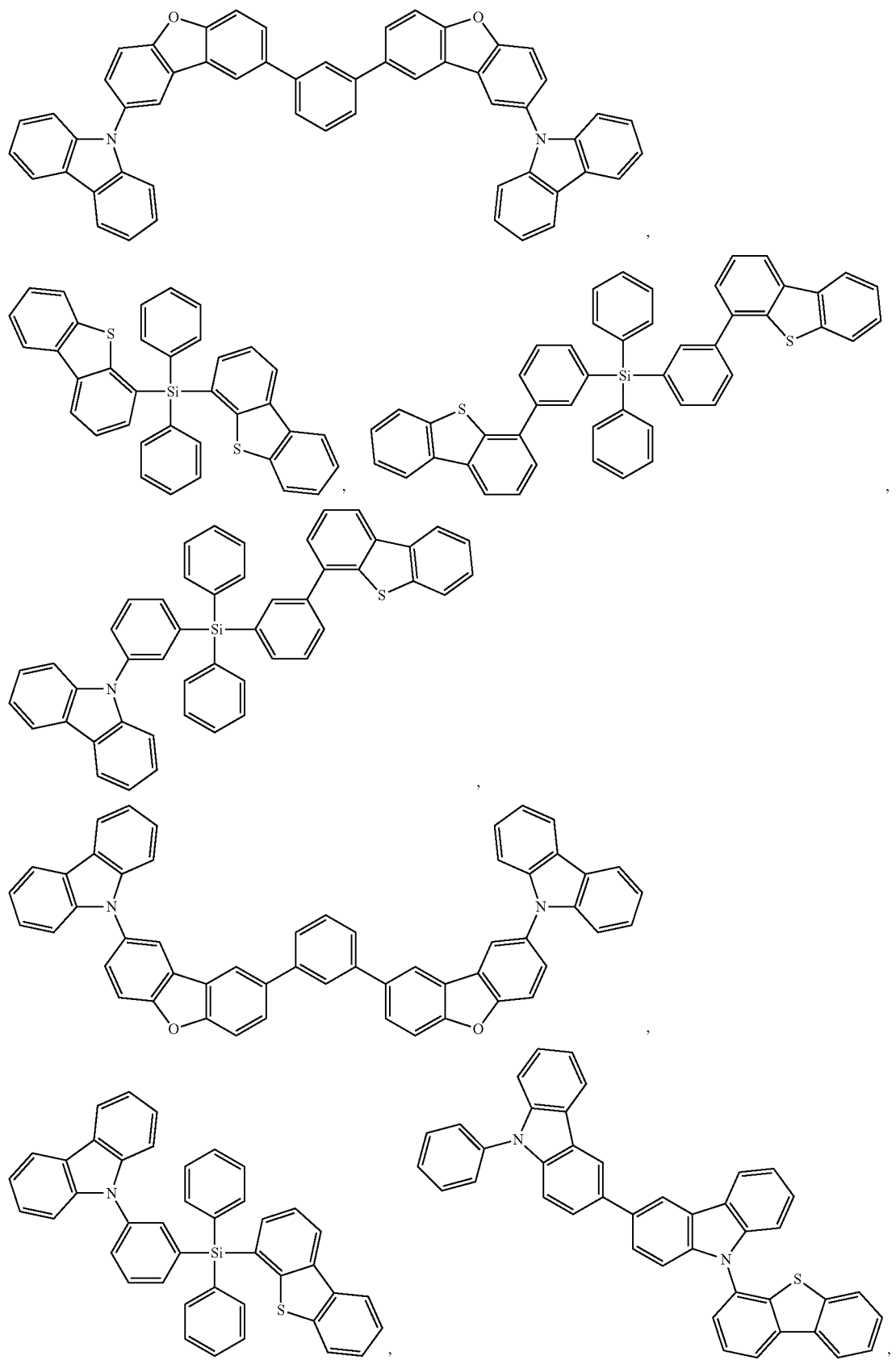

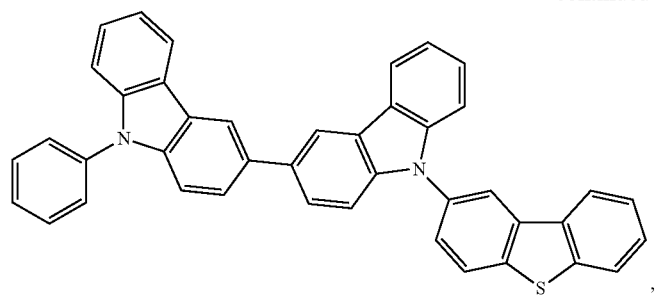
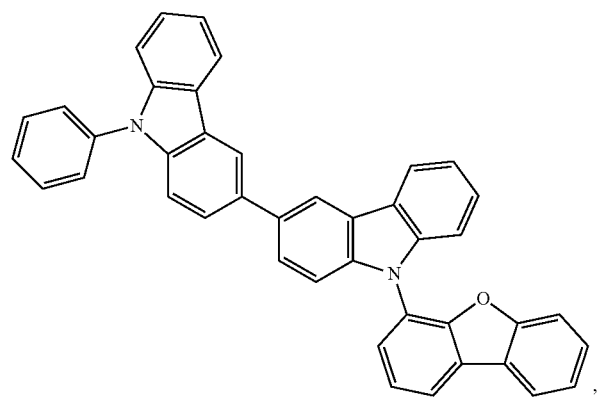
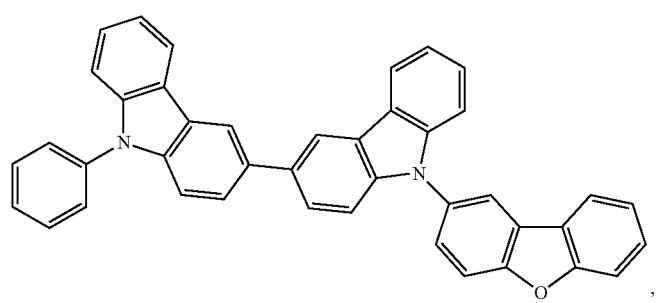
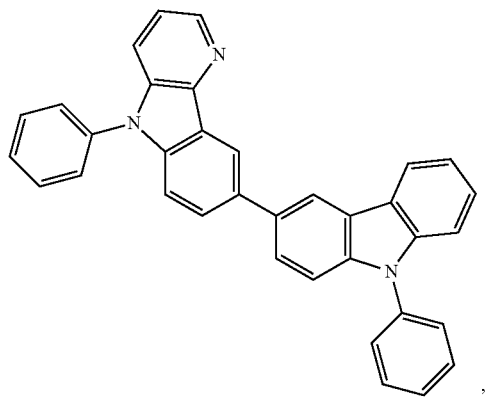
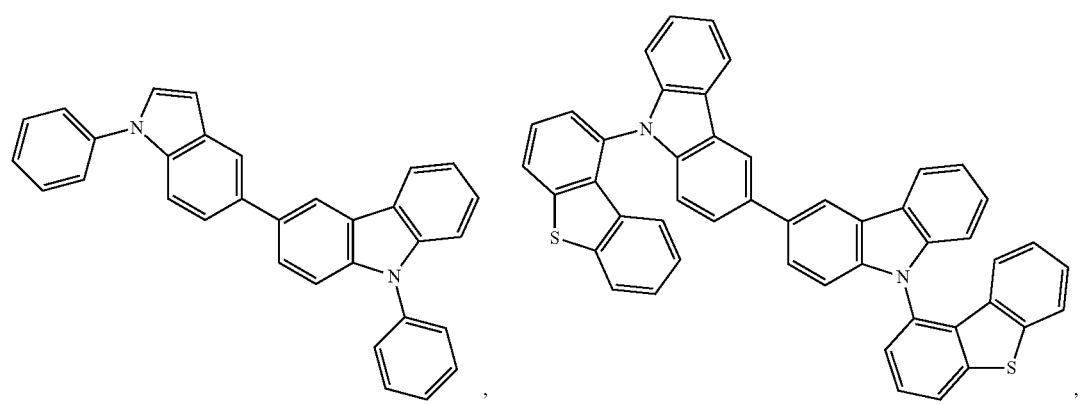

-continued
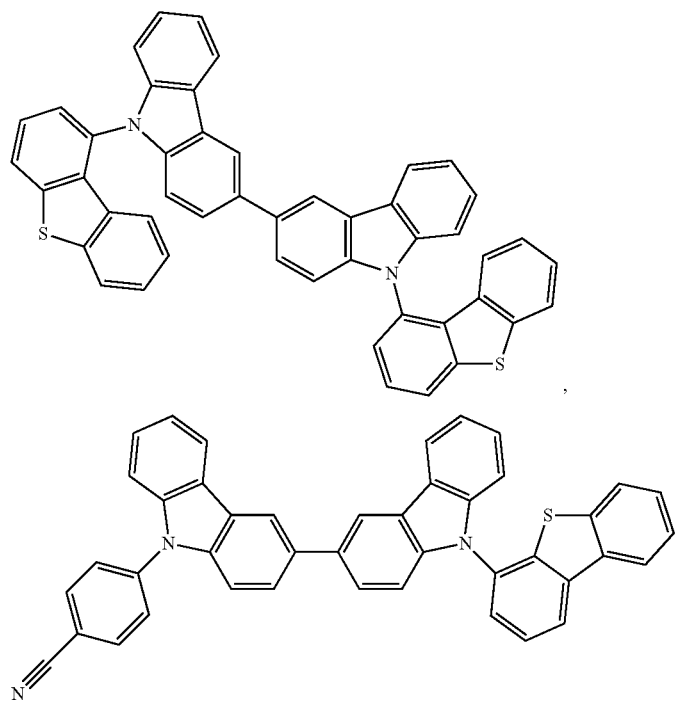
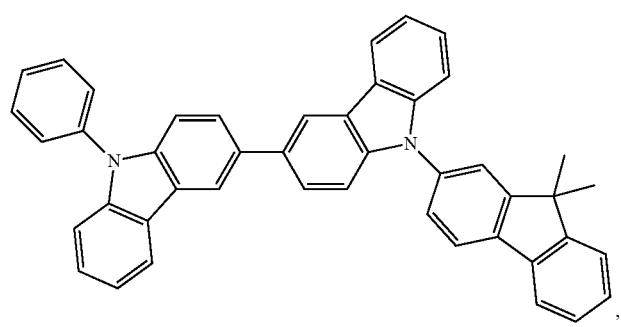
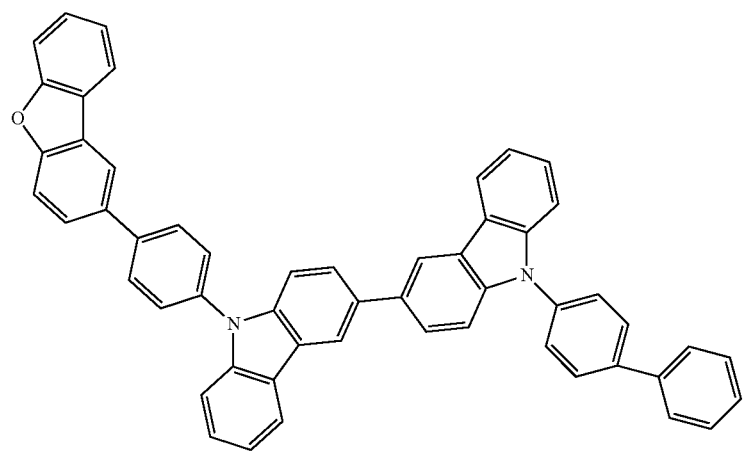

-continued
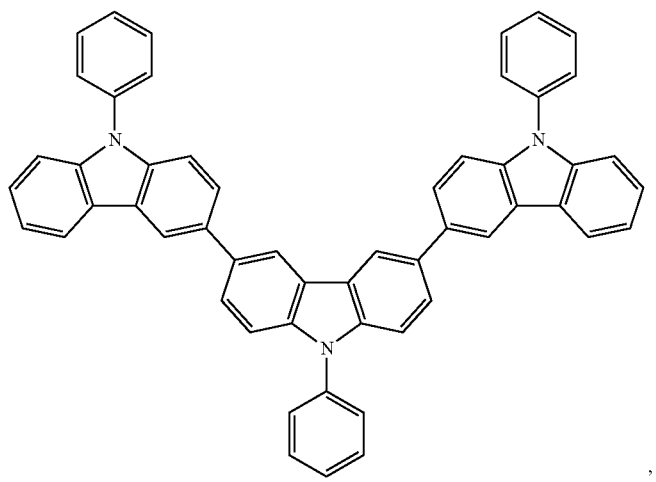
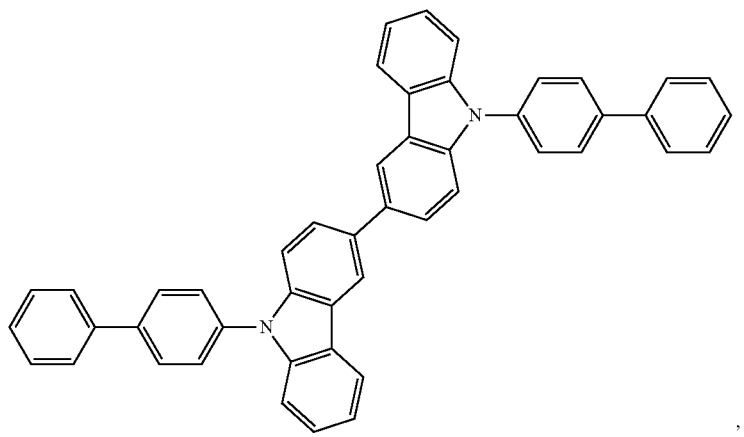
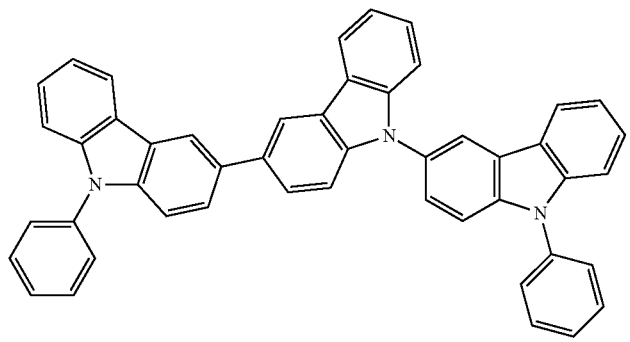
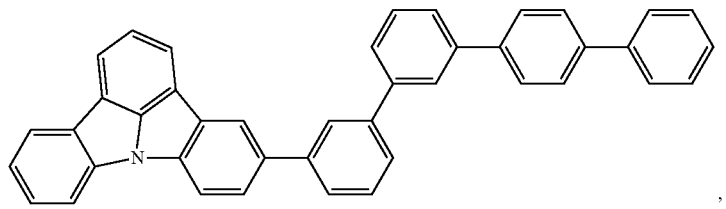

-continued
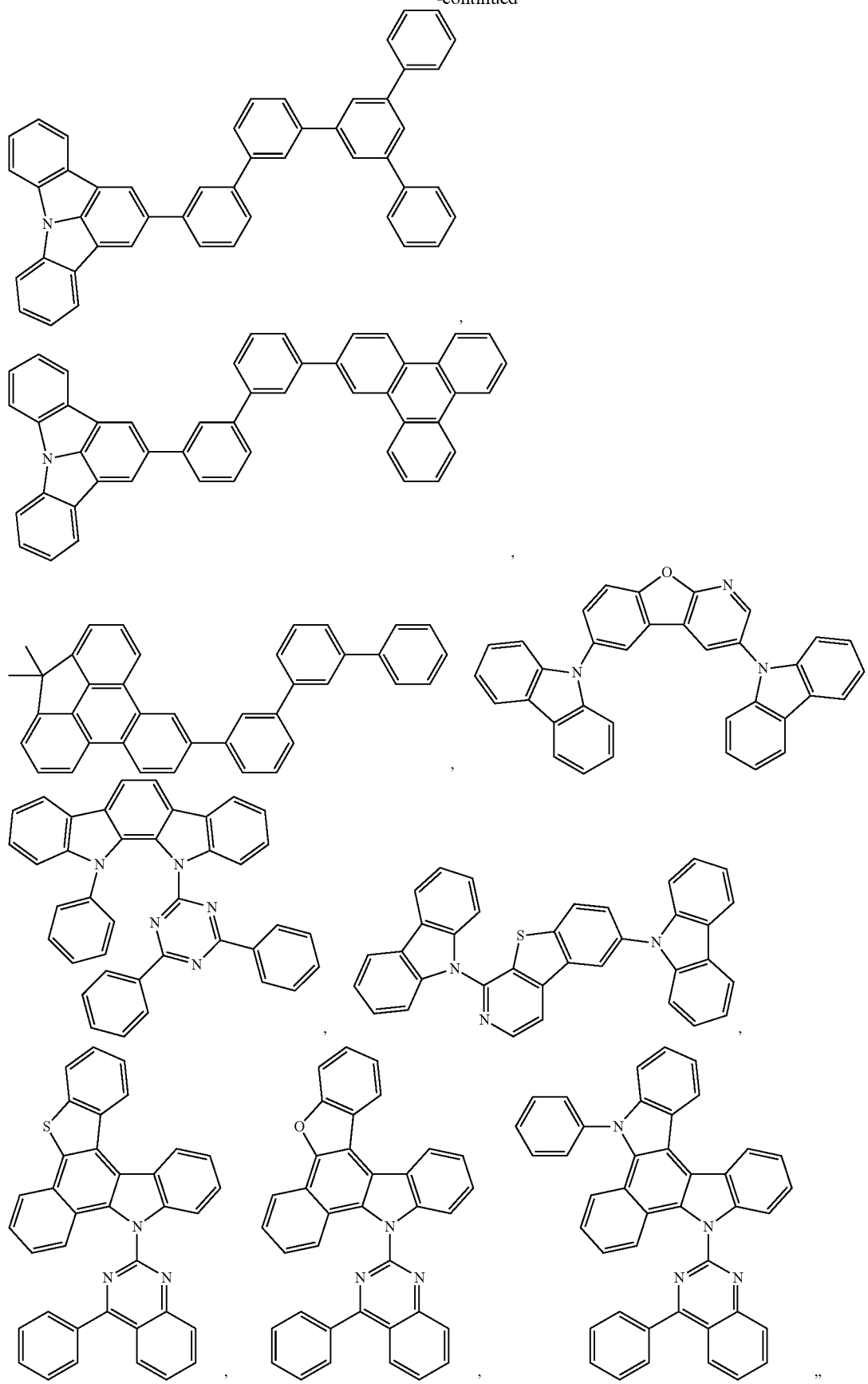

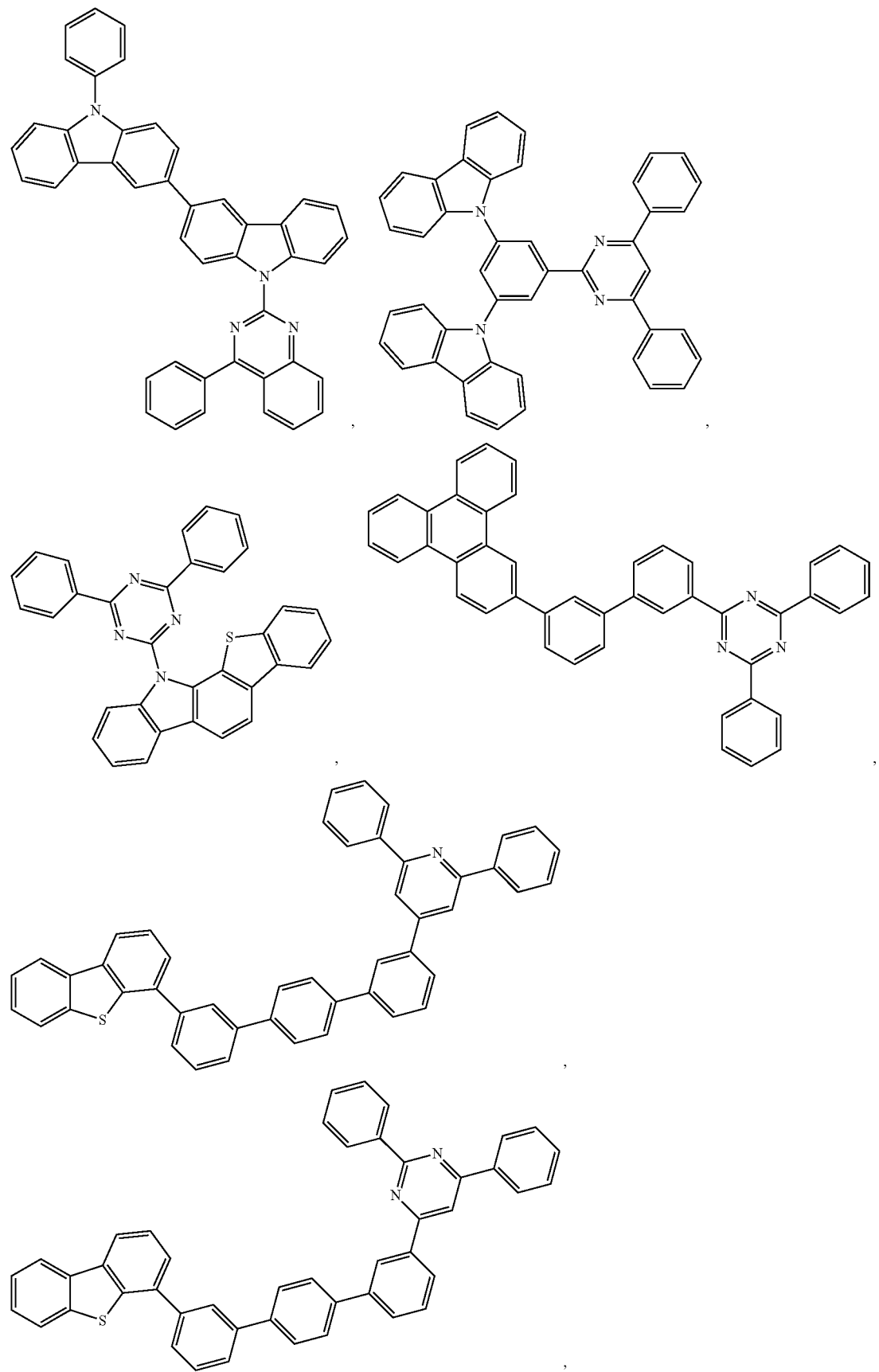

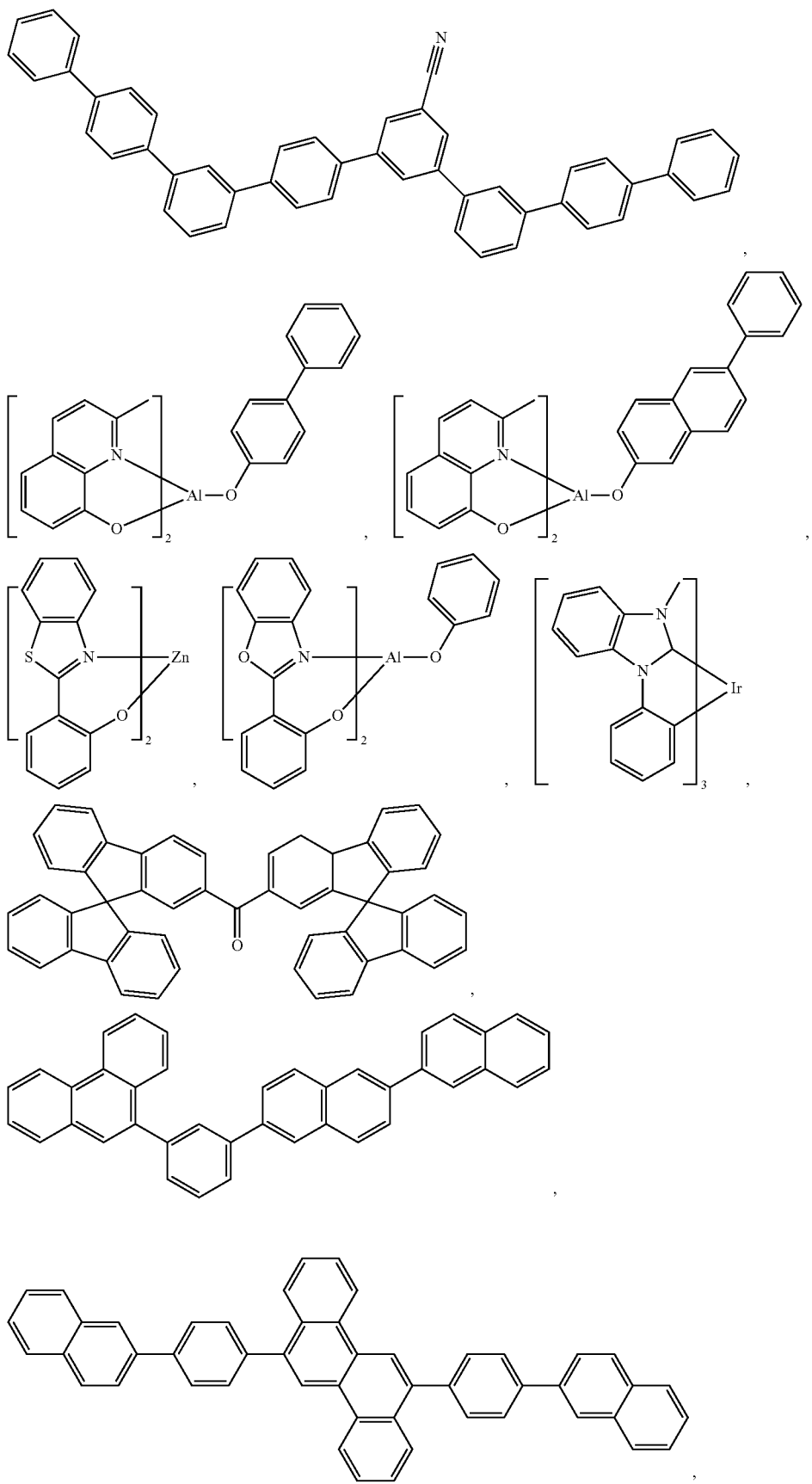

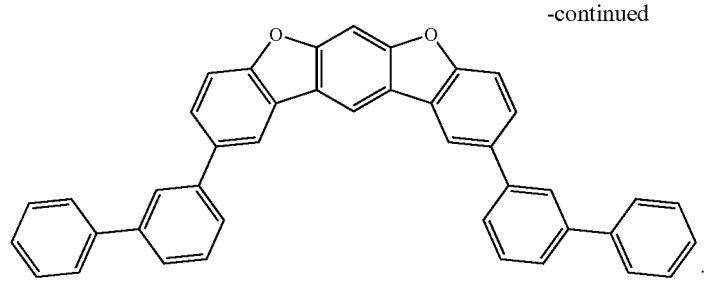

Emitter:

An emitter example is not particularly limited, and any compound may be used as long as the compound is typically used as an emitter material. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. Nos. 06/699,599, 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2009028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.

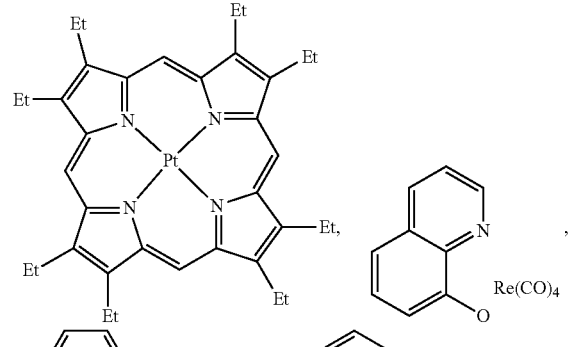

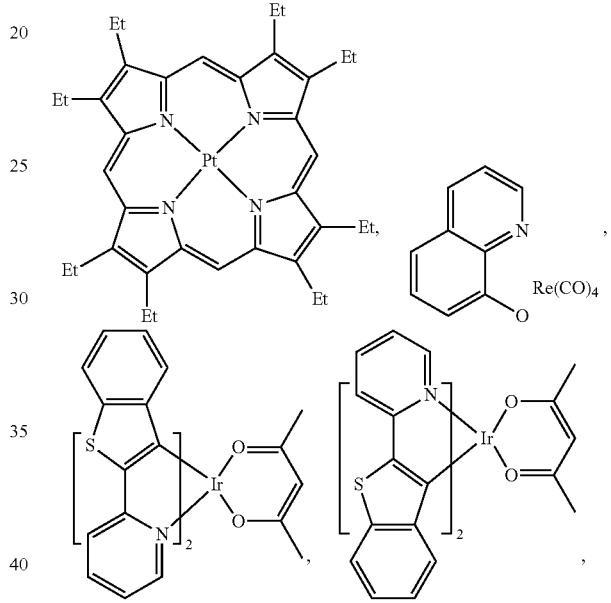

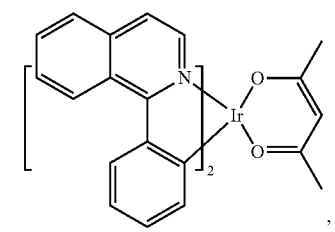

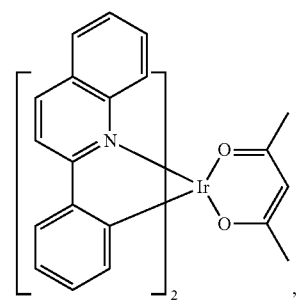

99
-continued
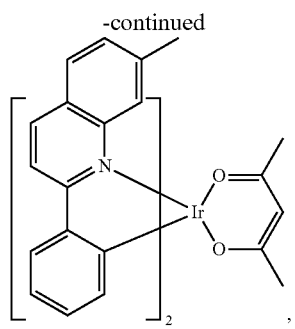
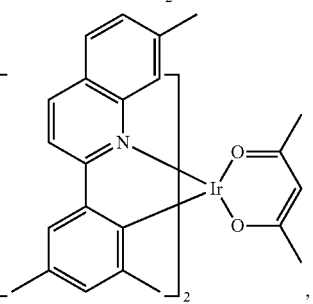
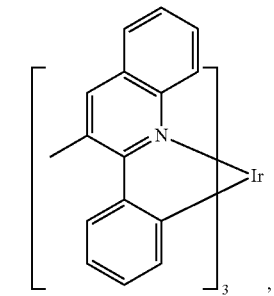
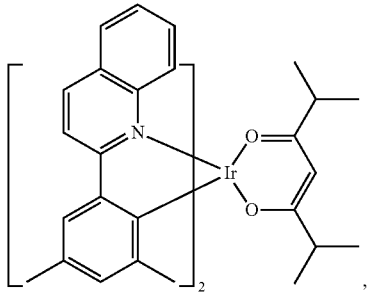
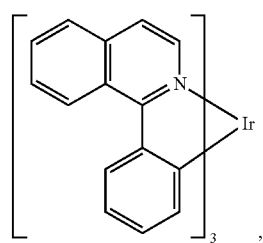
100
-continued
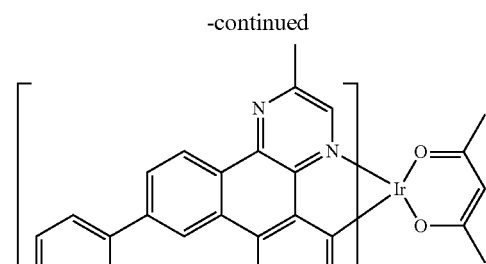
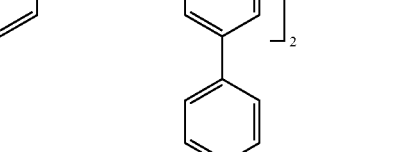
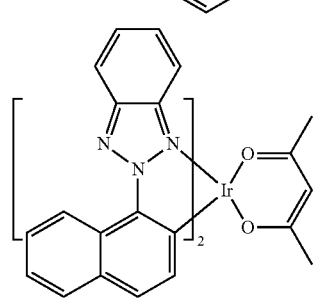
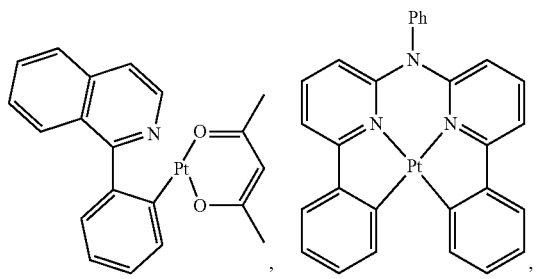
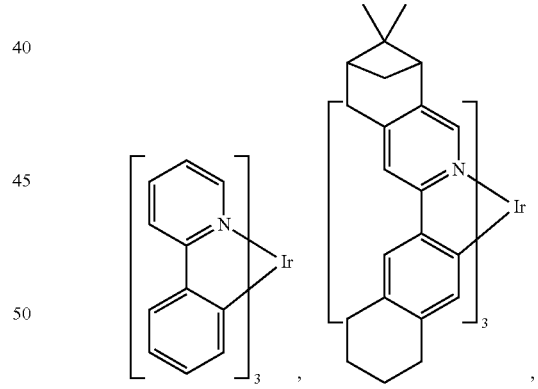
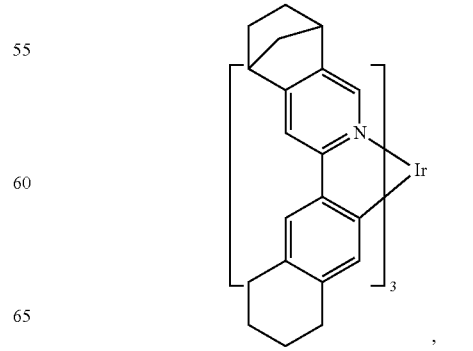

101
-continued

102
-continued

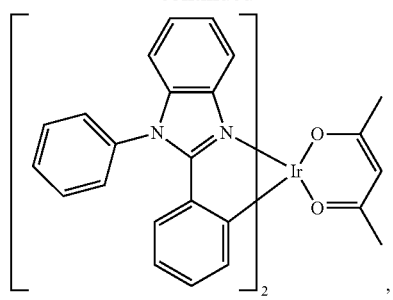
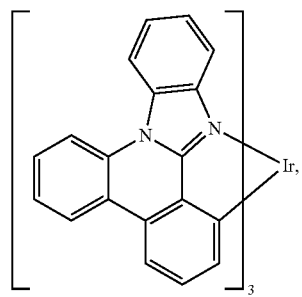
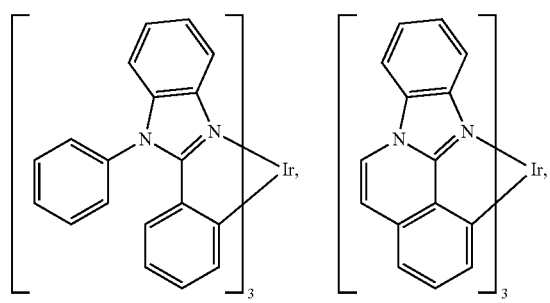
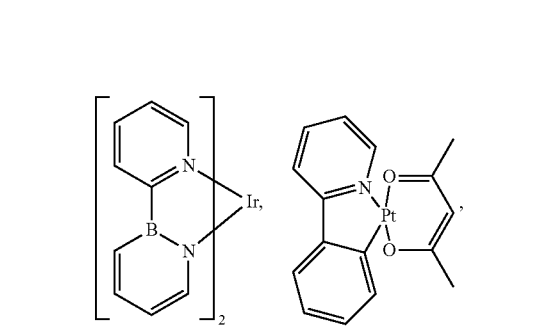
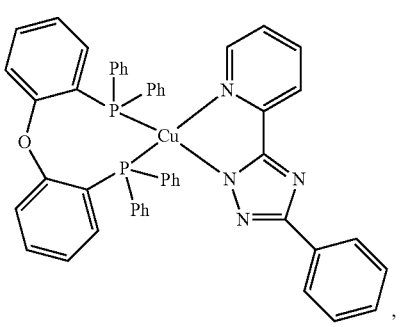
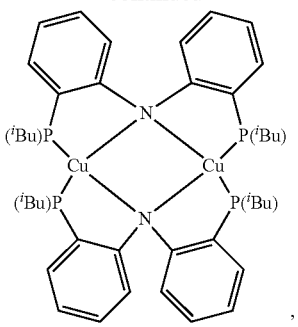
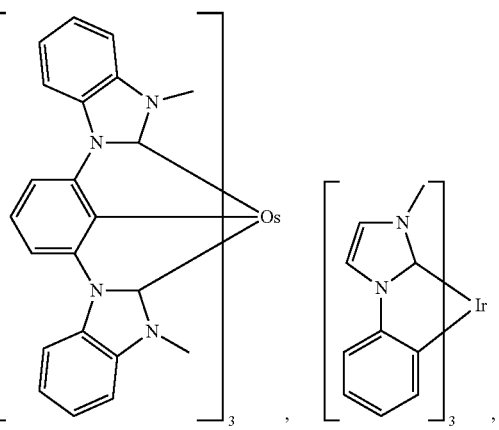
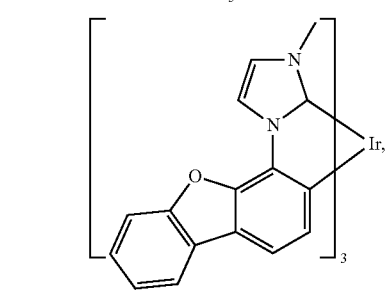
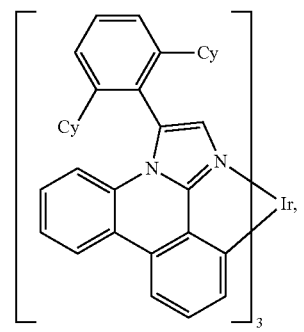
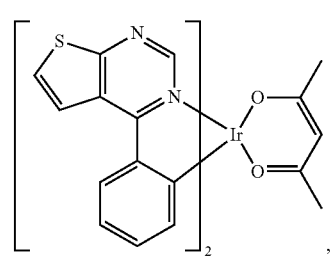

-continued
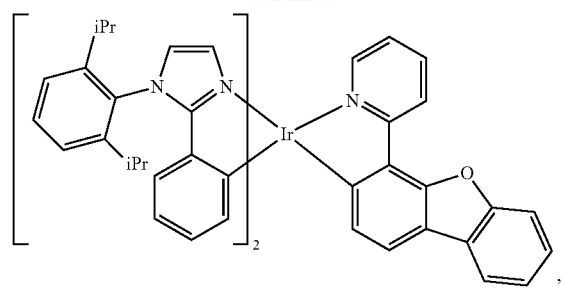
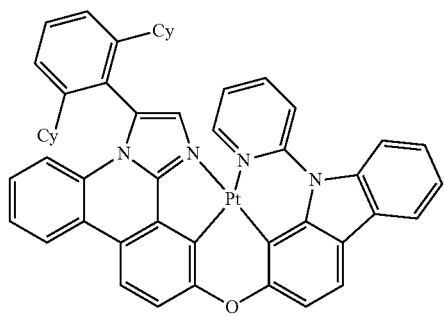
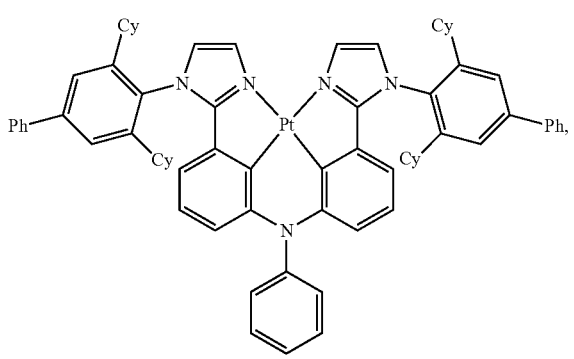
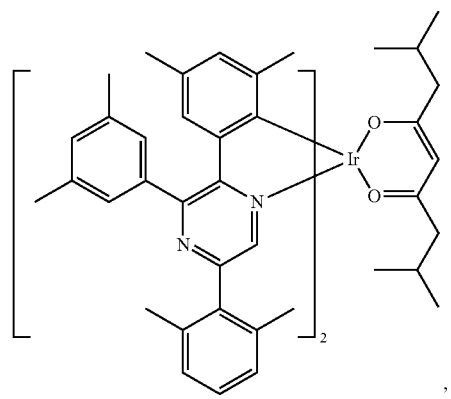
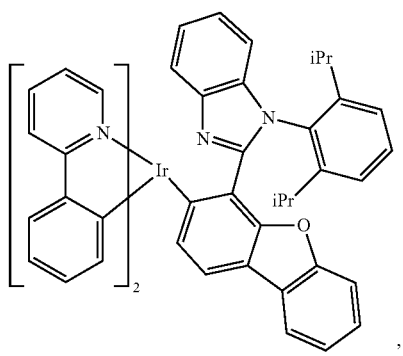
-continued
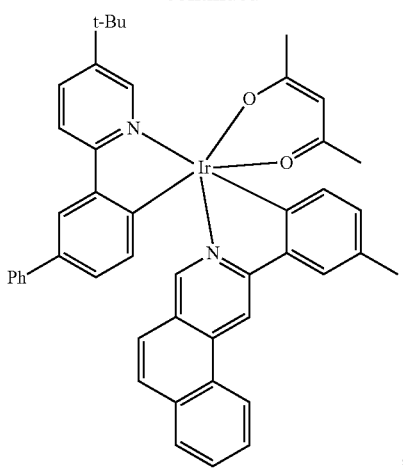
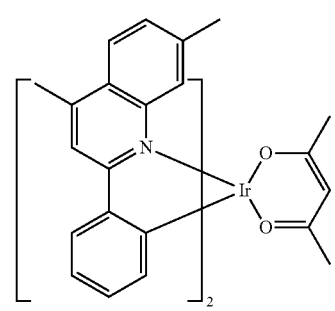
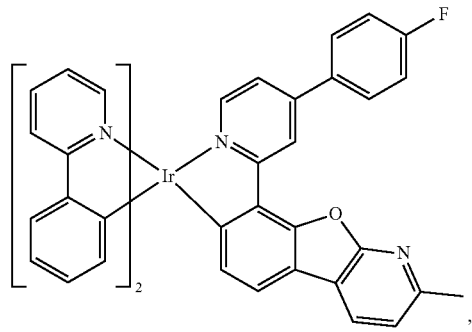
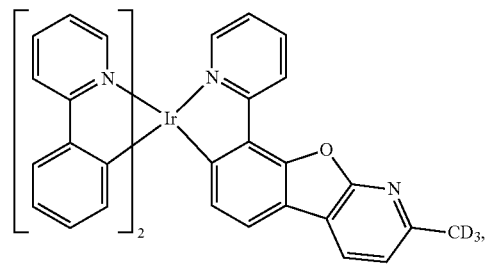
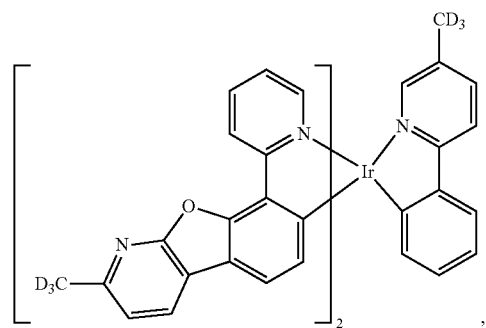

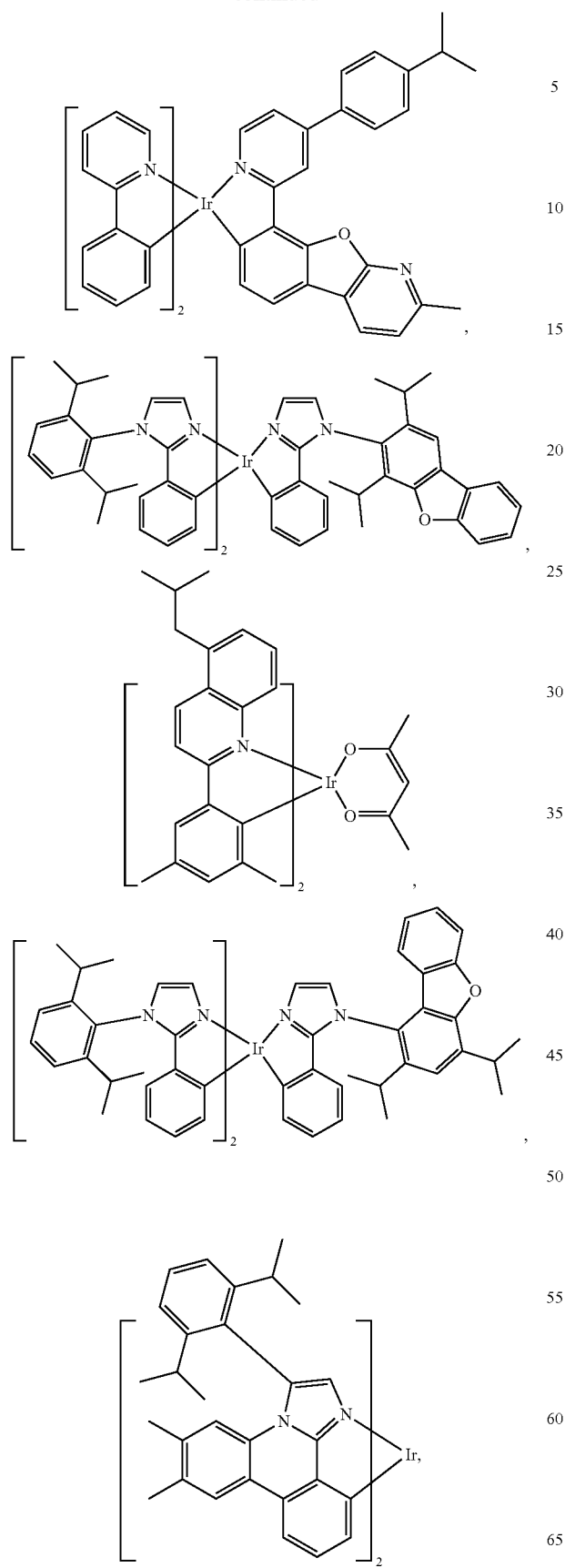
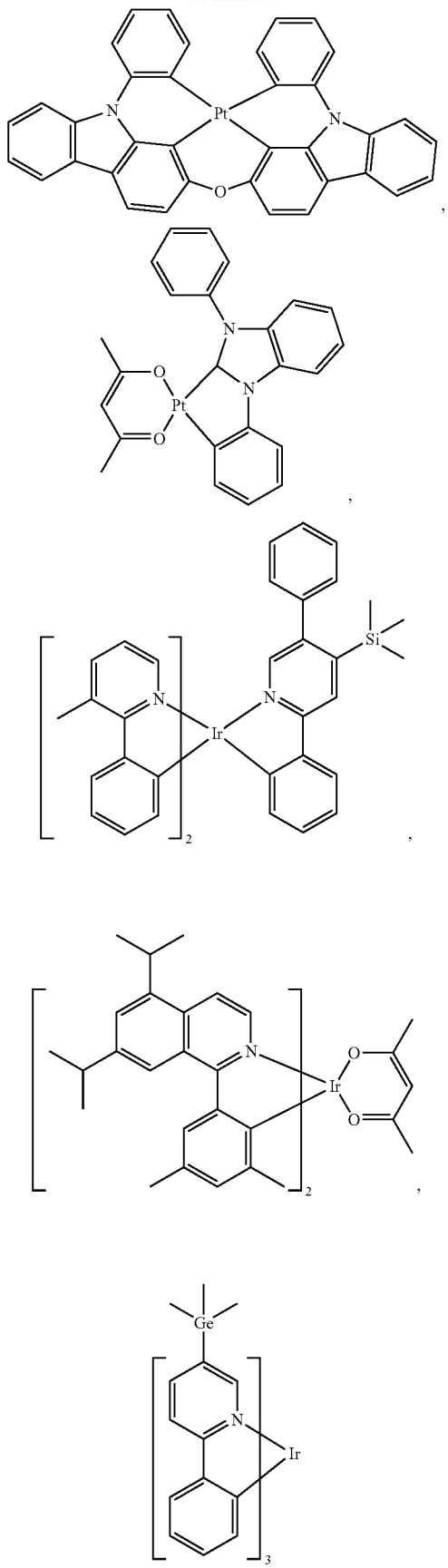

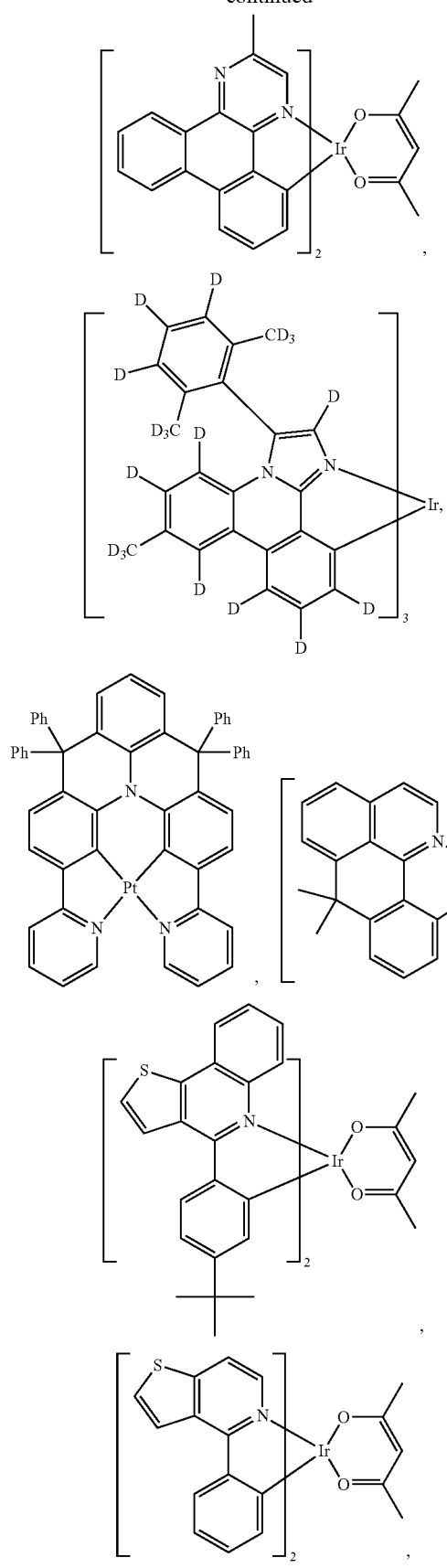
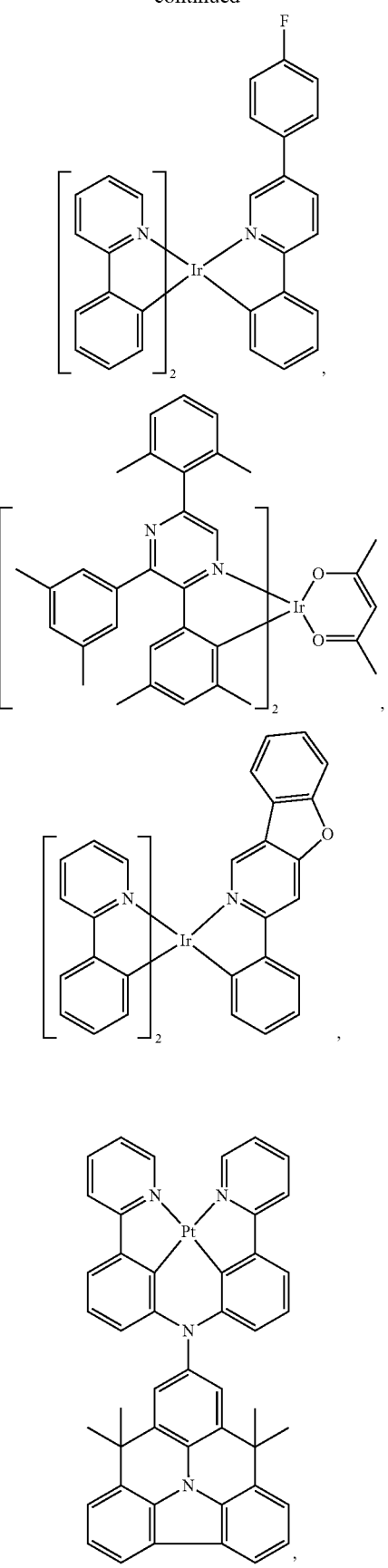

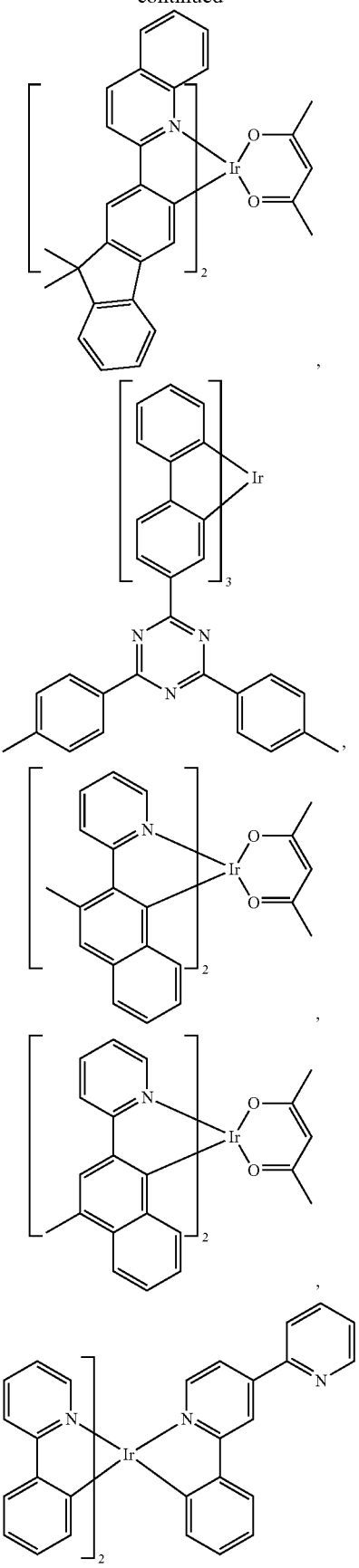
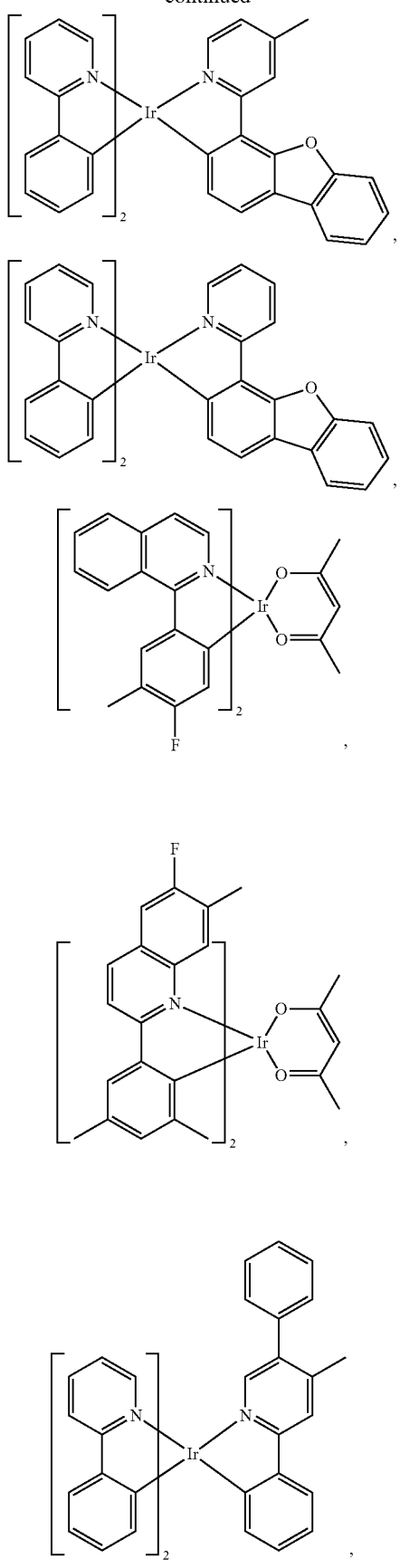

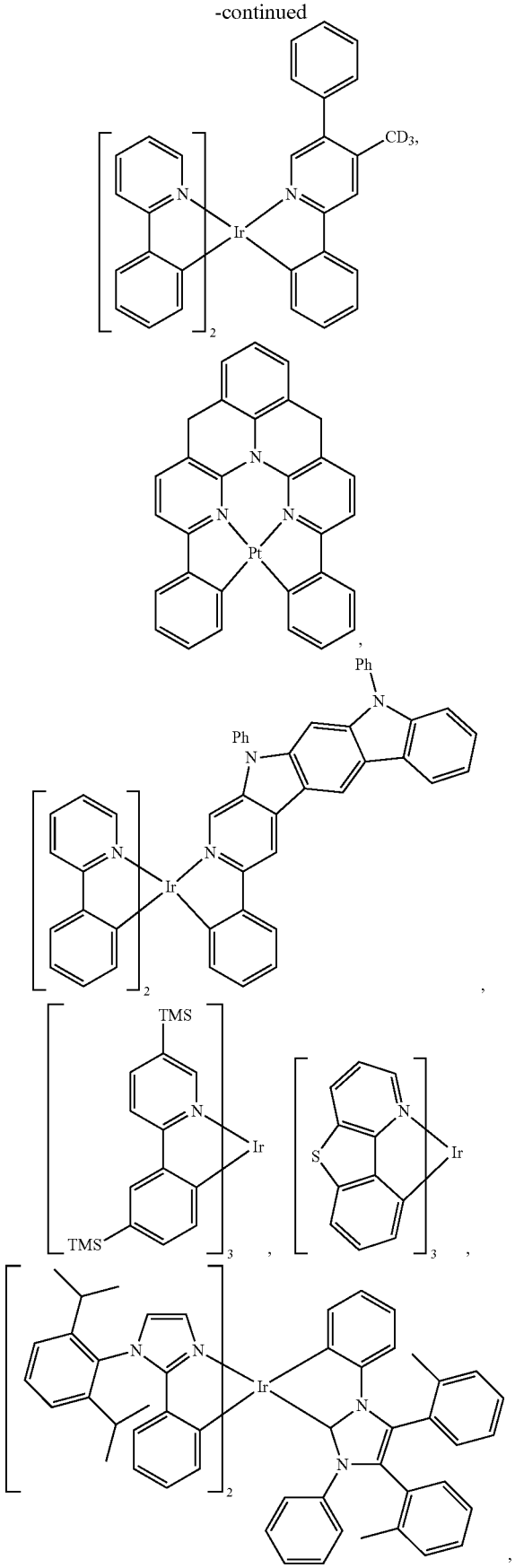
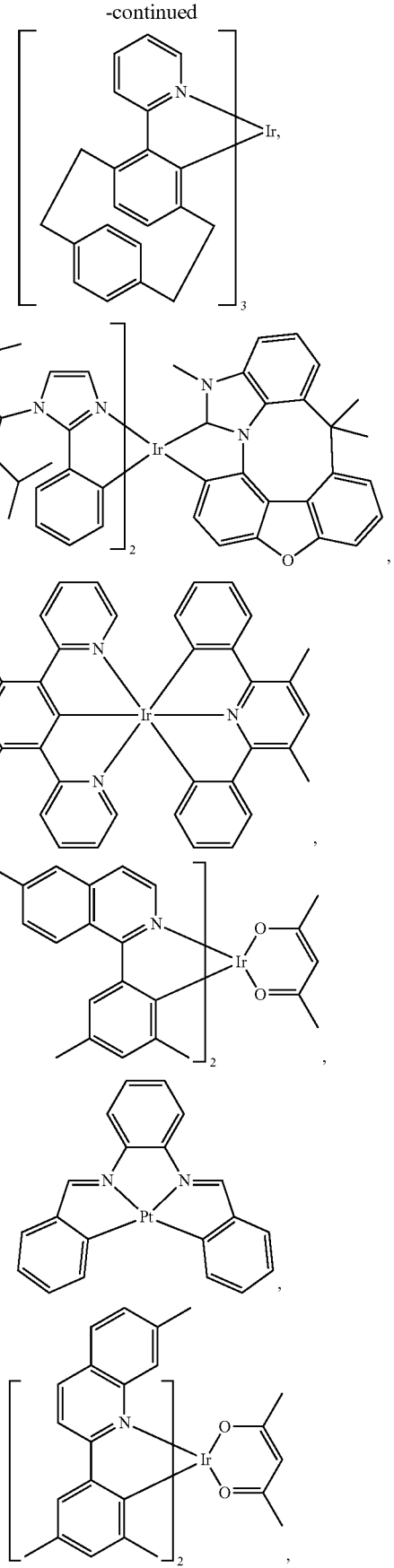

115
-continued
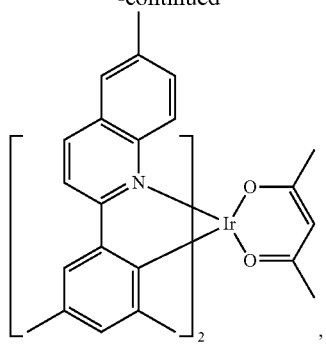
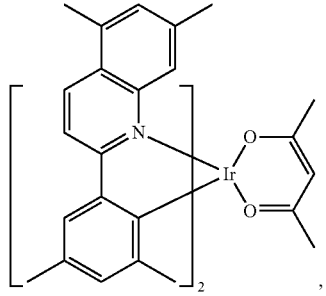
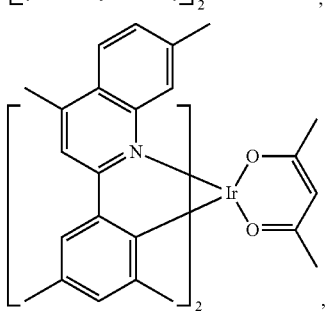
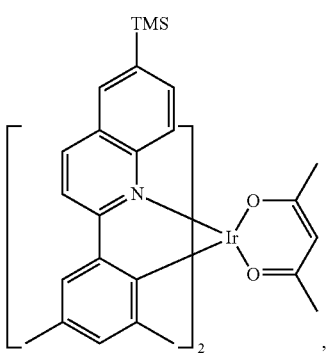
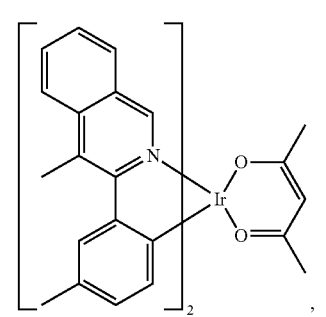
116
-continued
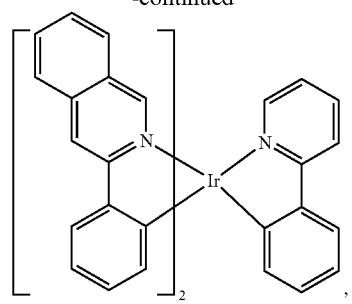
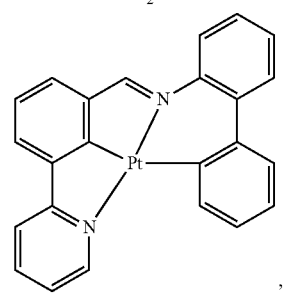
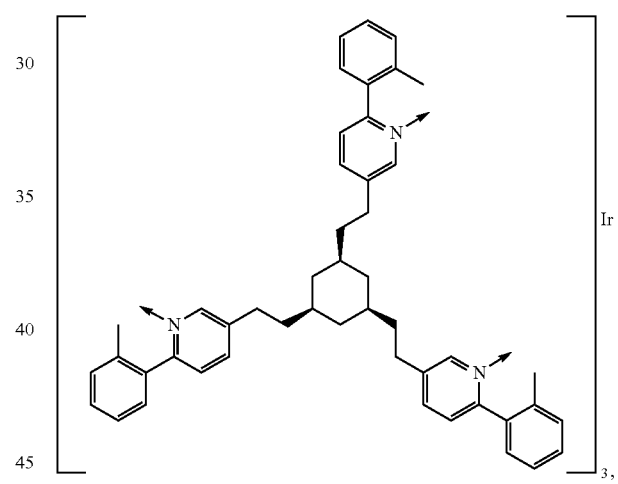
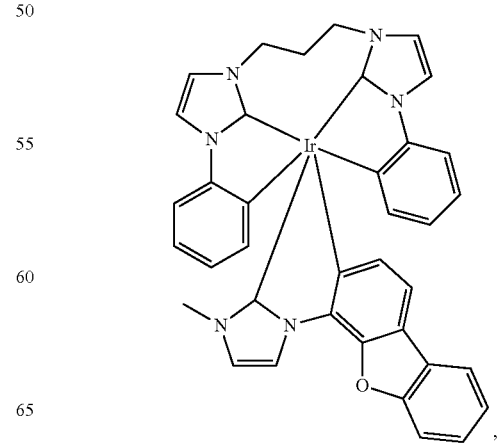

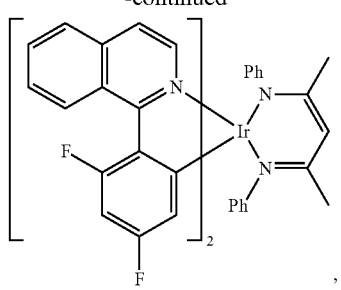
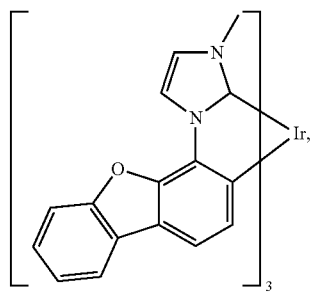
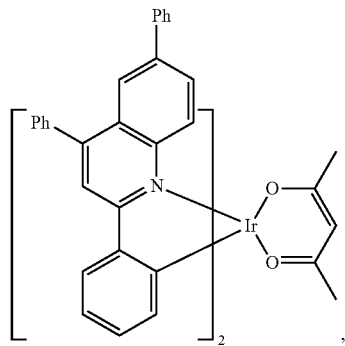
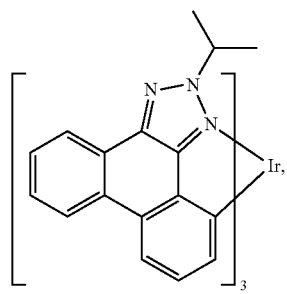
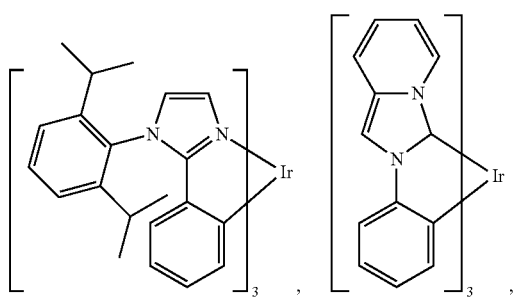
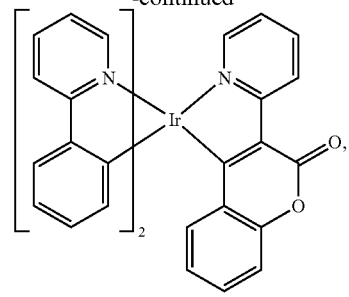
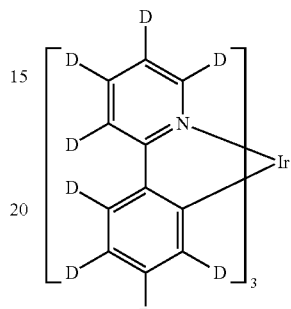
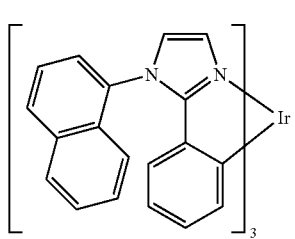
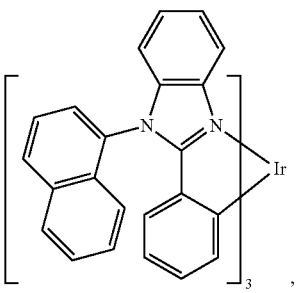
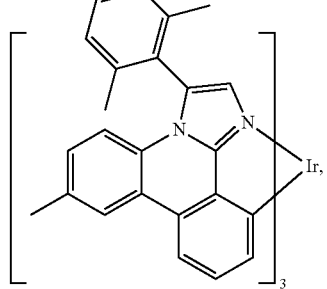
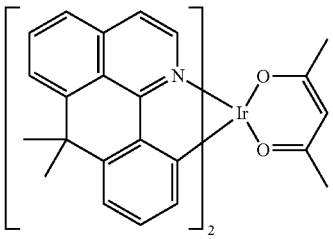
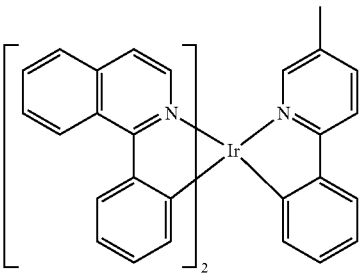

-continued

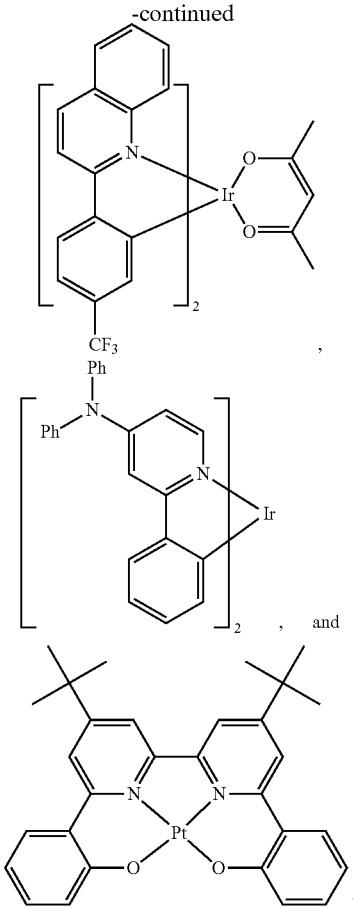
, and

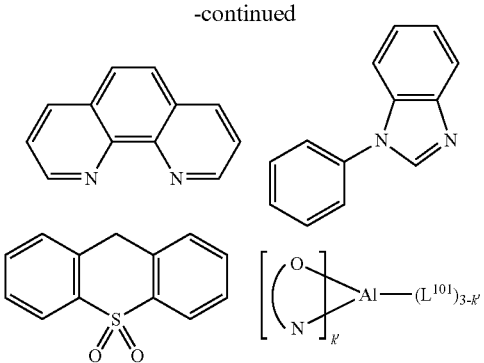

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

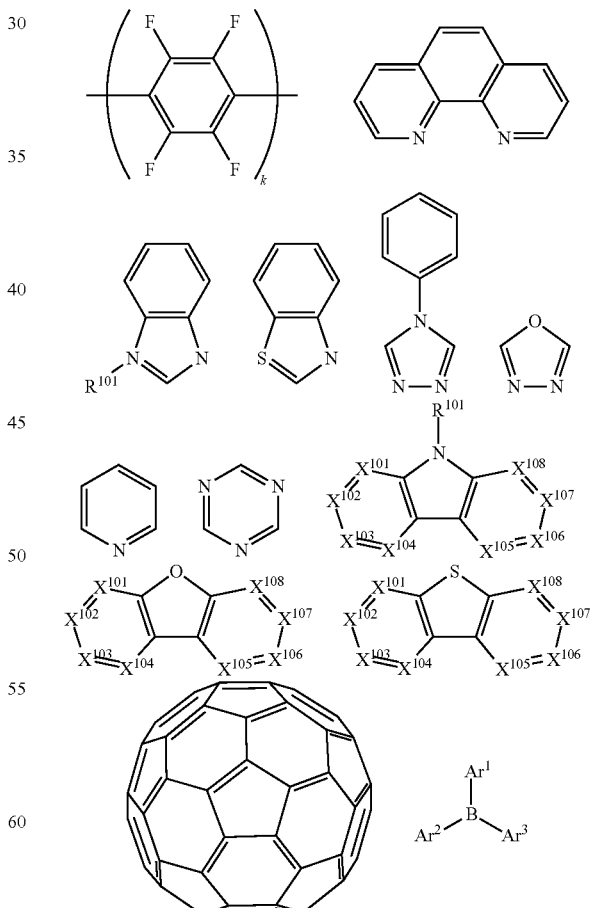

wherein $R^{101}$ is selected from the group consisting of hydrogen, deuterium, halide, alkyl, cycloalkyl, heteroalkyl, aryl-

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and or higher triplet energy than the emitter closest to the HBL interface. In some embodiments, the HBL material has a lower HOMO (further from the vacuum level) and or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

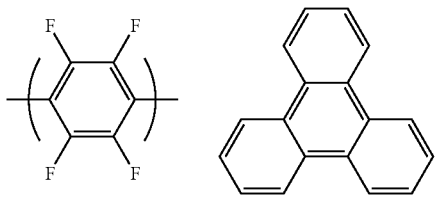

alkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

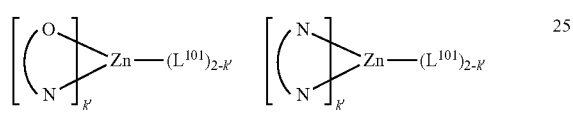

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535.

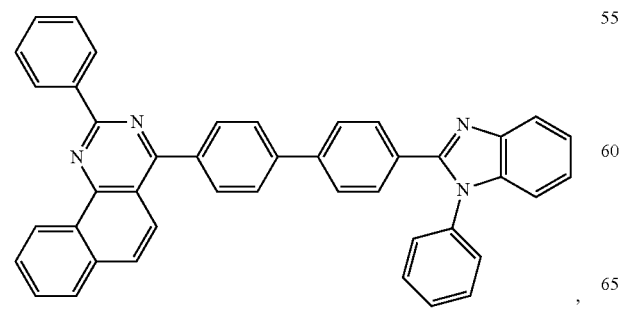

,

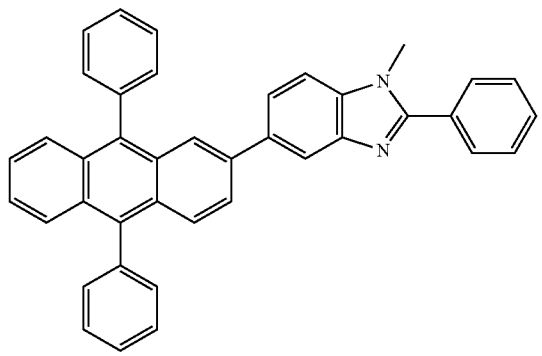

,

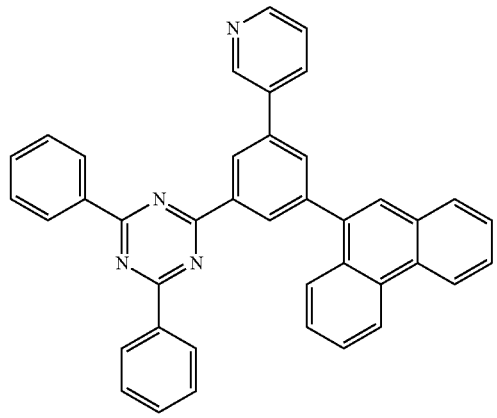

,

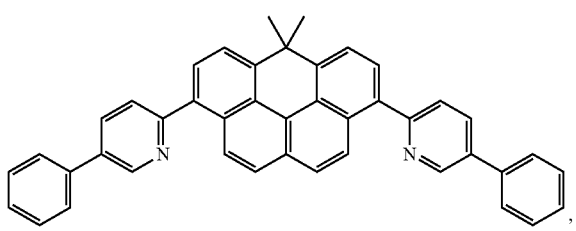

,

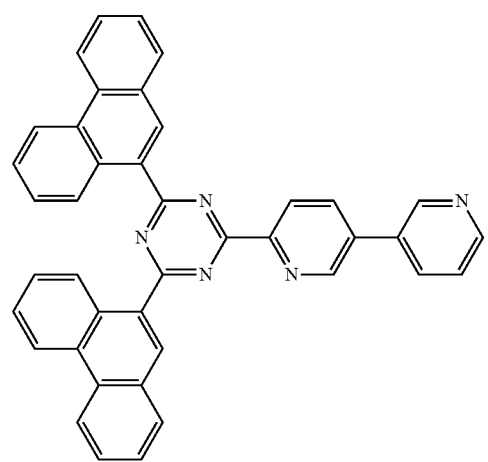

,

123
-continued
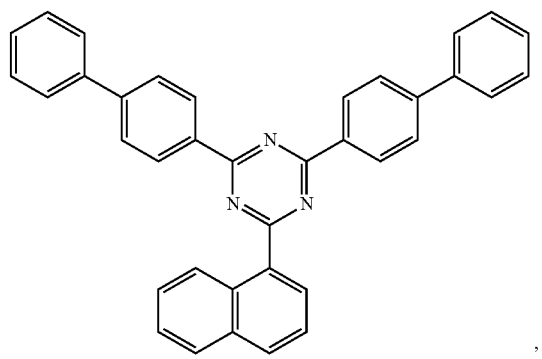
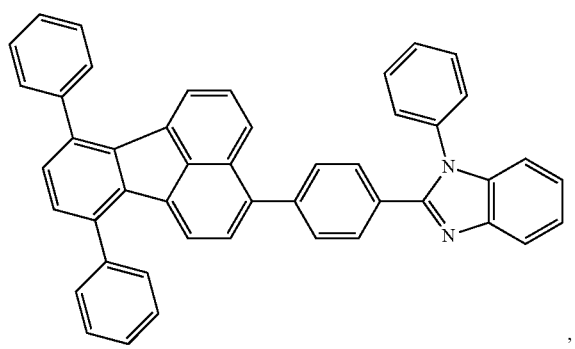
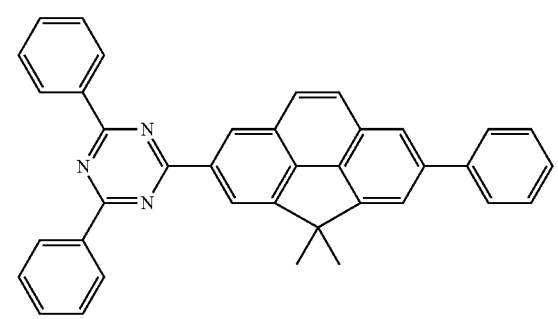
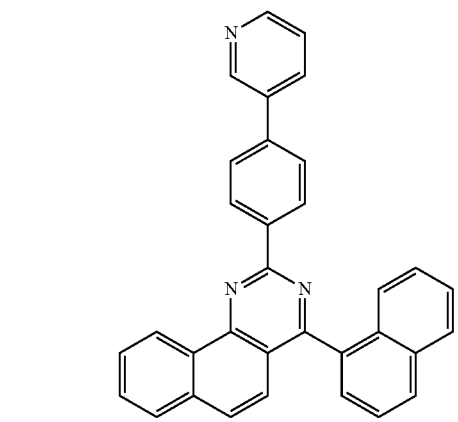
124
-continued
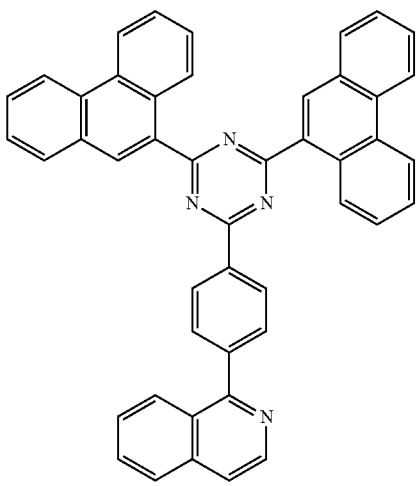
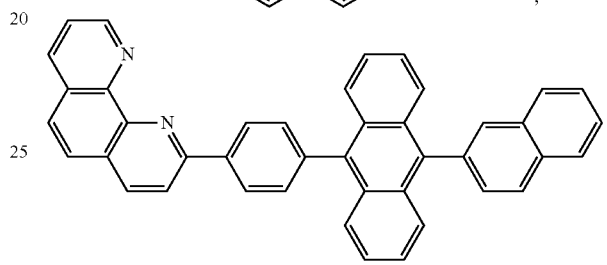
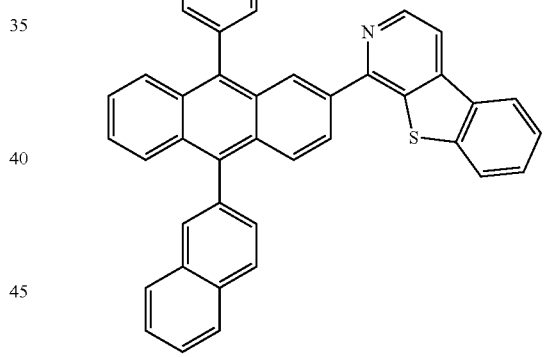
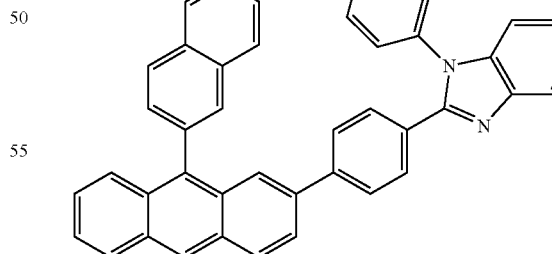

125
-continued
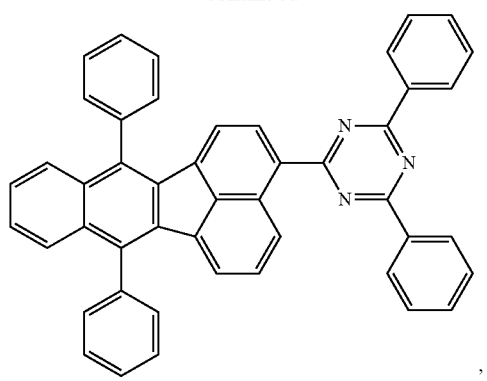
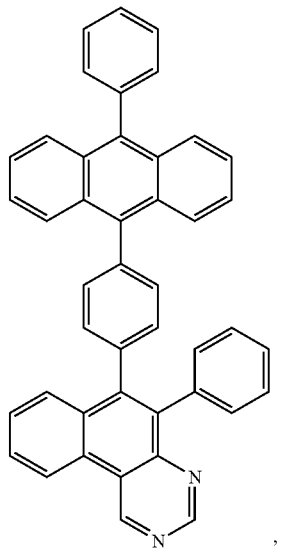
126
-continued
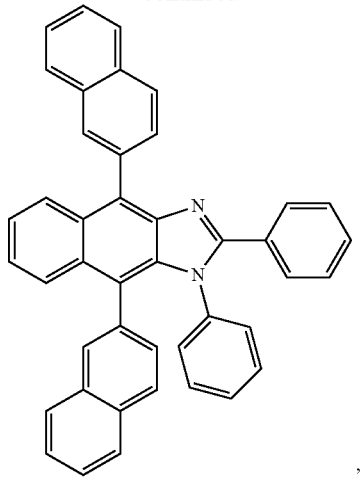
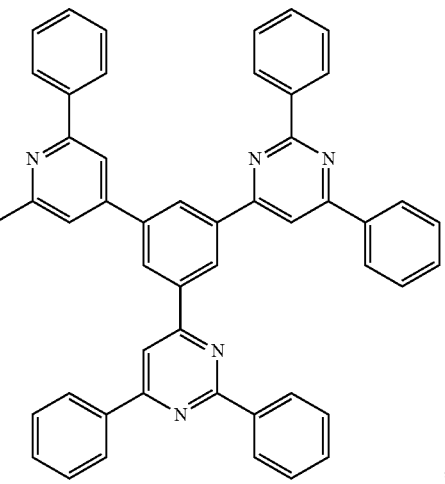
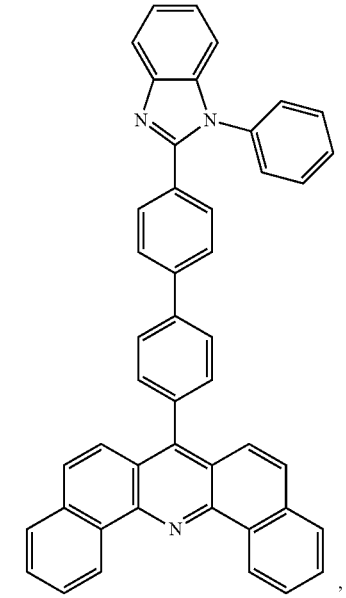

127
-continued
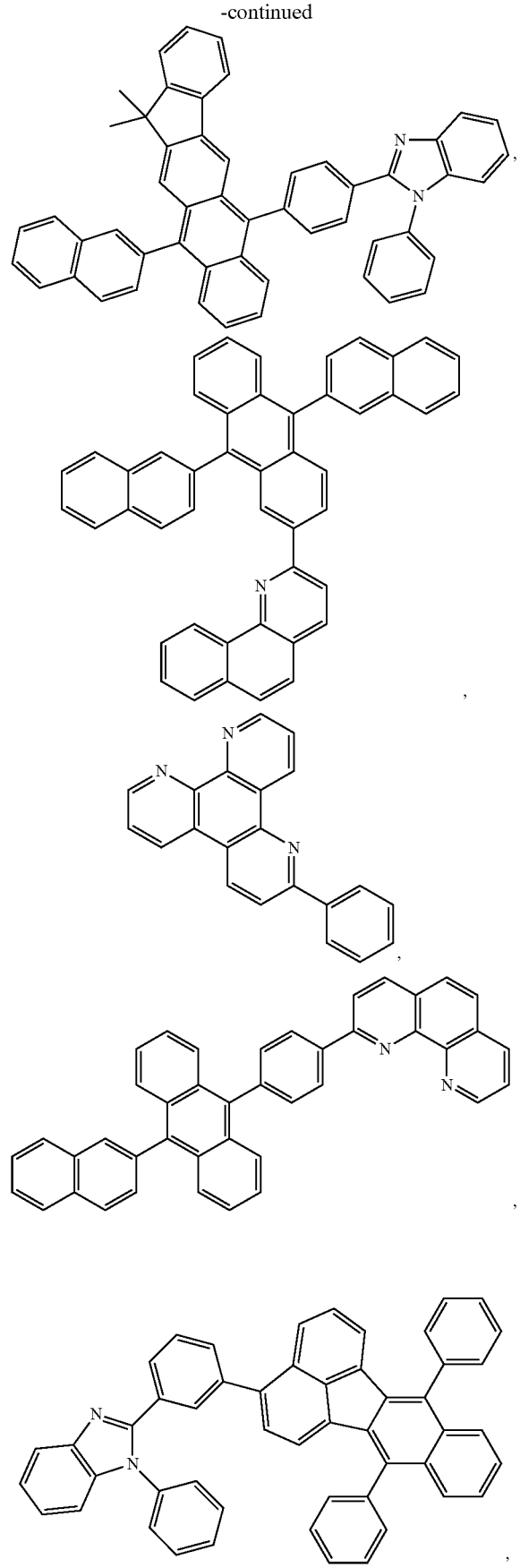
128
-continued
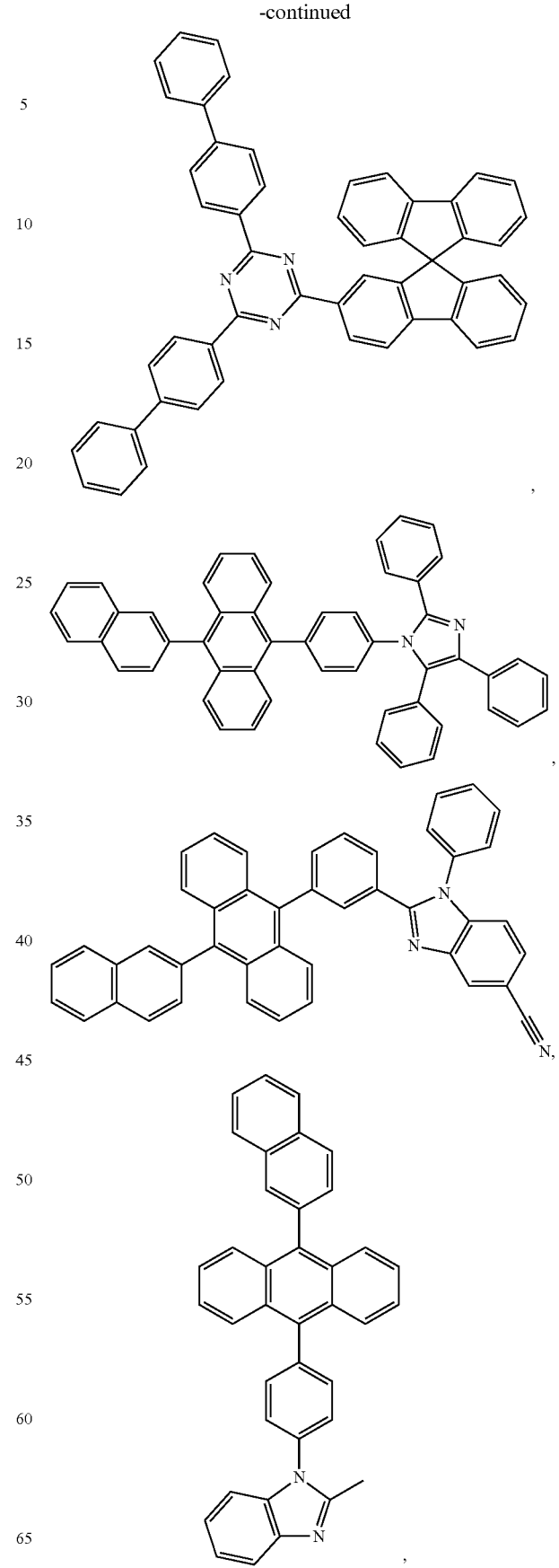

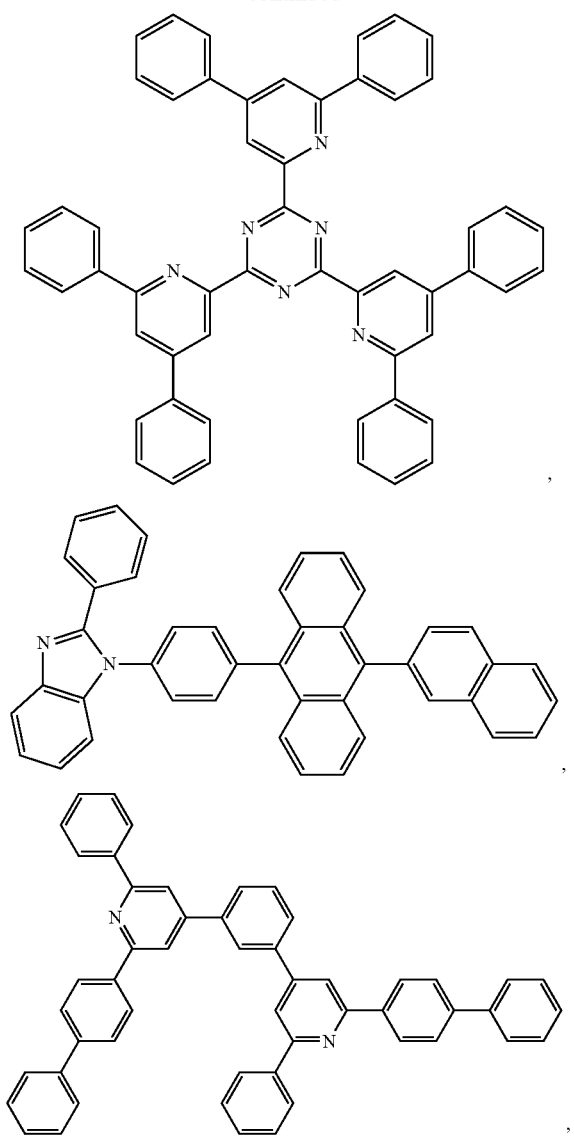

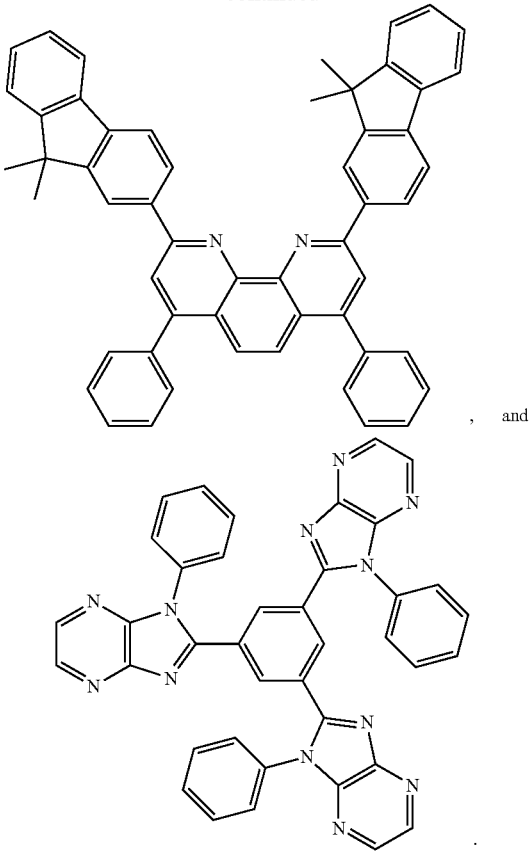

, and

Charge Generation Layer (CGL):

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

EXPERIMENTAL

Compound Synthesis

Chemical abbreviations used throughout this document are as follows:

SPhos is dicyclohexyl(2',6'-dimethoxy-[1,1'-biphenyl]-2-yl)phosphine, $Pd_2(dba)_3$ is tri(dibenzylideneacetone)dipalladium (0), $Pd(PPh_3)_4$ is tetrakis(triphenylphosphine)palladium (0), DCM is dichloromethane, and DME is dimethyoxyethane.

Synthesis of Compound B1:

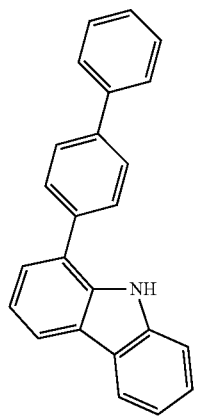

+

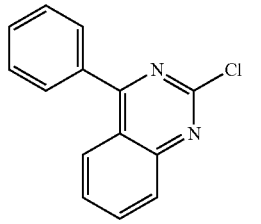

→

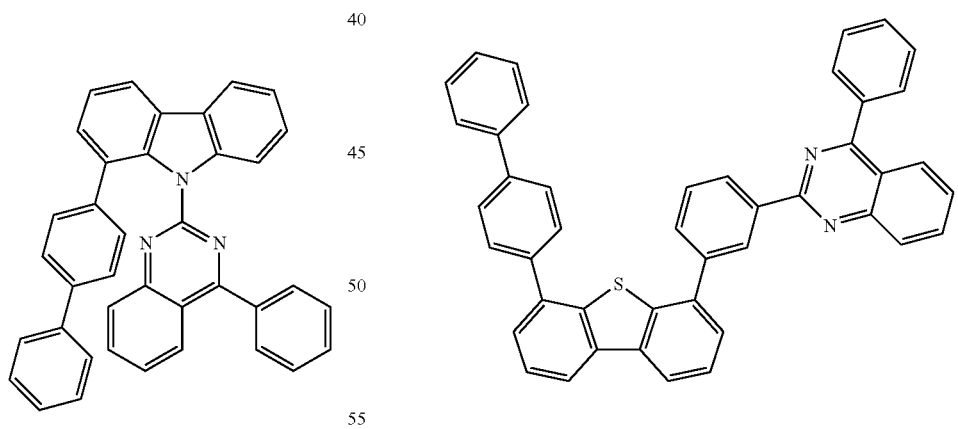

A solution of 2-chloro-4-phenylquinazoline (2.487 g, 10.33 mmol), 1-([1,1'-biphenyl]-4-yl)-9H-carbazole (3 g, 9.39 mmol), Pd$_2$(dba)$_3$ (0.602 g, 0.657 mmol), SPhos (0.553 g, 1.409 mmol) and tert-BuONa (2.257 g, 23.48 mmol) in m-xylene (100 ml) was refluxed for 4 h. After cooling to room temperature, the reaction was filtered through a short plug of Celite and the solvent was evaporated. The residue was purified by column chromatography on silica gel with heptane/DCM (6/4) as eluent and recrystallization from methanol to yield Compound B1 (4.5 g, 91%) as yellow crystals.

Synthesis of Compound C35

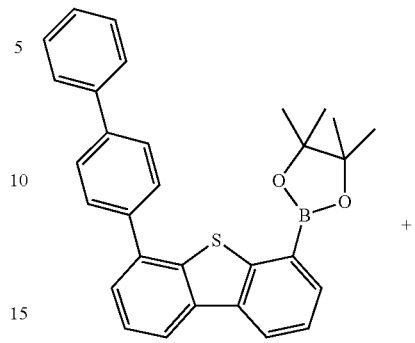 +

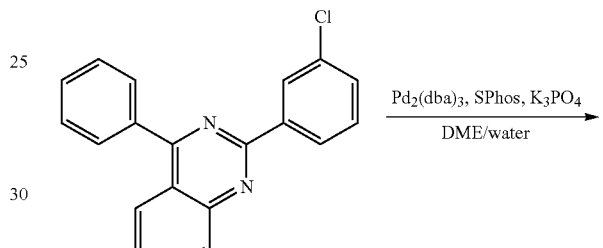

→

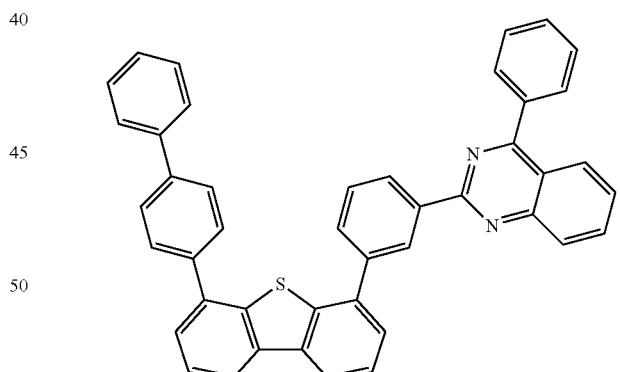

A solution of 2-(3-chlorophenyl)-4-phenylquinazoline (2.398 g, 7.57 mmol), 2-(6-([1,1'-biphenyl]-4-yl)dibenzo[b,d]thiophen-4-yl)-4,4,5,5-tetramethyl-1,3,2-dioxaborolane (3.5 g, 7.57 mmol) Pd$_2$(dba)$_3$ (0.139 g, 0.151 mmol), SPhos (0.119 g, 0.303 mmol) and K$_3$PO$_4$ (4.82 g, 22.71 mmol) in DME (100 ml) and water (25.00 ml) was refluxed overnight. After cooling to room temperature, the solvent was evaporated, and the residue was dissolved in toluene and filtered through a short plug of silica gel. Upon evaporation of the solvent, the crude product was triturated with boiling ethanol and ethyl acetate to yield Compound C35 (3.2 g, 5.19 mmol, 68.5% yield) as a white solid.

Synthesis of Compound C65

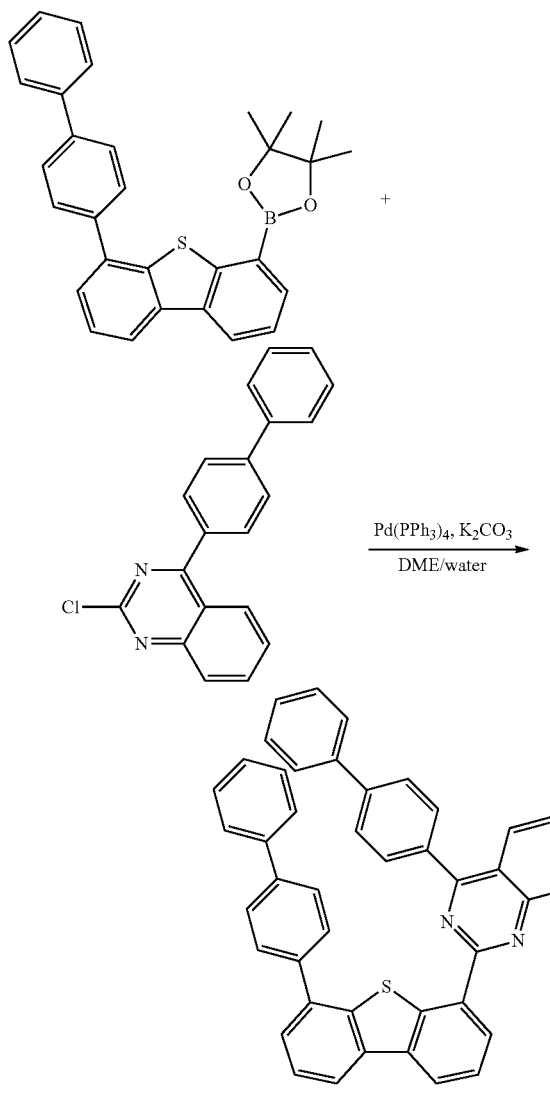

A solution of 4-([1,1'-biphenyl]-4-yl)-2-chloroquinazoline (2.80 g, 8.85 mmol), 2-(6-([1,1'-biphenyl]-4-yl)dibenzo[b,d]thiophen-4-yl)-4,4,5,5-tetramethyl-1,3,2-dioxaborolane (4.5 g, 9.73 mmol), Pd(PPh$_3$)$_4$ (0.204 g, 0.177 mmol), and K$_2$CO$_3$ (3.67 g, 26.5 mmol) in DME (80 ml) and water (15 ml) was refluxed under nitrogen overnight. After cooling to room temperature, the solid was collected by filtration, dissolved in boiling xylene (4 L) and filtered through a short plug of silica gel. Upon evaporation of the solvent, the crude product recrystallizes from xylene, and was triturated with ethyl acetate to yield Compound C65 (4.3 g, 6.97 mmol, 79% yield) as a white solid.

Application in OLED. All devices were fabricated by high vacuum (~$10^{-7}$ Torr) thermal evaporation. The anode electrode was 80 nm of indium tin oxide (ITO). The cathode electrode consisted of 1 nm of LiF followed by 100 nm of Al. All devices were encapsulated with a glass lid sealed with an epoxy resin in a nitrogen glove box (<1 ppm of H$_2$O and O$_2$) immediately after fabrication, and a moisture getter was incorporated inside the package.

Device Examples. A set of device examples have organic stacks consisting of, sequentially, from the ITO surface, 10 nm of LG101 (from LG Chem) as the hole injection layer (HIL), 45 nm of PPh-TPD as the hole-transport layer (HTL), 40 nm of emissive layer (EML), followed by 30 nm of aDBT-ADN with LiQ as the electron-transport layer (ETL). The EML has three components, 79 wt % of invented compounds (Compounds B1, C35 or C65) or comparative compounds (CC-1, CC-2 or CC-3) as the first host, 18 wt % GDH as the second host, and 3 wt % of RD as the dopant emitter. The structures of the compounds used are shown below.

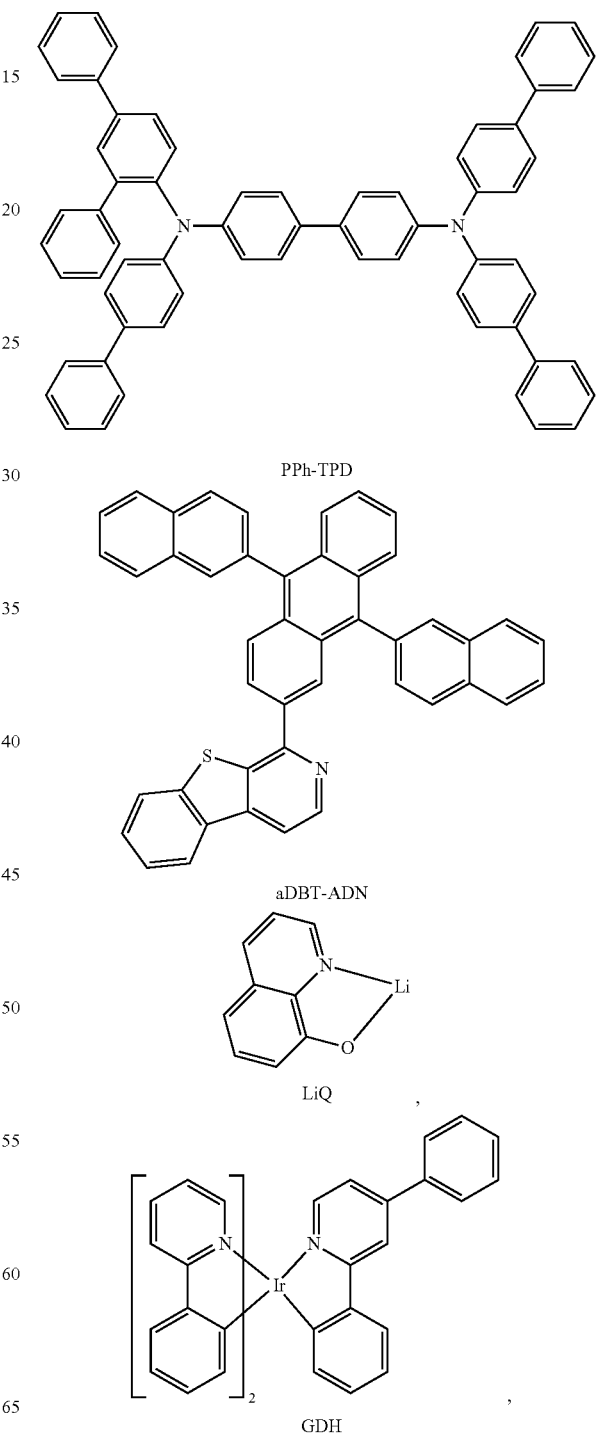

-continued

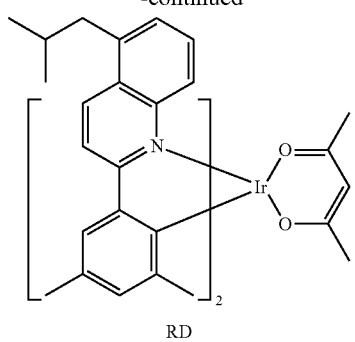

RD

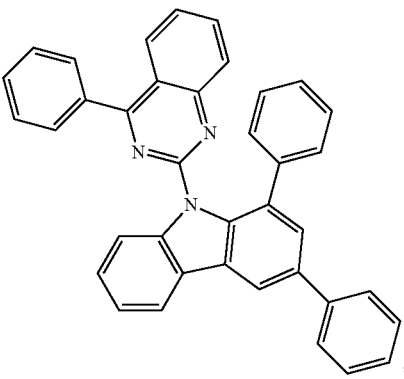
CC-1

Compound B1

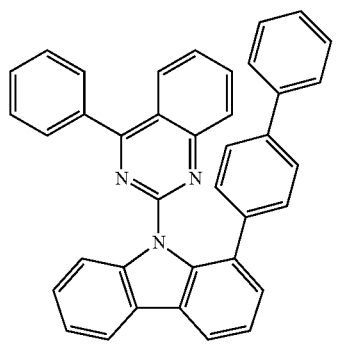

Compound C35

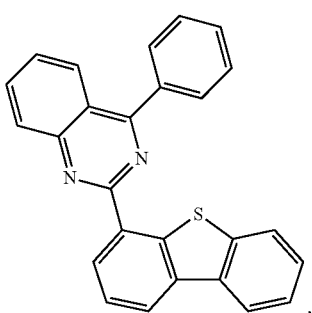
CC-2

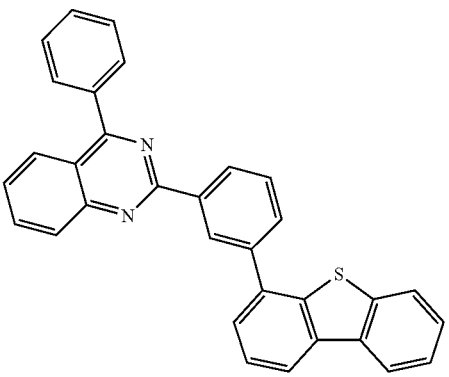
CC-3

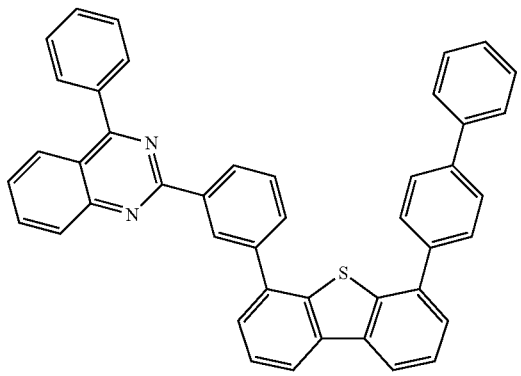

Compound C65

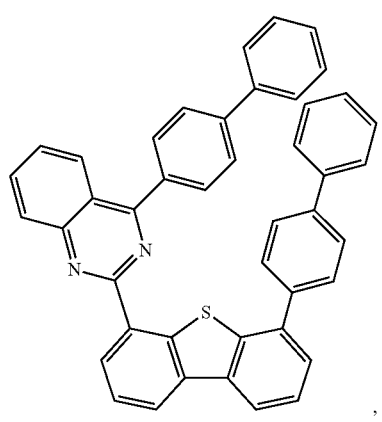

Table D1, below, is a summary of the device data, voltage (V), external quantum efficiency (EQE) and power efficiency (PE), recorded at 1000 nits for the devices. All devices were fabricated twice and the averaged data were used in this table.

| Device ID | First Host | Emission Color | V [V] | EQE [%] | PE [lm/W] |
|---|---|---|---|---|---|
| Device-1 | Compound B1 | Red | 2.4 | 24.9 | 40.9 |
| Device-2 | Compound C35 | Red | 2.7 | 27.5 | 39.8 |
| Device-3 | Compound C65 | Red | 2.4 | 25.9 | 38.5 |
| Device-C1 | CC-1 | Red | 3.2 | 25.4 | 32.6 |
| Device-C2 | CC-2 | Red | 4.2 | 23.6 | 21.5 |
| Device-C3 | CC-3 | Red | 3.4 | 20.5 | 24.8 |

The data in Table D1 shows that OLEDs (Device-1, Device-2 and Device-3) using inventive compounds (Compounds B1, C35 and C65) as the first host in the EML require lower driving voltage while achieving higher efficiency than their counterparts using comparative compound (CC-1, CC-2 and CC-3) as the first host. The superior performance of the inventive compounds may be attributable to their unique chemical structures that might have facilitated charge transport to maintain a more balanced charge carrier fluxes inside the devices, which is critical to promote OLED device performance.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:
1. A compound having Formula I:

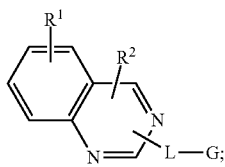

Formula I wherein L is selected from the group consisting of a direct bond, phenyl, biphenyl, terphenyl, fluorene, pyridine, pyrimidine, pyrazine, pyridazine, triazine, naphthalene, anthracene, and combinations thereof;
G is selected from the group consisting of:

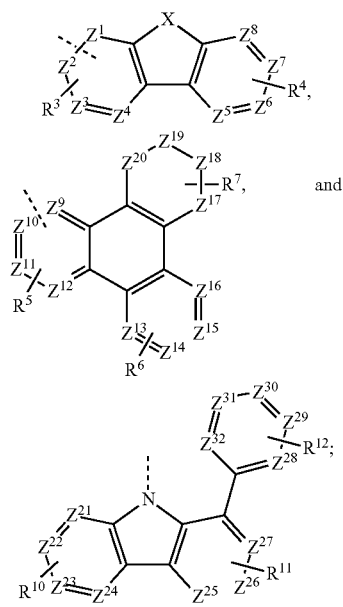

wherein $R^1$ to $R^7$ are independently selected from the group consisting of hydrogen, deuterium, alkyl, cycloalkyl, alkoxyl, halogen, nitro, silyl, benzene, biphenyl, terphenyl, naphthalene, phenanthrene, benzofuran, benzothiophene, benzoselenophene, dibenzofuran, dibenzothiophene, dibenzoselenophene, fluorene, triphenylene, pyridine, pyrimidine, pyrazine, pyridazine, triazine, quinoline, phenanthroline, aza-dibenzofuran, aza-dibenzothiophene, aza-dibenzoselenophene, aza-fluorene and aza-triphenylene, and combinations thereof;

wherein $R^{10}$ to $R^{11}$ are independently selected from the group consisting of hydrogen, deuterium, alkyl, heteroalkyl, cycloalkyl, alkoxyl, halogen, nitro, carbonyl, amino and silyl, and combinations thereof;

wherein $R^{12}$ is selected from the group consisting of hydrogen, deuterium, alkyl, heteroalkyl, cycloalkyl, alkoxyl, halogen, nitro, carbonyl, amino, silyl, aryl, heteroaryl, and combinations thereof and wherein one or more $R^{12}$ do not join or fuse to form a ring;

wherein $Z^1$ to $Z^{32}$ are independently selected from the group consisting of carbon and nitrogen;

wherein at least one of $Z^1$, $Z^2$, $Z^3$, $Z^4$, $Z^5$, $Z^6$, $Z^7$ and $Z^8$ is nitrogen; at least one of $Z^9$, $Z^{10}$, $Z^{11}$, $Z^{12}$, $Z^{13}$, $Z^{14}$, $Z^{15}$, $Z^{16}$, $Z^{17}$, $Z^{18}$, $Z^{19}$ and $Z^{20}$ is nitrogen; at least one of $Z^1$, $Z^2$, $Z^3$ and $Z^4$ is carbon; and at least one of $Z^9$, $Z^{10}$, $Z^{11}$ and $Z^{12}$ is carbon;

wherein when any of $Z^1$ to $Z^{32}$ is nitrogen, there is no substitution on that nitrogen;

wherein $R^1$, $R^4$, $R^6$, $R^7$ and $R^{10}$ independently represent mono, di, tri or tetra substitution, or no substitution;

wherein $R^3$, $R^5$, and $R^{11}$ each independently represent mono, di or tri substitution, or no substitution;

wherein $R^2$ represents mono substitution, or no substitution;

wherein $R^{12}$ represents mono, di, tri, tetra or penta substitution, or no substitution;

wherein X is selected from the group consisting of O, S, and Se; and wherein L is optionally further substituted with one or more substituents selected from the group consisting of deuterium, alkyl, alkoxyl, halogen, silyl, nitro, benzene, biphenyl, terphenyl, naphthalene, phenanthrene, dibenzofuran, dibenzothiophene, dibenzoselenophene, fluorene, triphenylene, pyridine, pyrimidine, pyrazine, pyridazine, triazine, quinoline, phenanthroline , aza-dibenzofuran, aza-dibenzothiophene, aza-dibenzoselenophene, aza-fluorene and aza-triphenylene, and combinations thereof.

2. The compound of claim 1, wherein the compound is selected from the group consisting of:

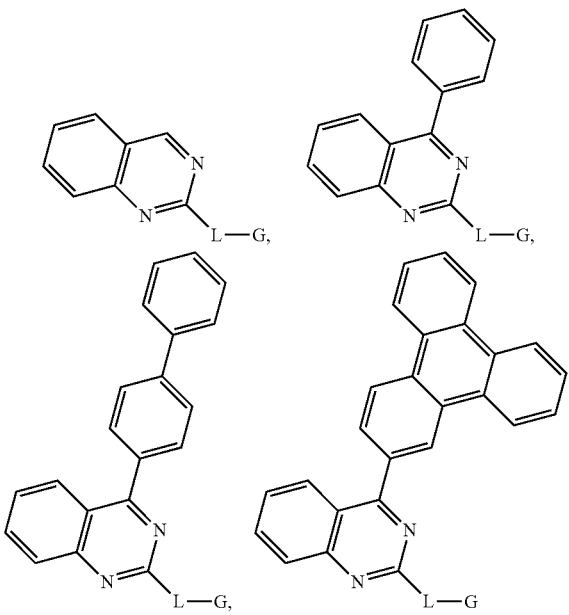

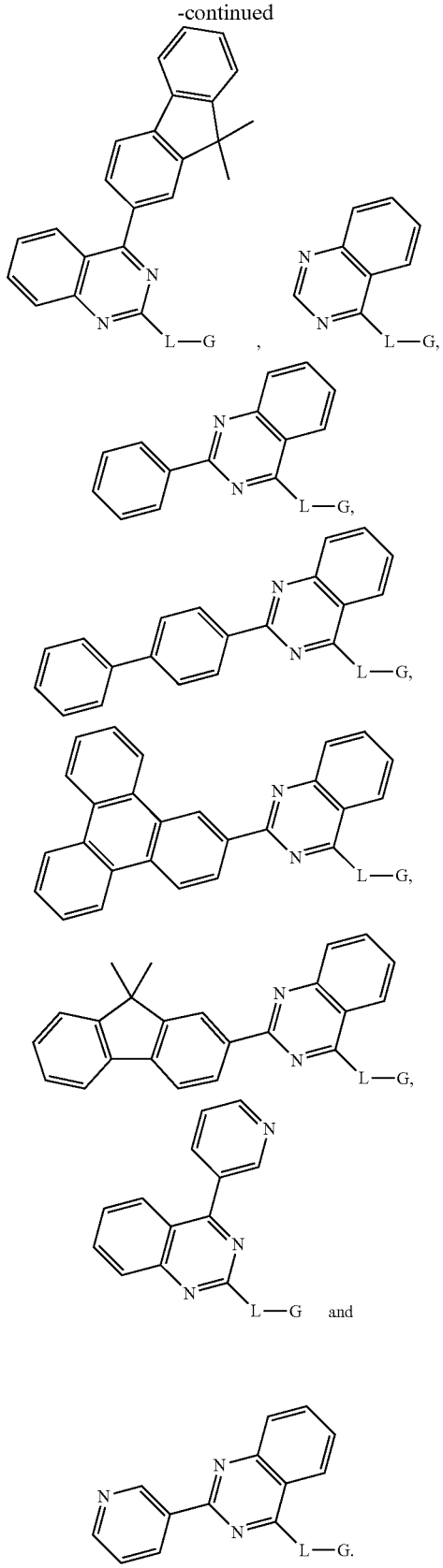
3. The compound of claim 1, wherein the compound is selected from the group consisting of:
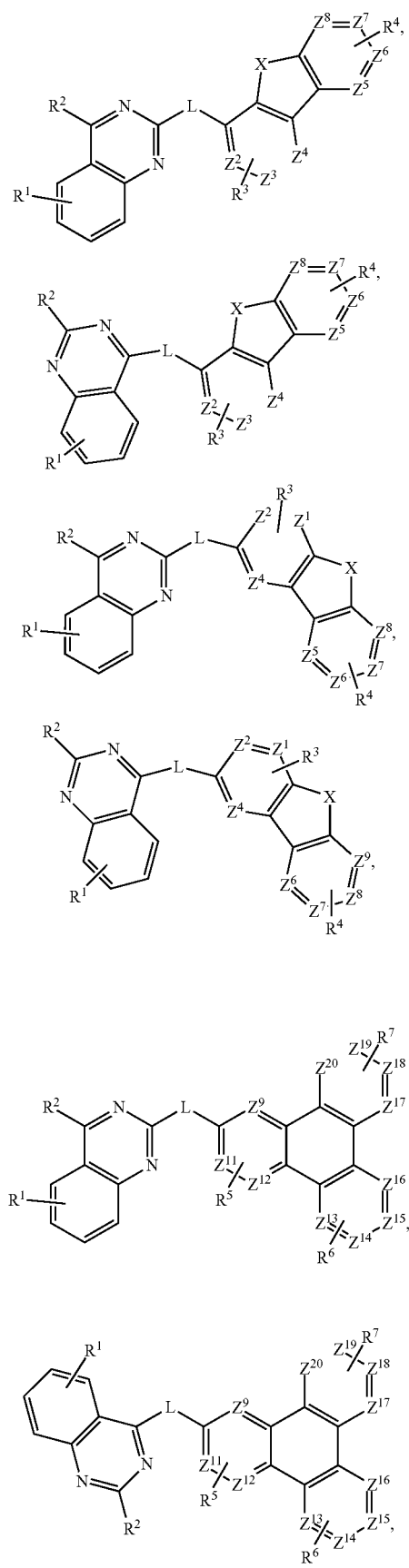

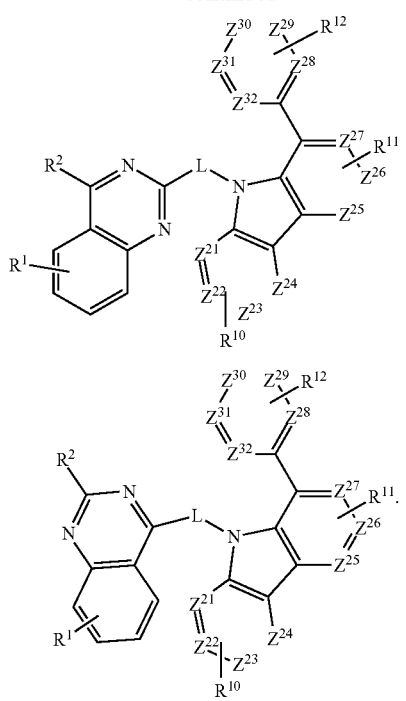
4. The compound of claim 1, wherein G is selected from the group consisting of:
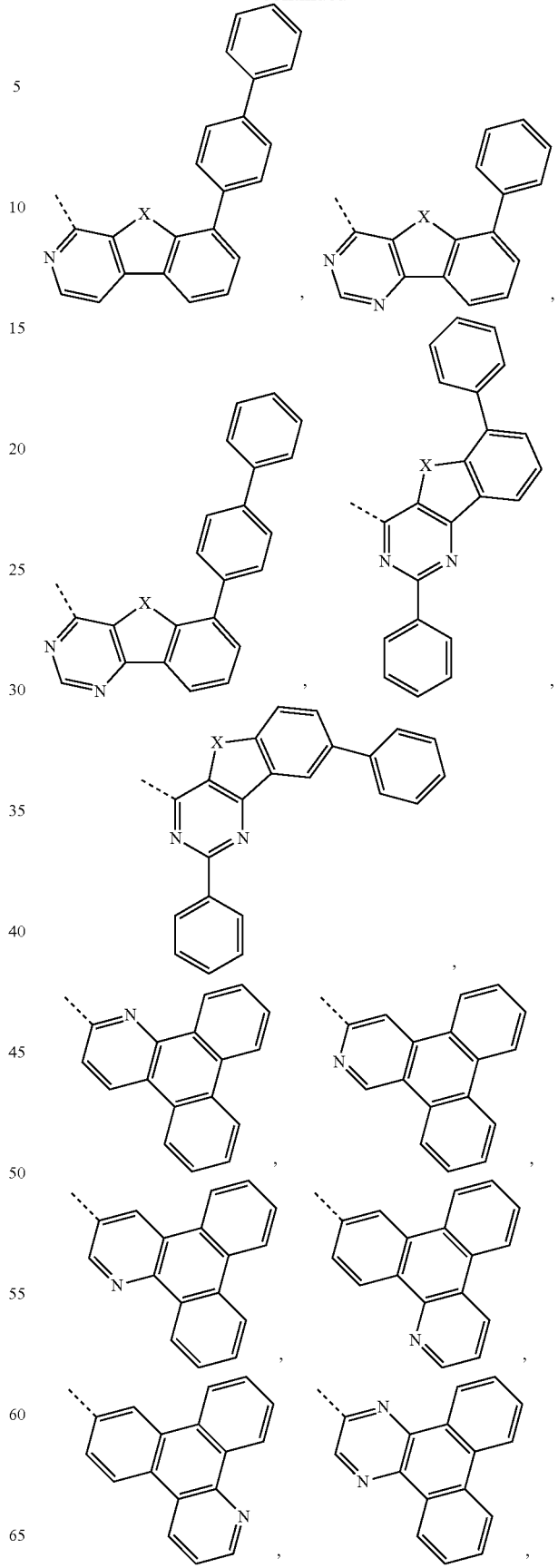

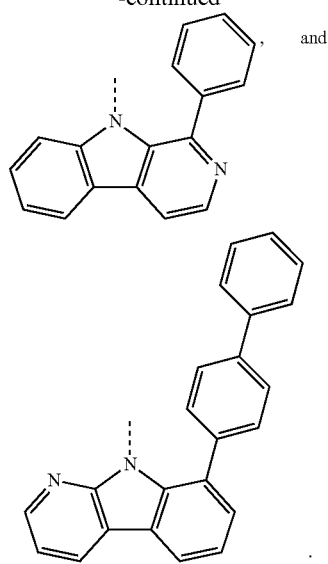
5. The compound of claim 1, wherein G is selected from the group consisting of:
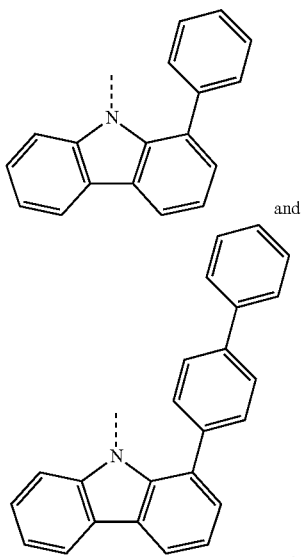
6. The compound of claim 1, wherein L is selected from the group consisting of:
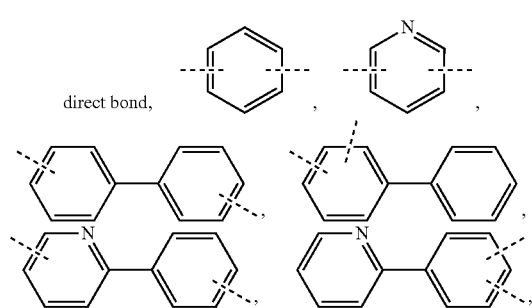
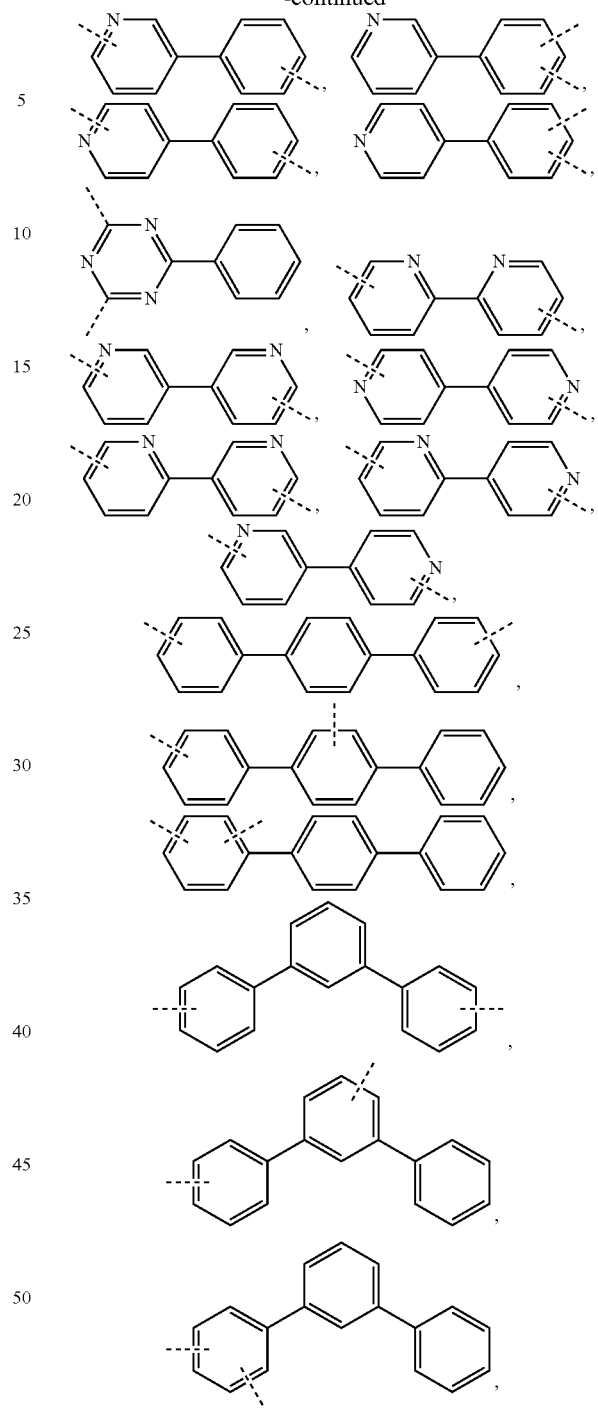
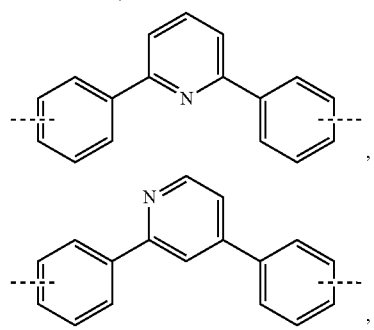

-continued
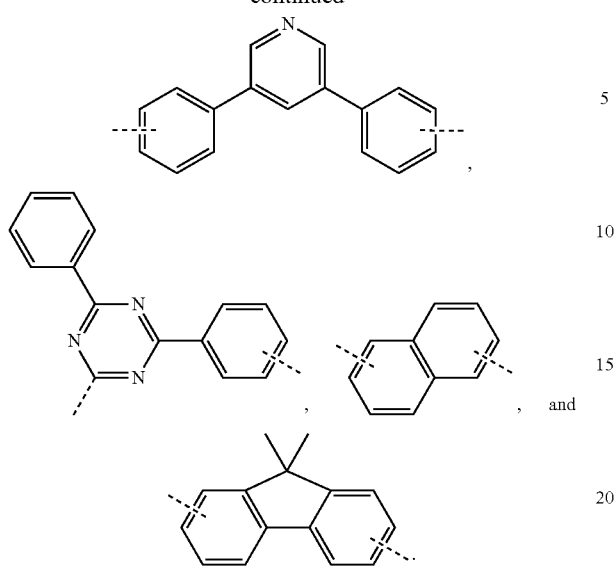
7. The compound of claim 1, wherein the compound is selected from the group consisting of:
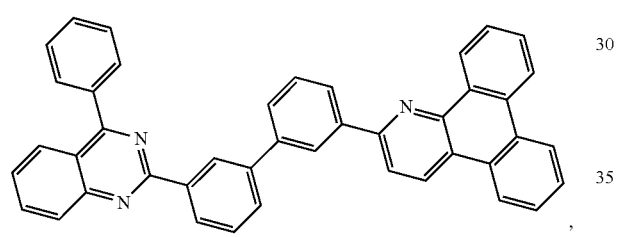
Compound A1
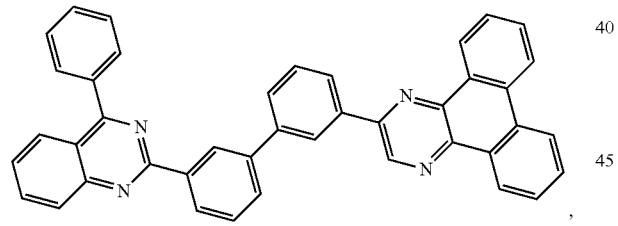
Compound A2
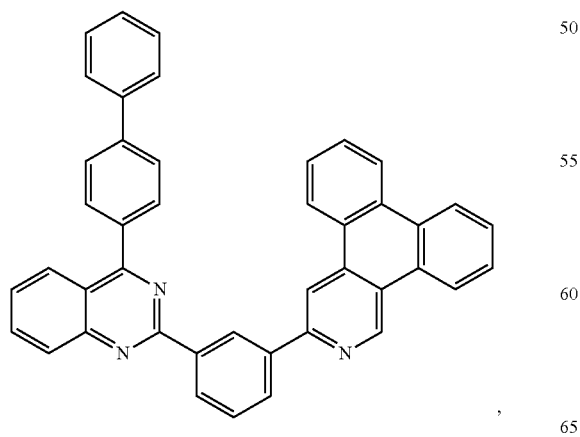
Compound A3
-continued
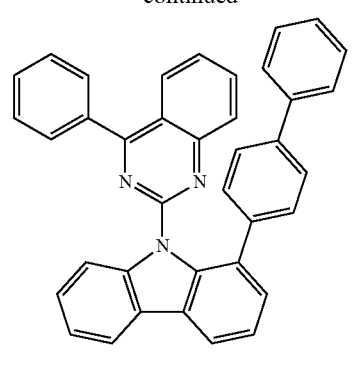
Compound B1
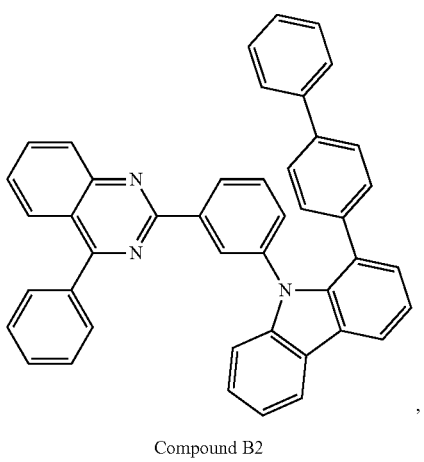
Compound B2
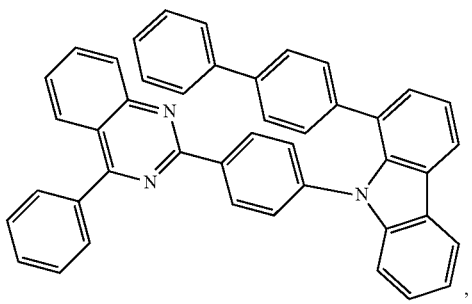
Compound B3
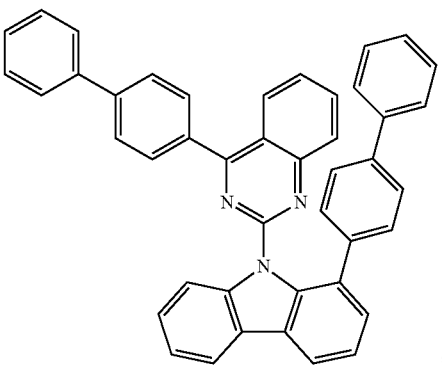
Compound B4

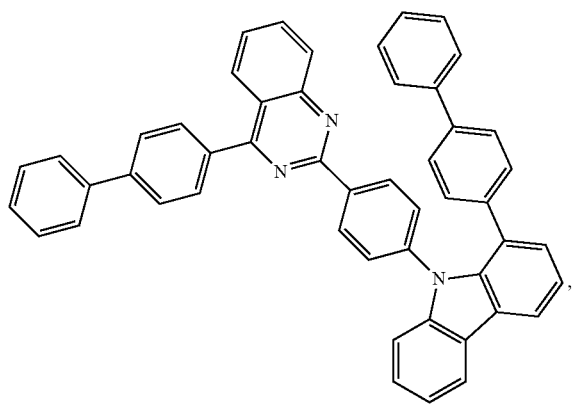
Compound B5
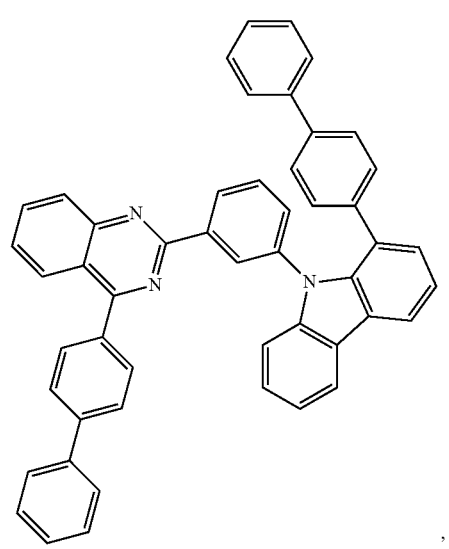
Compound B6
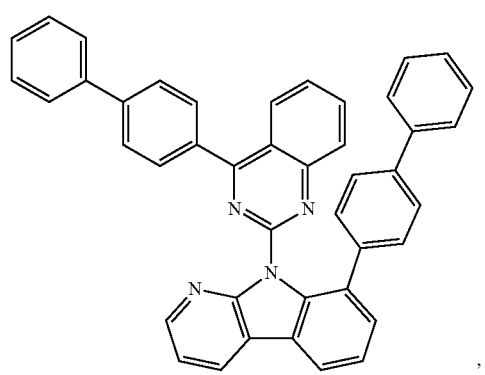
Compound B9
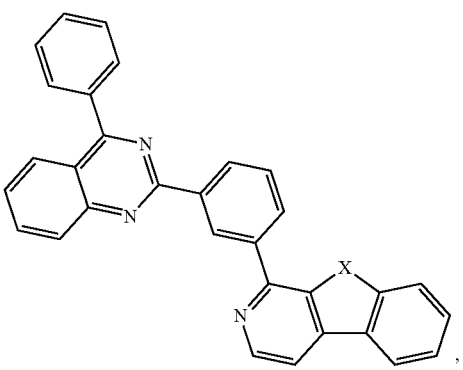
Compound D1, X is O;
Compound D2, X is S;
Compound D3, X is Se.
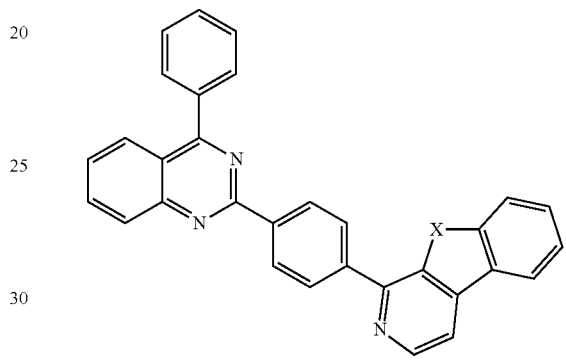
Compound D4, X is O;
Compound D5, X is S;
Compound D6, X is Se.
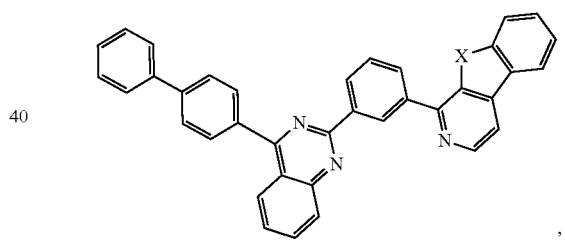
Compound D7, X is O;
Compound D8, X is S;
Compound D9, X is Se.
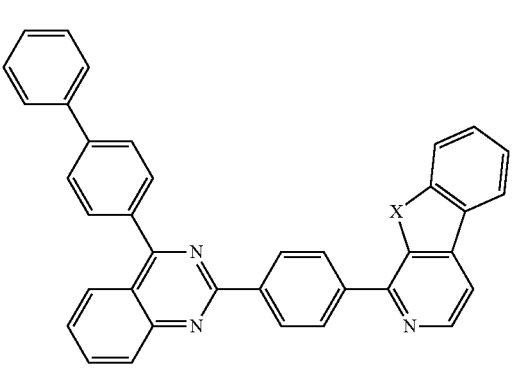
Compound D10, X is O;
Compound D11, X is S;
Compound D12, X is Se.

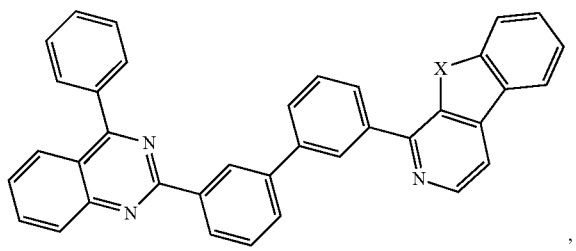

Compound D13, X is O;
Compound D14, X is S;
Compound D15, X is Se.

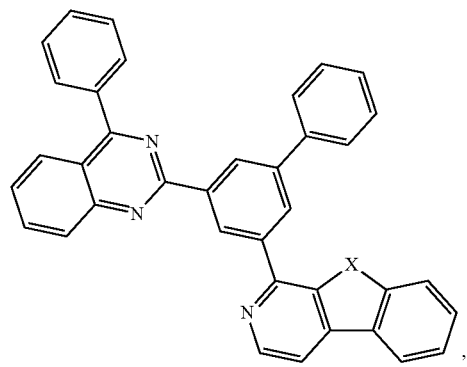

Compound D16, X is O;
Compound D17, X is S;
Compound D18, X is Se.

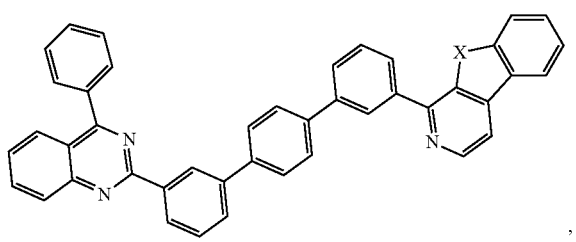

Compound D19, X is O;
Compound D20, X is S;
Compound D21, X is Se.

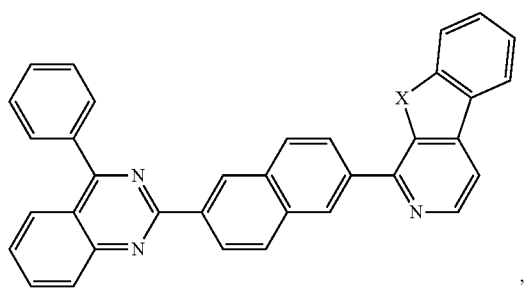

Compound D22, X is O;
Compound D23, X is S;
Compound D24, X is Se.

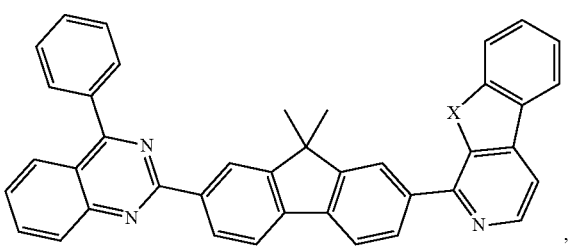

Compound D25, X is O;
Compound D26, X is S;
Compound D27, X is Se.

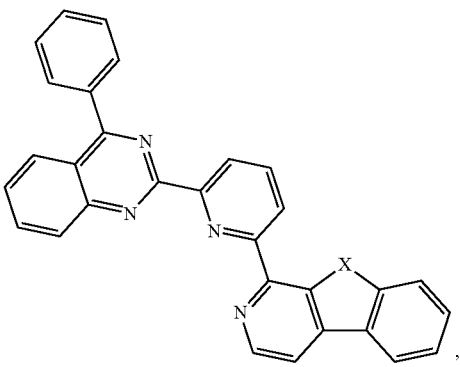

Compound D28, X is O;
Compound D29, X is S;
Compound D30, X is Se.

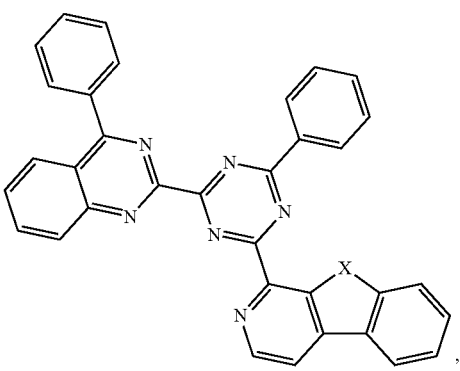

Compound D31, X is O;
Compound D32, X is S;
Compound D33, X is Se.

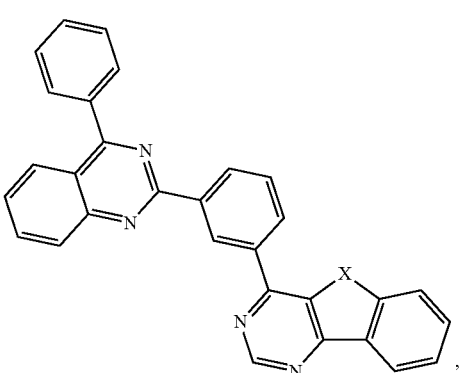

Compound D34, X is O;
Compound D35, X is S;
Compound D36, X is Se.

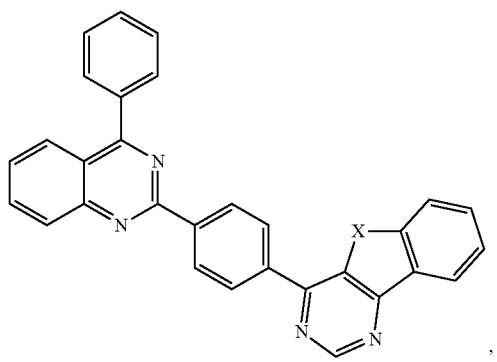

Compound D37, X is O;
Compound D38, X is S;
Compound D39, X is Se.

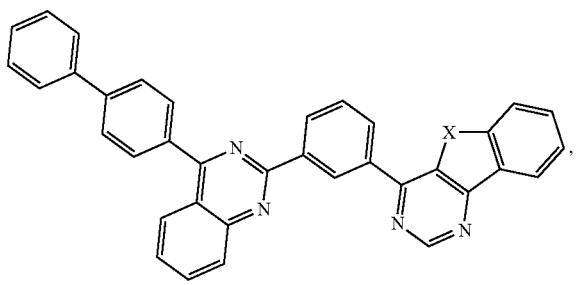

Compound D40, X is O;
Compound D41, X is S;
Compound D42, X is Se.

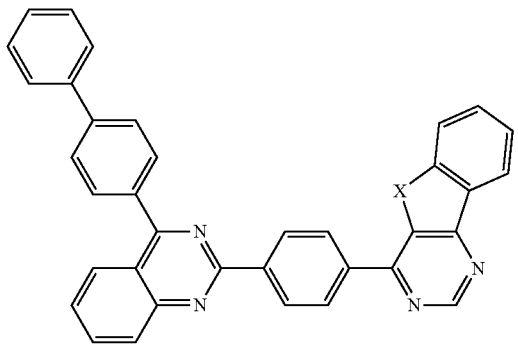

Compound D43, X is O;
Compound D44, X is S;
Compound D45, X is Se.

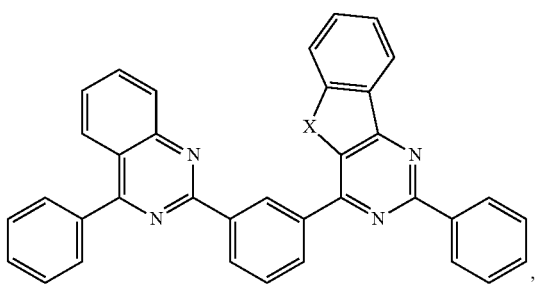

Compound D46, X is O;
Compound D47; X is S;
Compound D48, X is Se.

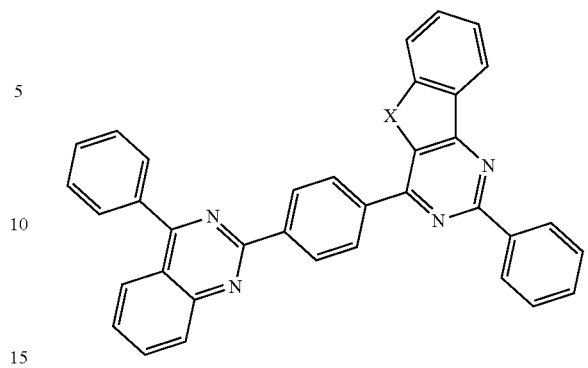

Compound D49, X is O;
Compound D50; X is S;
Compound D51, X is Se.

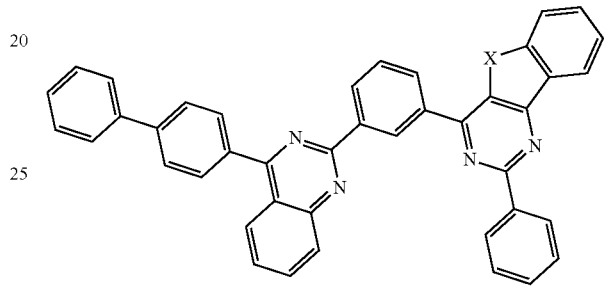

Compound D52, X is O;
Compound D53; X is S;
Compound D54, X is Se.

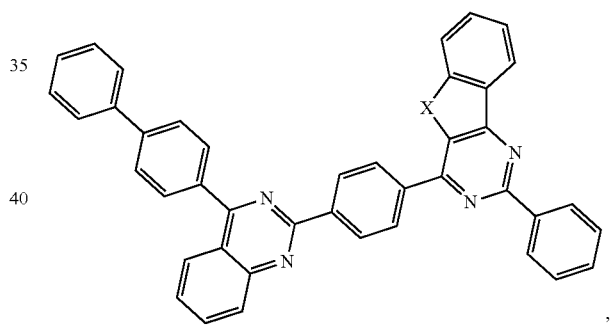

Compound D55, X is O;
Compound D56, X is S;
Compound D57, X is Se.

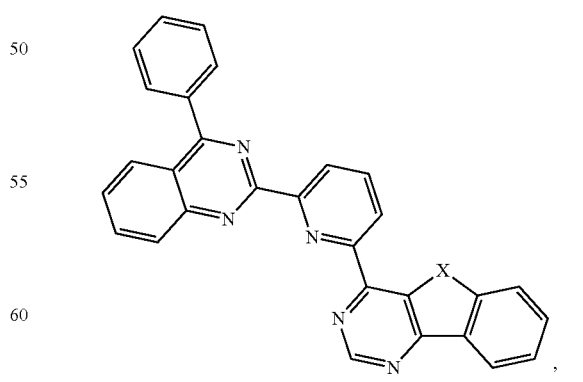

Compound D58, X is O;
Compound D59, X is S;
Compound 60, X is Se.

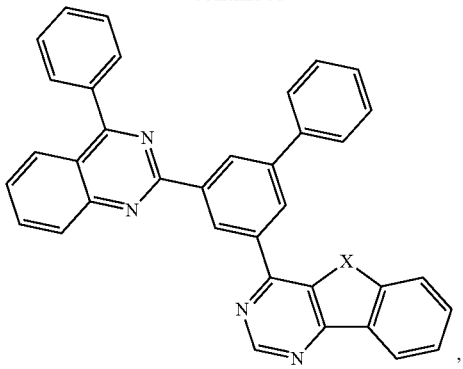

Compound D61, X is O;
Compound D62, X is S;
Compound D63, X is Se.

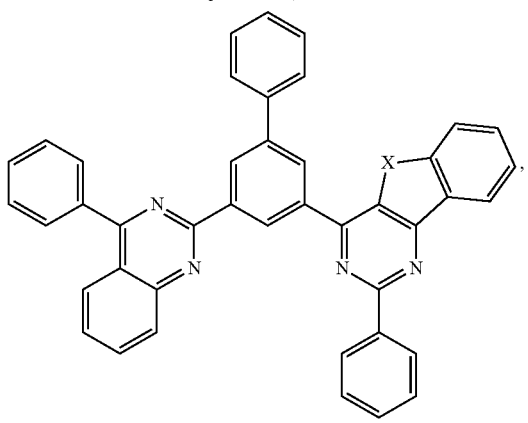

Compound D64, X is O;
Compound D65, X is S;
Compound D66, X is Se.

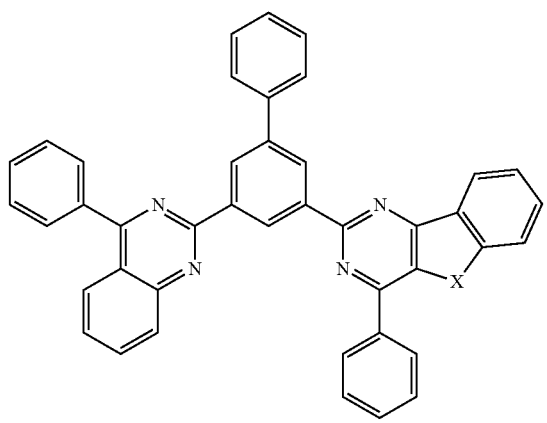

Compound D67, X is O;
Compound D68, X is S;
Compound D69, X is Se.

8. An organic light emitting device (OLED) comprising:
an anode;
a cathode; and
an organic layer, disposed between the anode and the cathode, comprising a compound having Formula I:

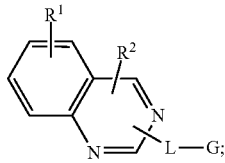

Formula I

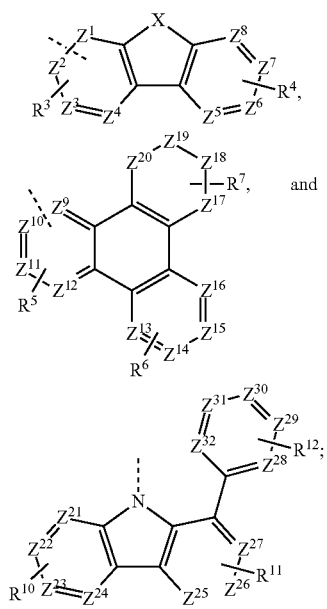

wherein L is selected from the group consisting of a direct bond, phenyl, biphenyl, terphenyl, fluorene, pyridine, pyrimidine, pyrazine, pyridazine, triazine, naphthalene, anthracene, and combinations thereof;
G is selected from the group consisting of:

wherein $R^1$ to $R^7$ are independently selected from the group consisting of hydrogen, deuterium, alkyl, cycloalkyl, alkoxyl, halogen, nitro, silyl, benzene, biphenyl, terphenyl, naphthalene, phenanthrene, benzofuran, benzothiophene, benzoselenophene, dibenzofuran, dibenzothiophene, dibenzoselenophene, fluorene, triphenylene, pyridine, pyrimidine, pyrazine, pyridazine, triazine, quinoline, phenanthroline, aza-dibenzofuran, aza-dibenzothiophene, aza-dibenzoselenophene, aza-fluorene and aza-triphenylene, and combinations thereof;
wherein $R^{10}$ to $R^{11}$ are independently selected from the group consisting of hydrogen, deuterium, alkyl, heteroalkyl, cycloalkyl, alkoxyl, halogen, nitro, carbonyl, amino and silyl, and combinations thereof;
wherein $R^{12}$ is selected from the group consisting of hydrogen, deuterium, alkyl, heteroalkyl, cycloalkyl, alkoxyl, halogen, nitro, carbonyl, amino, silyl, aryl, heteroaryl, and combinations thereof and wherein one or more $R^{12}$ do not join or fuse to form a ring;
wherein $Z^1$ to $Z^{32}$ are independently selected from the group consisting of carbon and nitrogen;
wherein at least one of $Z^1$, $Z^2$, $Z^3$, $Z^4$, $Z^5$, $Z^6$, $Z^7$ and $Z^8$ is nitrogen; at least one of $Z^9$, $Z^{10}$, $Z^{11}$ and $Z^{12}$, $Z^{13}$, $Z^{14}$, $Z^{15}$, $Z^{16}$, $Z^{17}$, $Z^{18}$, $Z^{19}$ and $Z^{20}$ is nitrogen; at least one of $Z^1$, $Z^2$, $Z^3$ and $Z^4$ is carbon; and at least one of $Z^9$, $Z^{10}$, $Z^{11}$ and $Z^{12}$ is carbon;

wherein when any of $Z^1$ to $Z^{32}$ is nitrogen, there is no substitution on that nitrogen;

wherein $R^1$, $R^4$, $R^6$, $R^7$ and $R^{10}$ independently represent mono, di, tri or tetra substitution, or no substitution;

wherein $R^3$, $R^5$, and $R^{11}$ each independently represent mono, di or tri substitution, or no substitution;

wherein $R^2$ represents mono substitution, or no substitution;

wherein $R^{12}$ represents mono, di, tri, tetra or penta substitution, or no substitution;

wherein X is selected from the group consisting of O, S, and Se; and wherein L is optionally further substituted with one or more substituents selected from the group consisting of deuterium, alkyl, alkoxyl, halogen, silyl, nitro, benzene, biphenyl, terphenyl, naphthalene, phenanthrene, dibenzofuran, dibenzothiophene, dibenzoselenophene, fluorene, triphenylene, pyridine, pyrimidine, pyrazine, pyridazine, triazine, quinoline, phenanthroline, aza-dibenzofuran, aza-dibenzothiophene, aza-dibenzoselenophene, aza-fluorene and aza-triphenylene, and combinations thereof.

9. The OLED of claim 8, wherein the organic layer is an emissive layer and the compound of Formula I is a host.

10. The OLED of claim 8, wherein the organic layer further comprises a phosphorescent emissive dopant; wherein the emissive dopant is a transition metal complex having at least one ligand or part of the ligand if the ligand is more than bidentate selected from the group consisting of:

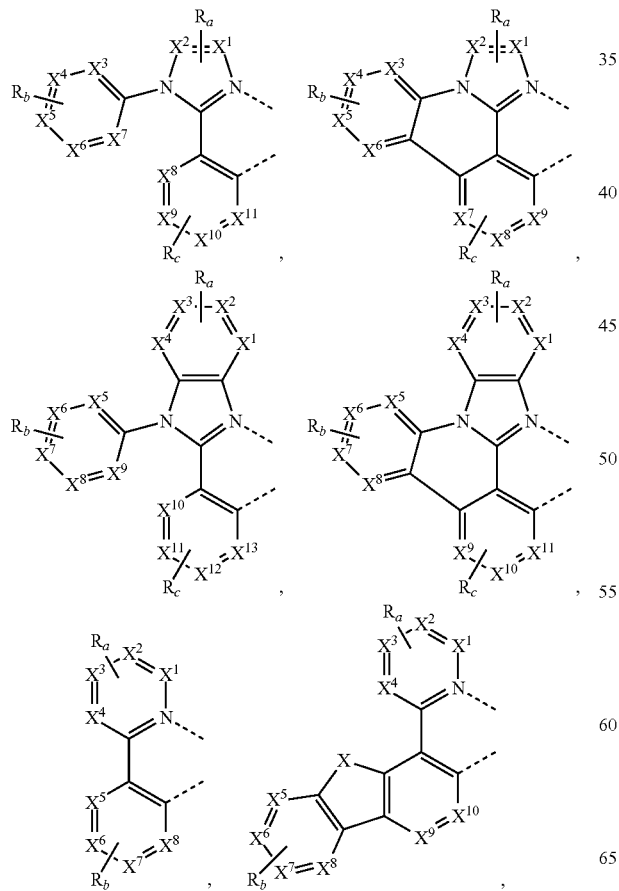

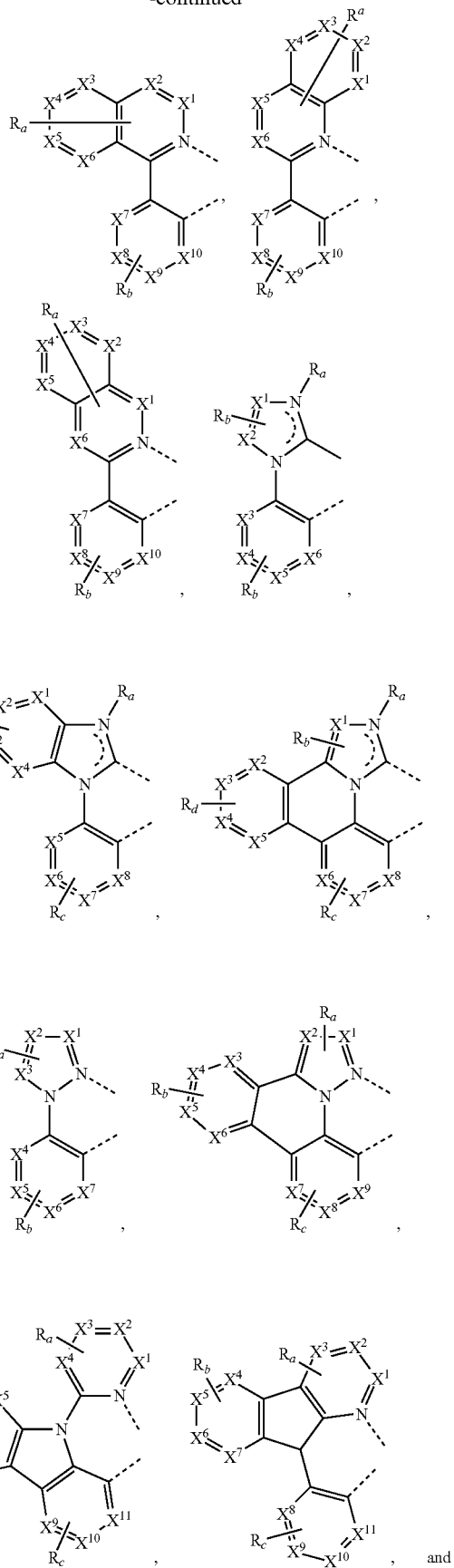

, and

-continued

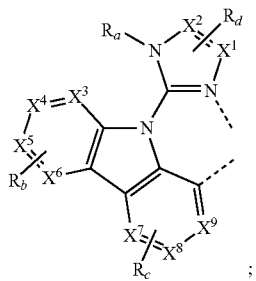

wherein each $X^1$ to $X^{13}$ are independently selected from the group consisting of carbon and nitrogen;

wherein X is selected from the group consisting of BR', NR', PR', O, S, Se, C=O, S=O, SO$_2$, CR'R", SiR'R", and GeR'R";

wherein R' and R" are optionally fused or joined to form a ring;

wherein each $R_a$, $R_b$, $R_c$, and $R_d$ may represent from mono substitution to the possible maximum number of substitution, or no substitution;

wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents of $R_a$, $R_b$, $R_c$, and $R_d$ are optionally fused or joined to form a ring or form a multidentate ligand.

11. The OLED of claim 8, wherein the organic layer is a blocking layer and the compound of Formula I is a blocking material in the organic layer.

12. The OLED of claim 8, wherein the organic layer is a transporting layer and the compound of Formula I is a transporting material in the organic layer.

13. The OLED of claim 8, wherein the OLED is incorporated into a device selected from the group consisting of a consumer product, an electronic component module, and a lighting panel.

14. A formulation comprising a compound having Formula I:

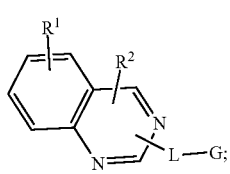
Formula I wherein L is selected from the group consisting of a direct bond, phenyl, biphenyl, terphenyl, fluorene, pyridine, pyrimidine, pyrazine, pyridazine, triazine, naphthalene, anthracene, and combinations thereof;

G is selected from the group consisting of:

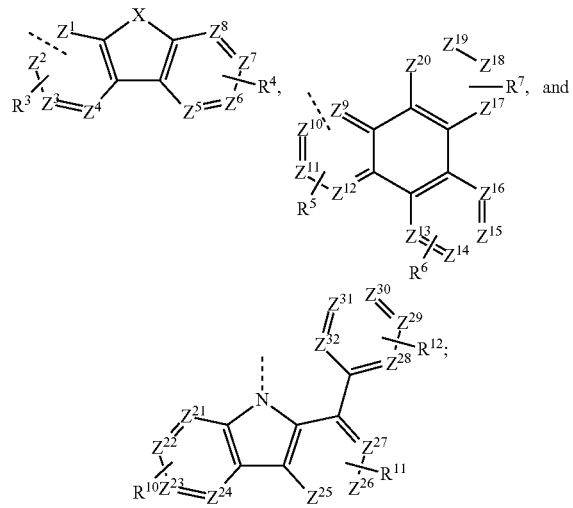

wherein $R^1$ to $R^7$ are independently selected from the group consisting of hydrogen, deuterium, alkyl, cycloalkyl, alkoxyl, halogen, nitro, silyl, benzene, biphenyl, terphenyl, naphthalene, phenanthrene, benzofuran, benzothiophene, benzoselenophene, dibenzofuran, dibenzothiophene, dibenzoselenophene, fluorene, triphenylene, pyridine, pyrimidine, pyrazine, pyridazine, triazine, quinoline, phenanthroline, aza-dibenzofuran, aza-dibenzothiophene, aza-dibenzoselenophene, aza-fluorene and aza-triphenylene, and combinations thereof;

wherein $R^{10}$ to $R^{11}$ are independently selected from the group consisting of hydrogen, deuterium, alkyl, heteroalkyl, cycloalkyl, alkoxyl, halogen, nitro, carbonyl, amino and silyl, and combinations thereof;

wherein $R^{12}$ is selected from the group consisting of hydrogen, deuterium, alkyl, heteroalkyl, cycloalkyl, alkoxyl, halogen, nitro, carbonyl, amino, silyl, aryl, heteroaryl, and combinations thereof and wherein one or more $R^{12}$ do not join or fuse to form a ring;

wherein $Z^1$ to $Z^{32}$ are independently selected from the group consisting of carbon and nitrogen;

wherein at least one of $Z^1$, $Z^2$, $Z^3$, $Z^4$, $Z^5$, $Z^6$, $Z^7$ and $Z^8$ is nitrogen; at least one of $Z^9$, $Z^{10}$, $Z^{11}$, $Z^{12}$, $Z^{13}$, $Z^{14}$, $Z^{15}$, $Z^{16}$, $Z^{17}$, $Z^{18}$, $Z^{19}$ and $Z^{20}$ is nitrogen; at least one of $Z^1$, $Z^2$, $Z^3$ and $Z^4$ is carbon; and at least one of $Z^9$, $Z^{10}$, $Z^{11}$ and $Z^{12}$ is carbon;

wherein when any of $Z^1$ to $Z^{32}$ is nitrogen, there is no substitution on that nitrogen;

wherein $R^1$, $R^4$, $R^6$, $R^7$ and $R^{10}$ independently represent mono, di, tri or tetra substitution, or no substitution;

wherein $R^3$, $R^5$, and $R^{11}$ each independently represent mono, di or tri substitution, or no substitution;

wherein $R^2$ represents mono substitution, or no substitution;

wherein $R^{12}$ represents mono, di, tri, tetra or penta substitution, or no substitution;

wherein X is selected from the group consisting of O, S, and Se; and wherein L is optionally further substituted with one or more substituents selected from the group consisting of deuterium, alkyl, alkoxyl, halogen, silyl, nitro, benzene, biphenyl, terphenyl, naphthalene, phenanthrene, dibenzofuran, dibenzothiophene, dibenzoselenophene, fluorene, triphenylene, pyridine, pyrimidine, pyrazine, pyridazine, triazine, quinoline, phenanthroline , aza-dibenzofuran, aza-dibenzothiophene, aza-dibenzoselenophene, aza-fluorene and aza-triphenylene, and combinations thereof.

\* \* \* \* \*